US011617559B2

(12) United States Patent
Samec et al.

(10) Patent No.: US 11,617,559 B2
(45) Date of Patent: Apr. 4, 2023

(54) AUGMENTED REALITY SYSTEMS AND METHODS FOR USER HEALTH ANALYSIS

(71) Applicant: Magic Leap, Inc., Plantation, FL (US)

(72) Inventors: Nicole Elizabeth Samec, Fort Lauderdale, FL (US); Mark Baerenrodt, Millbrae, CA (US); Nastasja U. Robaina, Coconut Grove, FL (US); Charlotte Dorothea Wilhelmina Vinkers, Fort Lauderdale, FL (US); Christopher M. Harrises, Nashua, NH (US); Nicholas Atkinson Kramer, Fort Lauderdale, FL (US)

(73) Assignee: Magic Leap, Inc., Plantation, FL (US)

( * ) Notice: Subject to any disclaimer, the term of this patent is extended or adjusted under 35 U.S.C. 154(b) by 30 days.

(21) Appl. No.: 17/385,612

(22) Filed: Jul. 26, 2021

(65) Prior Publication Data
US 2022/0015736 A1    Jan. 20, 2022

Related U.S. Application Data

(63) Continuation of application No. 17/021,922, filed on Sep. 15, 2020, now Pat. No. 11,071,515, which is a
(Continued)

(51) Int. Cl.
*A61B 7/04* (2006.01)
*G06F 3/01* (2006.01)
(Continued)

(52) U.S. Cl.
CPC ............... *A61B 7/04* (2013.01); *A61B 3/113* (2013.01); *A61B 5/0077* (2013.01); *A61B 5/01* (2013.01);
(Continued)

(58) Field of Classification Search
None
See application file for complete search history.

(56) References Cited

U.S. PATENT DOCUMENTS 6,850,221 B1   2/2005   Tickle
7,979,380 B2   7/2011   Moyne et al.
(Continued)

FOREIGN PATENT DOCUMENTS

JP    2003-85289    3/2003
JP    2011-33400    2/2011
(Continued)

OTHER PUBLICATIONS

European Extended Search Report, re EP Application No. 17796709.8, dated Oct. 23, 2019.
(Continued)

*Primary Examiner* — James A Thompson
(74) *Attorney, Agent, or Firm* — Tobias Intellectual Property Law, PLLC

(57) ABSTRACT

Augmented reality systems and methods for user health analysis. Methods for user health analysis may include collecting data for an initial prediction model and continuing to collect additional data based on one or more data criteria. The methods may further include updating the initial prediction model based on the additional data to produce a revised prediction model or causing an intervention to occur based on the additional data. The data may be collected by a display system including one or more sensors configured to collect user-specific data and a display device configured to present virtual content to a user. The display device may be configured to output light with variable wavefront divergence.

20 Claims, 18 Drawing Sheets

Related U.S. Application Data continuation of application No. 15/590,922, filed on May 9, 2017, now Pat. No. 10,813,619.

(60) Provisional application No. 62/440,348, filed on Dec. 29, 2016, provisional application No. 62/366,576, filed on Jul. 25, 2016, provisional application No. 62/333,734, filed on May 9, 2016.

(51) Int. Cl.

| | |
|---|---|
| *G02B 27/01* | (2006.01) |
| *A61B 3/113* | (2006.01) |
| *A61B 5/01* | (2006.01) |
| *A61B 5/021* | (2006.01) |
| *A61B 5/145* | (2006.01) |
| *A61B 5/024* | (2006.01) |
| *A61B 5/11* | (2006.01) |
| *A61B 5/08* | (2006.01) |
| *A61B 5/318* | (2021.01) |
| *A61B 5/369* | (2021.01) |
| *A61B 5/389* | (2021.01) |
| *A61B 5/00* | (2006.01) |
| *F21V 8/00* | (2006.01) |

(52) U.S. Cl.
CPC .............. *A61B 5/021* (2013.01); *A61B 5/024* (2013.01); *A61B 5/14532* (2013.01); *A61B 5/6898* (2013.01); *G02B 27/017* (2013.01); *G02B 27/0172* (2013.01); *G06F 3/013* (2013.01); *A61B 5/0066* (2013.01); *A61B 5/0095* (2013.01); *A61B 5/082* (2013.01); *A61B 5/0816* (2013.01); *A61B 5/1116* (2013.01); *A61B 5/1123* (2013.01); *A61B 5/1128* (2013.01); *A61B 5/318* (2021.01); *A61B 5/369* (2021.01); *A61B 5/389* (2021.01); *A61B 5/441* (2013.01); *A61B 5/744* (2013.01); *A61B 2562/0219* (2013.01); *G02B 6/009* (2013.01); *G02B 6/0076* (2013.01); *G02B 2027/014* (2013.01); *G02B 2027/0112* (2013.01); *G02B 2027/0125* (2013.01); *G02B 2027/0178* (2013.01)

(56) References Cited

U.S. PATENT DOCUMENTS

| | | | |
|---|---|---|---|
| 8,248,458 B2 | 8/2012 | Schowengerdt et al. | |
| 8,950,867 B2 | 2/2015 | Macnamara | |
| 9,081,426 B2 | 7/2015 | Armstrong | |
| 9,215,293 B2 | 12/2015 | Miller | |
| 9,310,559 B2 | 4/2016 | Macnamara | |
| 9,348,143 B2 | 5/2016 | Gao et al. | |
| D758,367 S | 6/2016 | Natsume | |
| 9,417,452 B2 | 8/2016 | Schowengerdt et al. | |
| 9,470,906 B2 | 10/2016 | Kaji et al. | |
| 9,547,174 B2 | 1/2017 | Gao et al. | |
| 9,671,566 B2 | 6/2017 | Abovitz et al. | |
| 9,740,006 B2 | 8/2017 | Gao | |
| 9,791,700 B2 | 10/2017 | Schowengerdt et al. | |
| 9,846,967 B2 | 12/2017 | Schowengerdt et al. | |
| 9,851,563 B2 | 12/2017 | Gao et al. | |
| 9,857,591 B2 | 1/2018 | Welch et al. | |
| 9,874,749 B2 | 1/2018 | Bradski | |
| 10,813,619 B2 | 10/2020 | Samec et al. | |
| 11,071,515 B2 | 7/2021 | Samec et al. | |
| 2005/0216243 A1 | 9/2005 | Graham et al. | |
| 2006/0028400 A1 | 2/2006 | Lapstun et al. | |
| 2006/0028436 A1 | 2/2006 | Armstrong | |
| 2006/0074290 A1 | 4/2006 | Chen et al. | |
| 2007/0081123 A1 | 4/2007 | Lewis | |
| 2008/0117289 A1 | 5/2008 | Schowengerdt et al. | |
| 2011/0124996 A1 | 5/2011 | Reinke et al. | |
| 2012/0127062 A1 | 5/2012 | Bar-Zeev et al. | |
| 2012/0162549 A1 | 6/2012 | Gao et al. | |
| 2013/0082922 A1 | 4/2013 | Miller | |
| 2013/0117377 A1 | 5/2013 | Miller | |
| 2013/0125027 A1 | 5/2013 | Abovitz | |
| 2013/0208234 A1 | 8/2013 | Lewis | |
| 2013/0242262 A1 | 9/2013 | Lewis | |
| 2014/0039383 A1 | 2/2014 | Dobbles et al. | |
| 2014/0071539 A1 | 3/2014 | Gao | |
| 2014/0177023 A1 | 6/2014 | Gao et al. | |
| 2014/0218468 A1 | 8/2014 | Gao et al. | |
| 2014/0267420 A1 | 9/2014 | Schowengerdt | |
| 2014/0275850 A1 | 9/2014 | Venkatraman et al. | |
| 2014/0278220 A1 | 9/2014 | Yuen | |
| 2014/0306866 A1 | 10/2014 | Miller et al. | |
| 2015/0016777 A1 | 1/2015 | Abovitz et al. | |
| 2015/0103306 A1 | 4/2015 | Kaji et al. | |
| 2015/0178939 A1 | 6/2015 | Bradski et al. | |
| 2015/0205126 A1 | 7/2015 | Schowengerdt | |
| 2015/0222883 A1 | 8/2015 | Welch | |
| 2015/0222884 A1 | 8/2015 | Cheng | |
| 2015/0223731 A1 | 8/2015 | Sahin | |
| 2015/0235435 A1 | 8/2015 | Miller et al. | |
| 2015/0262425 A1 | 9/2015 | Hastings et al. | |
| 2015/0268415 A1 | 9/2015 | Schowengerdt et al. | |
| 2015/0302250 A1 | 10/2015 | Miller | |
| 2015/0302652 A1 | 10/2015 | Miller et al. | |
| 2015/0302657 A1 | 10/2015 | Miller | |
| 2015/0302663 A1 | 10/2015 | Miller | |
| 2015/0309263 A2 | 10/2015 | Abovitz et al. | |
| 2015/0309316 A1 | 10/2015 | Osterhout et al. | |
| 2015/0326570 A1 | 11/2015 | Publicover et al. | |
| 2015/0346490 A1 | 12/2015 | TeKolste et al. | |
| 2015/0346495 A1 | 12/2015 | Welch et al. | |
| 2015/0379400 A1 | 12/2015 | Tatourian | |
| 2016/0011419 A1 | 1/2016 | Gao | |
| 2016/0018654 A1 | 1/2016 | Haddick et al. | |
| 2016/0026253 A1 | 1/2016 | Bradski et al. | |
| 2016/0077547 A1 | 3/2016 | Aimone et al. | |
| 2016/0235374 A1 | 8/2016 | Miller et al. | |
| 2016/0270656 A1 | 9/2016 | Samec et al. | |
| 2017/0276948 A1 | 9/2017 | Welch et al. | |
| 2017/0323485 A1 | 11/2017 | Samec et al. | |
| 2017/0365048 A1* | 12/2017 | Hamilton, II | G16Z 99/00 |
| 2018/0032130 A1* | 2/2018 | Meglan | A61B 34/25 |
| 2020/0405257 A1 | 12/2020 | Samec | |

FOREIGN PATENT DOCUMENTS

| | | |
|---|---|---|
| KR | 2014-0066258 | 5/2014 |
| KR | 2016-0034199 | 3/2016 |
| WO | 2012081194 A1 | 6/2012 |
| WO | WO 2012/154278 | 11/2012 |
| WO | WO 2013/049248 | 4/2013 |
| WO | 2013188464 A1 | 12/2013 |
| WO | 2014164901 A1 | 10/2014 |
| WO | 2015095172 A1 | 6/2015 |
| WO | WO 2015/117039 | 8/2015 |
| WO | WO 2015/173388 | 11/2015 |
| WO | WO 2017/196879 | 11/2017 |

OTHER PUBLICATIONS

International Search Report and Written Opinion for PCT Application No. PCT/US2017/031806, dated Jul. 17, 2017.

International Preliminary Report on Patentability for PCT Application No. PCT/US2017/031806, dated Nov. 13, 2018.

Anthony, S., "MIT releases open-source software that reveals invisible motion and detail in video", Extreme Tech, Feb. 28, 2013, as accessed Aug. 4, 2017, in 5 pages.

ARToolKit: https://web.archive.org/web/20051013062315/http://www.hitl.washington.edu:80/artoolkit/documentation/hardware.htm, archived Oct. 13, 2005.

Azuma, "A Survey of Augmented Reality," Teleoperators and Virtual Environments 6, 4 (Aug. 1997), pp. 355-385. https://web.archive.org/web/20010604100006/http://www.cs.unc.edu/~azuma/ARpresence.pdf.

(56) References Cited

OTHER PUBLICATIONS

Azuma, "Predictive Tracking for Augmented Realty," TR95-007, Department of Computer Science, UNC-Chapel Hill, NC, Feb. 1995.

Bimber, et al., "Spatial Augmented Reality—Merging Real and Virtual Worlds," 2005 https://web.media.mit.edu/~raskar/book/BimberRaskarAugmentedRealityBook.pdf.

Jacob, "Eye Tracking in Advanced Interface Design," Human-Computer Interaction Lab Naval Research Laboratory, Washington, D.C. / paper/ in Virtual Environments and Advanced Interface Design, ed. by W. Barfield and T.A. Furness, pp. 258-288, Oxford University Press, New York (1995).

Tanriverdi and Jacob, "Interacting With Eye Movements in Virtual Environments," Department of Electrical Engineering and Computer Science, Tufts University, Medford, MA—paper/Proc. ACM CHI 2000 Human Factors in Computing Systems Conference, pp. 265-272, Addison-Wesley/ACM Press (2000).

Wikipedia: "Glanzfeld effect", Wikipedia, printed Oct. 20, 2017, in 2 pages; URL: https://en.wikipedia.org/wiki/Ganzfeld__effect.

Wikipedia: "Human echolocation", Wikipedia, printed Oct. 20, 2017, in 8 pages. URL: https://en.wikipedia.org/wiki/Human_echolocation.

Office Action dated Jan. 25, 2023 for JP App. No. 2022-015504.

* cited by examiner

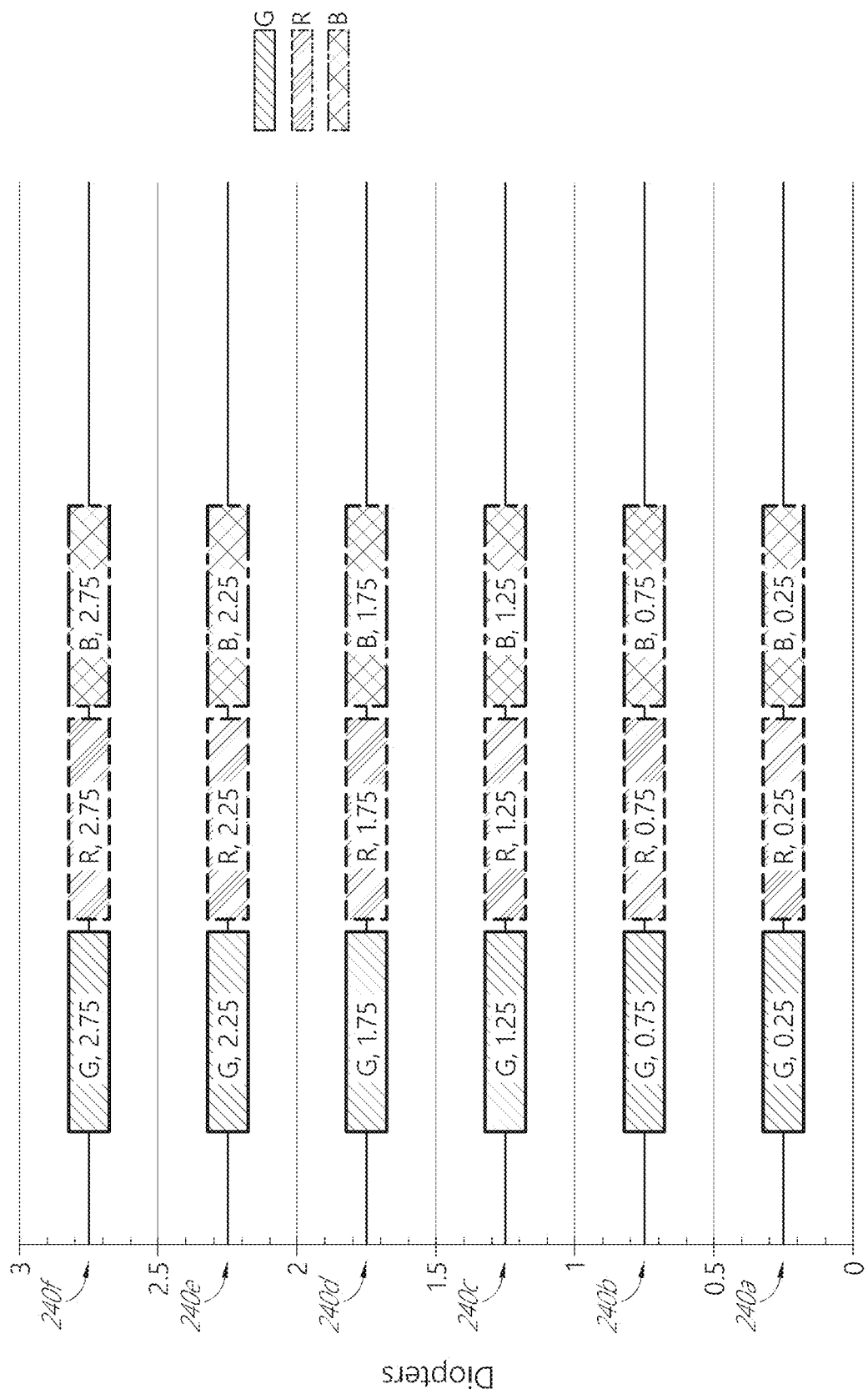

AUGMENTED REALITY SYSTEMS AND METHODS FOR USER HEALTH ANALYSIS

PRIORITY CLAIM

This application is a continuation of U.S. application Ser. No. 17/021,922, filed on Sep. 15, 2020, entitled "AUGMENTED REALITY SYSTEMS AND METHODS FOR USER HEALTH ANALYSIS," which is a continuation of U.S. application Ser. No. 15/590,922 filed on May 9, 2017, ENTITLED "AUGMENTED REALITY SYSTEMS AND METHODS FOR USER HEALTH ANALYSIS," which claims the benefit of priority under 35 U.S.C. § 119(e) of U.S. Provisional Application No. 62/333,734 filed on May 9, 2016; U.S. Provisional Application No. 62/366,576 filed on Jul. 25, 2016; and U.S. Provisional Application No. 62/440,348 filed on Dec. 29, 2016. The entire disclosure of each of these priority documents is incorporated herein by reference.

INCORPORATION BY REFERENCE

This application incorporates by reference the entirety of each of the following patent applications: U.S. application Ser. No. 14/555,585 filed on Nov. 27, 2014, published on Jul. 23, 2015 as U.S. Publication No. 2015/0205126; U.S. application Ser. No. 14/690,401 filed on Apr. 18, 2015, published on Oct. 22, 2015 as U.S. Publication No. 2015/0302652; U.S. application Ser. No. 14/212,961 filed on Mar. 14, 2014, now U.S. Pat. No. 9,417,452 issued on Aug. 16, 2016; U.S. application Ser. No. 14/331,218 filed on Jul. 14, 2014, published on Oct. 29, 2015 as U.S. Publication No. 2015/0309263; U.S. application Ser. No. 15/072,290 filed on Mar. 16, 2016, published on Sep. 22, 2016 as U.S. Publication No. 2016/0270656; and U.S. application Ser. No. 15/469,369 filed on Mar. 24, 2017.

BACKGROUND

Field

The present disclosure relates to display systems and, more particularly, to augmented reality display systems.

Description of the Related Art

Modern computing and display technologies have facilitated the development of systems for so called "virtual reality" or "augmented reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user. A mixed reality, or "MR", scenario is a type of AR scenario and typically involves virtual objects that are integrated into, and responsive to, the natural world. For example, in an MR scenario, AR image content may be blocked by or otherwise be perceived as interacting with objects in the real world.

Referring to FIG. 1, an augmented reality scene 10 is depicted wherein a user of an AR technology sees a real-world park-like setting 20 featuring people, trees, buildings in the background, and a concrete platform 30. In addition to these items, the user of the AR technology also perceives that he "sees" "virtual content" such as a robot statue 40 standing upon the real-world platform 30, and a cartoon-like avatar character 50 flying by which seems to be a personification of a bumble bee, even though these elements 40, 50 do not exist in the real world. Because the human visual perception system is complex, it is challenging to produce an AR technology that facilitates a comfortable, natural-feeling, rich presentation of virtual image elements amongst other virtual or real-world imagery elements.

Systems and methods disclosed herein address various challenges related to AR and VR technology.

SUMMARY

In some embodiments, a display system comprises a display device configured to present virtual content to a user, one or more sensors attached to the display device and configured to collect user-specific data, one or more processors, and one or more computer storage media. The display device is configured to output light with variable wavefront divergence. The one or more computer storage media store instructions that, when executed by the system, cause the system to perform operations comprising collecting data from the one or more sensors, applying the data to an initial prediction model, continuing to collect additional data from the one or more sensors, and updating the initial prediction model based on the additional data to produce a revised prediction model.

In some other embodiments, a method of conducting a user health analysis comprises collecting data from one or more sensors of an augmented reality display device configured to output light with variable wavefront divergence, applying the data to an initial prediction model, continuing to collect additional data from the one or more sensors, and updating the initial prediction model based on the additional data to produce a revised prediction model.

In yet other embodiments, a display system comprises a display device configured to present virtual content to a user, one or more sensors attached to the display device and configured to collect user-specific data, one or more processors, and one or more computer storage media. The display device is configured to output light with variable wavefront divergence. The one or more computer storage media store instructions that, when executed by the system, cause the system to perform operations comprising collecting data from the one or more sensors, applying the data to an initial prediction model, continuing to collect additional data from the one or more sensors, and causing an intervention to occur based on the additional data.

In some other embodiments, a method of conducting a user health analysis comprises collecting data from one or more sensors of an augmented reality display device configured to output light with variable wavefront divergence, applying the data to an initial prediction model, continuing to collect additional data from the one or more sensors, and causing an intervention to occur based on the additional data.

In yet other embodiments, a display system comprises a head-mounted display configured to project light to a user to display augmented reality image content on a plurality of depth planes. The display comprises one or more waveguides configured to project the light to the user. The one or more waveguides are further configured to transmit light from a surrounding environment to the user. The system also comprises one or more sensors configured to continuously collect user-specific data of the user over 3 or more hours while the user wears the display.

In some other embodiments, a display system comprises a head-mounted display configured to project light to a user to display augmented reality image content on a plurality of depth planes. The display comprises one or more waveguides configured to project the light to the user. The one or more waveguides are further configured to transmit light from a surrounding environment to the user. The display system further comprises one or more environmental sensors configured to detect environmental data; and/or one or more user sensors configured to continuously collect user-specific data of the user over 3 more hours while the user wears the display. The display system is configured to correlate the environmental data with the user-specific data.

In yet other embodiments, a display system comprises a head-mounted display configured to project light to a user to display image content on a plurality of depth planes. The display comprises one or more waveguides configured to project the light to the user. The one or more waveguides are configured to project the light with varying amounts of divergence depending upon a depth plane for the image content formed by the light. The display system further comprises one or more sensors configured to continuously collect user-specific data of the user over 3 or more hours. The display system is configured to conduct an analysis of the user based on the user-specific data.

In some other embodiments, a display system comprises a head-mounted display configured to project light to a user to display image content on a plurality of depth planes. The display comprises one or more waveguides configured to project light to the user. The one or more waveguides are configured to transmit light from a surrounding environment to the user. The display system further comprises one or more environmental sensors configured to detect environmental data; and one or more sensors configured to collect user-specific data of the user. The display system is configured to administer a treatment to the user, and is further configured to administer or modify the treatment based on the environmental or user-specific data.

In yet other embodiments, a display system comprises a head-mounted display configured to project light to a user to display image content on a plurality of depth planes. The display system comprises one or more waveguides configured to project light to the user. The one or more waveguides are configured to transmit light from a surrounding environment to the user. The display system further comprises one or more environmental sensors configured to detect environmental data; and one or more user-worn sensors configured to continuously collect user-specific data of the user over 3 or more hours. In addition, the display system is configured to share one or both of the user-worn and/or environmental data with other display systems.

In some other embodiments, a display system comprises a head-mounted display configured to project light to a user to display image content on a plurality of depth planes. The display system comprises one or more waveguides configured to project light to the user. The one or more waveguides are configured to transmit light from a surrounding environment to the user. The display system is configured to provide visual content to the user with a mismatched accommodation-vergence relationship.

In yet other embodiments, a display system comprises a head-mounted display configured to project light to a user to display image content on a plurality of depth planes. The display system comprises one or more waveguides configured to project light to the user. The one or more waveguides are configured to transmit light from a surrounding environment to the user. The display system further comprises an environmental sensor, such as a microphone or pressure sensor, configured to detect sound reflected from the ambient environment. In addition, the display system is configured to conduct echolocation using an environmental sensor to determine one or both of a size and distance of an object in the ambient environment. In some embodiments, the display system may further comprise an environmental sensor to detect light in the surrounding environment, such as an imaging device.

In some embodiments, a display system comprises a head-mounted display configured to project light to a user to display augmented reality image content on a plurality of depth planes. The display comprises one or more waveguides configured to project the light to the user. The one or more waveguides are further configured to transmit light from a surrounding environment to the user. The system also comprises a sensor configured to collect a plurality of sets of user-specific data of the user while the user wears the display. The display system is configured to conduct a plurality of user analyses using distinct sets of the collected user-specific data for each of the analyses.

In some other embodiments, a display system comprises a head-mounted display configured to project light to a user to display augmented reality image content on a plurality of depth planes. The display comprises one or more waveguides configured to project the light to the user. The one or more waveguides are further configured to transmit light from a surrounding environment to the user. The display system further comprises one or more environmental sensors configured to detect environmental data; and/or one or more user sensors configured to collect a plurality of sets of user-specific data of the user while the user wears the display. The display system is configured to correlate the environmental data with the user-specific data.

In yet other embodiments, a display system comprises a head-mounted display configured to project light to a user to display image content on a plurality of depth planes. The display comprises one or more waveguides configured to project the light to the user. The one or more waveguides are configured to project the light with varying amounts of divergence depending upon a depth plane for the image content formed by the light. The display system further comprises one or more sensors configured to collect a plurality of sets of user-specific data of the user. The display system is configured to conduct a plurality of user analyses using distinct sets of the collected user-specific data for each of the analyses.

In some other embodiments, a display system comprises a head-mounted display configured to project light to a user to display image content on a plurality of depth planes. The display comprises one or more waveguides configured to project light to the user. The one or more waveguides are configured to transmit light from a surrounding environment to the user. The display system further comprises one or more environmental sensors configured to detect environmental data; and/or one or more sensors configured to collect user-specific data of the user. The display system is configured to administer a treatment to the user, and is further configured to administer or modify the treatment based on a correlation between the environmental and the user-specific data.

In yet other embodiments, a display system comprises a head-mounted display configured to project light to a user to display image content on a plurality of depth planes. The display system comprises one or more waveguides configured to project light to the user. The one or more waveguides are configured to transmit light from a surrounding environment to the user. The display system further comprises one or more environmental sensors configured to detect environmental data; and one or more user-worn sensors configured to collect user-specific data of the user. In addition, the display system is configured to share one or both of the user-specific and environmental data with other display systems.

Additional example embodiments are provided below.

1. A display system comprising:
  a head-mounted display configured to project light to a user to display augmented reality image content on a plurality of depth planes, the display comprising:
    one or more waveguides configured to project the light to the user,
    wherein the one or more waveguides are further configured to transmit light from a surrounding environment to the user; and
  at least one sensor configured to continuously collect user-specific data of the user over 3 or more hours while the user wears the display.

2. The display system of Embodiment 1, wherein the display system is configured to conduct an analysis of the user based on the user-specific data.

3. The display system of Embodiment 2, wherein the analysis is a diagnostic health analysis.

4. The display system of Embodiment 2, wherein the analysis is associated with a recommendation for intervention.

5. The display system of Embodiment 1, wherein the display system is configured to conduct an analysis of the user based on the user-specific data 6. The display system of Embodiment 1, wherein the sensor is configured to collect the user-specific data over 5 or more hours.

7. The display system of Embodiment 1, wherein the sensor is configured to collect the user-specific data multiple times a day, for multiple days.

8. The display system of Embodiment 1, wherein the display system is configured to discount outlying user-specific data points during the analysis.

9. The display system of Embodiment 1, wherein the sensor is an imaging device configured to image the user.

10. The display system of Embodiment 9, wherein the imaging device is configured to image one or more of an eye of the user and features surrounding the eye.

11. The display system of Embodiment 1, wherein the display system is configured to conduct a health analysis by:
  delivering augmented reality content to the user; and
  collecting the user-specific data in response to the delivered augmented reality content.

12. The display system of Embodiment 11, wherein the augmented reality content is augmented reality image content displayed on the head-mounted display.

13. The display system of Embodiment 11, wherein the augmented reality content comprises sounds.

14. The display system of Embodiment 11, further comprising analyzing the collected user-specific data to determine a correlation between the user-specific data and the displaying augmented reality image content.

15. The display system of Embodiment 1, wherein the sensor and the display are connected to a common frame, further comprising one or more additional sensors connected to the frame, wherein the one or more additional sensors are configured to continuously collect additional user-specific data of the user over the 3 or more hours, wherein the display system is configured to correlate the user-specific data and the additional user-specific data.

16. The display system of Embodiment 1, wherein the sensor is selected from the group consisting of an eye tracking device, an electro-diagnostic device, a blood pressure sensor, a blood glucose meter, a temperature sensor, an accelerometer, a heart rate monitor, a camera, and a microphone.

17. The display system of Embodiment 1, wherein further comprising a local processor and data module, wherein the sensor is configured to communicate wirelessly with the local processor and data module.

18. The display system of Embodiment 1, wherein the display comprises a waveguide stack comprising a plurality of the waveguides.

19. The display system of Embodiment 1, wherein the display system comprises a plurality of the sensors.

20. The display system of Embodiment 1, wherein the display system is configured to conduct a health analysis on the user, wherein the health analysis comprises one or more of:
  evaluating a function of a nervous system of the user;
  determining a mental status of the user;
  detecting a physiological or behavioral manifestation of a mental or neurological disorder;
  detecting a mood; and
  evaluating a sensory function of the user.

21. A display system comprising:
  a head-mounted display configured to project light to a user to display augmented reality image content on a plurality of depth planes, the display comprising:
    one or more waveguides configured to project the light to the user,
    wherein the one or more waveguides are further configured to transmit light from a surrounding environment to the user;
    an environmental sensor configured to detect environmental data; and
    a user sensor configured to continuously collect user-specific data of the user over 3 or more hours while the user wears the display,
  wherein the display system is configured to correlate the environmental data with the user-specific data.

22. The display system of Embodiment 21, wherein the display system is configured to conduct an analysis of the user based on the user-specific data, wherein correlating the environmental data with the user-specific data comprises correlating a result of the analysis with the user-specific data.

23. The display system of Embodiment 21, wherein the user-specific data comprises behavioral information characterizing the behavior of the user.

24. The display system of Embodiment 21, wherein the behavior information comprises one or more of movements of the user and facial expressions the user.

25. The display system of Embodiment 21, wherein the display system is configured to analyze the data and display augmented reality image content comprising information regarding the surrounding environment.

26. The display system of Embodiment 21, wherein the head-mounted display is configured to present augmented reality content to the user, wherein the environmental data comprises information regarding the augmented reality content.

27. A display system comprising:
  a head-mounted display configured to project light to a user to display image content on a plurality of depth planes, the display comprising:

one or more waveguides configured to project the light to the user,
wherein the one or more waveguides are configured to project the light with varying amounts of divergence depending upon a depth plane for the image content formed by the light; and
a sensor configured to continuously collect user-specific data of the user over 3 or more hours,
wherein the display system is configured to conduct an analysis of the user based on the user-specific data.

28. The display system of Embodiment 27, wherein the sensor and the display are connected to a common frame, further comprising one or more additional sensors connected to the frame, wherein the one or more additional sensors are configured to continuously collect additional user-specific data of the user over the 3 or more hours, wherein the analysis comprises correlating the user-specific data and the additional user-specific data.

29. A display system comprising:
a head-mounted display configured to project light to a user to display image content on a plurality of depth planes, the display comprising:
one or more waveguides configured to project light to the user,
wherein the one or more waveguides are configured to transmit light from a surrounding environment to the user;
an environmental sensor configured to detect environmental data; and
a sensor configured to collect user-specific data of the user,
wherein the display system is configured to administer a treatment to the user, and wherein the display system is further configured to administer or modify the treatment based on the environmental or user-specific data.

30. The display system of Embodiment 29, wherein the treatment comprises visual content configured to treat one or more mental, behavioral, and/or neurological disorder.

31. The display system of Embodiment 29, wherein the display system is configured to administer a treatment to the user in response to detecting a medical sign or symptom experienced by the wearer.

32. The display system of Embodiment 29, wherein the display system is configured to modify the treatment based upon the user-specific data exceeding or remaining below predetermined threshold levels.

33. A display system comprising:
a head-mounted display configured to project light to a user to display image content on a plurality of depth planes, the display comprising:
one or more waveguides configured to project light to the user,
wherein the one or more waveguides are configured to transmit light from a surrounding environment to the user;
an environmental sensor configured to detect environmental data; and
user-worn sensors configured to continuously collect user-specific data of the user over 3 or more hours,
wherein the display system is configured to share one or both of the user-specific and environmental data with other display systems.

34. The display system of Embodiment 33, further comprising wireless communication circuitry configured to transmit and receive environmental data and user-specific data between display system worn by different users.

35. The display system of Embodiment 33, wherein the display system is configured to transmit the environmental or user-specific data when abnormal environmental or user-specific data are detected.

36. The display system of Embodiment 33, wherein the display system is configured to transmit environmental data and user-specific data between display systems worn by different users.

37. The display system of Embodiment 33, wherein the display system is further configured to receive environmental or user-specific data sent from at least one other system, and compare the received environmental or user-specific data with environmental data detected with the environmental sensor or user-specific data detected with the user-worn sensor.

38. The display system of Embodiment 37, wherein the at least one other system comprises another display system.

39. The display system of Embodiment 33, comprising:
processing circuitry configured to receive environmental data, and user-specific data transmitted from other display systems,
wherein the processing circuitry is further configured to detect an occurrence of similar physiological, behavioral, or environmental abnormalities in a plurality of display device wearers in physical proximity based on location data and at least one of the received environmental data or the received user-specific data.

40. The display system of Embodiment 33, wherein at least one of the different users is a clinician, and wherein the display system worn by the clinician is configured to display augmented reality content to the clinician for diagnosis, monitoring, or treatment of a different user.

41. A display system comprising:
a head-mounted display configured to project light to a user to display image content on a plurality of depth planes, the display comprising:
one or more waveguides configured to project light to the user,
wherein the one or more waveguides are configured to transmit light from a surrounding environment to the user;
wherein the display system is configured to:
provide visual content to the user with a mismatched accommodation-vergence relationship.

42. The display system of Embodiment 41, further comprising:
an environmental sensor configured to detect environmental data; and
user-worn sensors configured to continuously collect user-specific data of the user over 3 or more hours.

43. The display system of Embodiment 41, wherein the display system is further configured to collect user data comprising one or more physiological or behavioral responses.

44. The display system of Embodiment 43, wherein the physiological or behavioral responses comprise electrical activity in the brain.

45. The display system of embodiment 42, wherein the physiological or behavior responses comprise one or more autonomic responses.

46. The display system of Embodiment 44, wherein the one or more autonomic responses comprise one or more of blood pressure, breath rate, and pupil dilation/contraction.

47. The display system of Embodiment 40, wherein the display system is configured to provide content to the user with one or more selected mismatches selected from the group consisting of audiovisual mismatches, vestibulo-ocular mismatches, and proprioceptive visual mismatches.

48. A display system comprising:
a head-mounted display configured to project light to a user to display image content on a plurality of depth planes, the display comprising:
one or more waveguides configured to project light to the user,
wherein the one or more waveguides are configured to transmit light from a surrounding environment to the user; and
an environmental sensor configured to detect sound reflected from the ambient environment,
wherein the display system is configured to conduct echolocation using an environmental sensor to determine one or both of a size and distance of an object in the ambient environment.

49. The display system of Embodiment 48, further comprising a sound emitter configured to project sound into the ambient environment, wherein the display system is configured to conduct echolocation based upon an initial generation of the sound and an elapsed time between that initial generation and the detection of the reflection by the environmental sensor.

50. The display system of Embodiment 48, wherein the display system is configured to conduct echolocation based upon an elapsed time between detection of a sound generated by the user, and the detection of the reflection of the sound by the environmental sensor.

51. A display system comprising:
a head-mounted display configured to project light to a user to display augmented reality image content on a plurality of depth planes, the display comprising:
one or more waveguides configured to project the light to the user, wherein the one or more waveguides are further configured to transmit light from a surrounding environment to the user; and
a sensor configured to collect a plurality of sets of user-specific data of the user while the user wears the display,
wherein the display system is configured to conduct a plurality of user analyses using distinct sets of the collected user-specific data for each of the analyses.

52. The display system of Embodiment 51, wherein the user analyses comprise a diagnostic health analysis.

53. The display system of Embodiment 51, wherein the user analyses comprise a therapeutic analysis.

54. The display system of Embodiment 51, wherein the display system is configured to discount outlying user-specific data points during the analysis.

55. The display system of Embodiment 51, wherein the sensor is an imaging device configured to image the user.

56. The display system of Embodiment 55, wherein the imaging device is configured to image one or more of an eye of the user and features surrounding the eye.

57. The display system of Embodiment 51, wherein the display system is configured to conduct a health analysis by:
detecting a stimulus in the world around the user; and
collecting the user-specific data in response to the detected stimulus.

58. The display system of Embodiment 57, wherein detecting a stimulus comprises determining that the user is touching an object.

59. The display system of Embodiment 57, wherein detecting a stimulus comprises detecting a sound audible to the user.

60. The display system of Embodiment 57, further comprising analyzing the collected user-specific data to determine a correlation between the user-specific data and the detected stimulus.

61. The display system of Embodiment 51, wherein the sensor and the display are connected to a common frame, further comprising one or more additional sensors connected to the frame, wherein the sensor and the one or more additional sensors are configured to collect different ones of the sets of the user-specific data.

62. The display system of Embodiment 60, wherein the display system is configured to collect a statistically significant amount of data in each data set.

63. The display system of Embodiment 51, wherein the sensor is selected from the group consisting of an eye tracking device, an electro-diagnostic device, a blood pressure sensor, a blood glucose meter, a temperature sensor, an accelerometer, a heart rate monitor, a camera, and a microphone.

64. The display system of Embodiment 51, further comprising a local processor and data module, wherein the sensor is configured to communicate wirelessly with the local processor and data module.

65. The display system of Embodiment 51, wherein the display comprises a waveguide stack comprising a plurality of the waveguides.

66. The display system of Embodiment 51, wherein the display system comprises a plurality of the sensors.

67. The display system of Embodiment 51, wherein the display system is configured to conduct a health analysis on the user, wherein the health analysis comprises one or more of:
evaluating a function of one or more cranial nerves of the user; determining a mental status of the user;
detecting a behavioral disorder;
detecting a mood;
detecting an obsessive-compulsive disorder; and
evaluating a sensory function of the user.

68. A display system comprising:
a head-mounted display configured to project light to a user to display augmented reality image content on a plurality of depth planes, the display comprising:
one or more waveguides configured to project the light to the user, wherein the one or more waveguides are further configured to transmit light from a surrounding environment to the user;
an environmental sensor configured to detect environmental data; and
a user sensor configured to collect a plurality of sets of user-specific data of the user while the user wears the display,
wherein the display system is configured to correlate the environmental data with the user-specific data.

69. The display system of Embodiment 68, wherein the environmental data comprises data regarding or more of the augmented reality image content and data from one or more external databases.

70. The display system of Embodiment 68, wherein the display system is configured to conduct an analysis of the user based on the user-specific data, wherein correlating the environmental data with the user-specific data comprises correlating a result of the analysis with the user-specific data.

71. The display system of Embodiment 68, wherein the user-specific data comprises behavioral information characterizing the behavior of the user.

72. The display system of Embodiment 68, wherein the behavior information comprises one or more of movements of the user and facial expressions the user.

73. The display system of Embodiment 68, wherein the display system is configured to analyze the data and display augmented reality image content comprising information regarding the surrounding environment.

74. The display system of Embodiment 68, wherein the display system is configured to detect a plurality of stimuli in the surrounding environment based on the environmental data.

75. A display system comprising:
a head-mounted display configured to project light to a user to display image content on a plurality of depth planes, the display comprising:
one or more waveguides configured to project the light to the user, wherein the one or more waveguides are configured to project the light with varying amounts of divergence depending upon a depth plane for the image content formed by the light; and
a sensor configured to collect a plurality of sets of user-specific data of the user,
wherein the display system is configured to conduct a plurality of user analyses using distinct sets of the collected user-specific data for each of the analyses.

76. The display system of Embodiment 75, wherein the sensor and the display are connected to a common frame, further comprising one or more additional sensors connected to the frame, wherein the sensor and the one or more additional sensors are configured to collect different ones of the sets of the user-specific data.

77. A display system comprising:
a head-mounted display configured to project light to a user to display image content on a plurality of depth planes, the display comprising:
one or more waveguides configured to project light to the user, wherein the one or more waveguides are configured to transmit light from a surrounding environment to the user;
an environmental sensor configured to detect environmental data; and a sensor configured to collect user-specific data of the user,
wherein the display system is configured to administer a treatment to the user, and wherein the display system is further configured to administer or modify the treatment based on a correlation between the environmental data and the user-specific data.

78. The display system of Embodiment 77, wherein the treatment comprises visual content configured to treat one or more of epilepsy, obsessive compulsive behavior, an anxiety disorder, and depression.

79. The display system of Embodiment 77, wherein the display system is configured to administer a treatment to the user in response to detecting a medical sign or symptom experienced by the wearer.

80. The display system of Embodiment 79, wherein the display system is configured to modify the treatment based upon the user-specific data exceeding or remaining below predetermined threshold levels.

81. A display system comprising:
a head-mounted display configured to project light to a user to display image content on a plurality of depth planes, the display comprising:
one or more waveguides configured to project light to the user, wherein the one or more waveguides are configured to transmit light from a surrounding environment to the user;
an environmental sensor configured to detect environmental data; and
user-worn sensors configured to collect user-specific data of the user,
wherein the display system is configured to share one or both of the user-specific and environmental data with other display systems.

82. The display system of Embodiment 81, further comprising wireless communication circuitry configured to transmit and receive environmental data and user-specific data between display systems worn by different users.

83. The display system of Embodiment 81, wherein the display system is configured to transmit the environmental or user-specific data when abnormal environmental or user-specific data are detected.

84. The display system of Embodiment 81, wherein the display system is configured to transmit environmental data and user-specific data between display systems worn by different users.

85. The display system of Embodiment 81, wherein the display system is further configured to receive environmental or user-specific data sent from at least one other display system, and compare the received environmental or user-specific data with environmental data detected with the environmental sensor or user-specific data detected with the user-worn sensor.

86. The display system of Embodiment 81, comprising:
processing circuitry configured to receive environmental data, and user-specific data transmitted from other display systems,
wherein the processing circuitry is further configured to detect an occurrence of similar physiological, behavioral, or environmental abnormalities in a plurality of display device wearers in physical proximity based on location data and at least one of the received environmental data or the received user-specific data.

87. The display system of Embodiment 81, wherein at least one of the different users is a clinician, and wherein the display system worn by the clinician is configured to display augmented reality content to the clinician for diagnosis, monitoring, or treatment of a different user.

88. A display system comprising:
a head-mounted display configured to project light to a user to display image content on a plurality of depth planes, the display comprising:
one or more waveguides configured to project light to the user, wherein the one or more waveguides are configured to transmit light from a surrounding environment to the user; and
an environmental sensor configured to detect sound reflected from the ambient environment,
wherein the display system is configured to conduct echolocation using an environmental sensor to determine one or both of a size and distance of an object in the ambient environment.

89. The display system of Embodiment 88, further comprising a sound emitter configured to project sound into the ambient environment, wherein the display system is configured to conduct echolocation based upon an initial generation of the sound and an elapsed time between that initial generation and the detection of the reflection by the environmental sensor.

90. The display system of Embodiment 88, wherein the display system is configured to conduct echolocation based upon an elapsed time between detection of a sound generated by the user, and the detection of the reflection of the sound by the environmental sensor.

91. The display system of Embodiment 88, wherein the display system is configured to determine one or more stimuli of the ambient environment based on the echolocation.

92. The display system of Embodiment 91, further comprising one or more user-worn sensors configured to collect user-specific data from the user, wherein the display system is further configured to determine a correlation between the collected user-specific data and the stimuli of the ambient environment.

BRIEF DESCRIPTION OF THE DRAWINGS

FIG. 8 illustrates an example of a stacked waveguide assembly in which each depth plane includes images formed using multiple different component colors.

Figure 1:
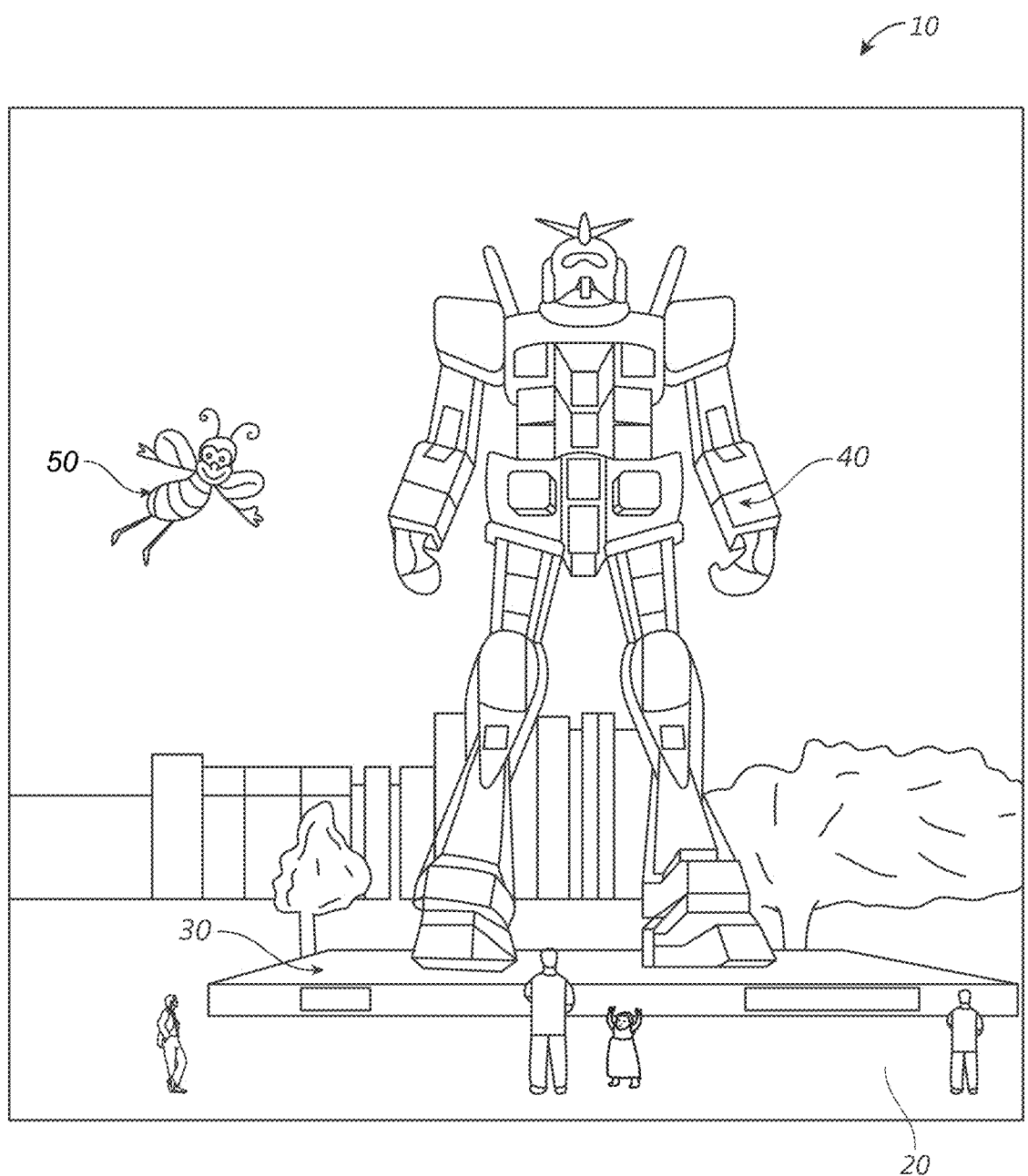
FIG. 1 illustrates a user's view of augmented reality (AR) through an AR device.

The drawings are provided to illustrate example embodiments and are not intended to limit the scope of the disclosure.

DETAILED DESCRIPTION

As disclosed herein, augmented reality (AR) and mixed reality (MR) systems may display virtual content to a viewer, or user, while still allowing the viewer to see the world around them. Preferably, this content is displayed on a head-mounted display, e.g., as part of eyewear, that projects image information to the viewer's eyes, while also transmitting light from the surrounding environment to those eyes, to allow a view of that surrounding environment. As used herein, it will be appreciated that a "head-mounted" display is a display that may be mounted on the head of a viewer.

As discussed herein, many VR, AR, and MR display devices suffer from an accommodation-vergence mismatch and/or vestibulo-ocular mismatch when displaying image information. Such a mismatch may cause user discomfort and may make long-term wear of the device infeasible. Advantageously, display devices according to embodiments herein allow for long-term wear of the device by among other things, providing a correct match between accommodation and vergence, and/or between vestibular and ocular input, in the user. In some embodiments, display systems disclosed herein present images to the viewer with an accommodation-vergence mismatch of about 0.5 diopter or less, about 0.33 diopter or less, or about 0.25 diopter or less, including about 0.1 diopter or less. As a result, users of the device may be able to wear and use the device substantially continuously for durations of about 3 hours or more, about 4 hours or more, about 5 hours or more, about 6 hours or more, or all day, without removing the device for more than about 25%, more than about 20%, more than about 15%, more than about 10%, or more than about 5% of the duration.

The wearability of display systems disclosed herein and the long-term nature of that wearability, coupled with the close proximity of the display system (including sensory components) to the viewer, provide advantageously opportunities for providing healthcare benefits. For example, the display systems may allow the gathering of sets of data that may not otherwise be easily obtained. In addition, the accuracy of assessment and prediction of user states and conditions may increase due to the duration of the data collection, the variety of the data, the variety of locations of the data collection, and the ability to collect multiple types of data simultaneously (thereby allowing different data to be cross-referenced, e.g., using time stamps and/or location stamps applied to all of the data), among other benefits, may increase the accuracy of any health analysis performed using user data or external data, e.g., environmental data, and may reveal relationships between health conditions or treatments and various measured variables that are otherwise not readily apparent. It will be appreciated that external data may describe properties or conditions that are external to the user.

In some embodiments, user sensors forming part of the display system may be configured to collect data over an extended duration, while the display system is mounted on the viewer during substantially all of that duration. Preferably, the duration of about 3 hours or more, about 4 hours or more, about 5 hours or more, about 6 hours or more, or about a full day or more, all without removing the device for more than about 25%, more than about 20%, more than about 15%, more than about 10%, or more than about 5% of the specified duration. In addition to the user sensors, environmental sensors form part of the display system and may be configured to collect data regarding the user's ambient environment. In various embodiments, the user sensors may be configured to collect data until a predefined criterion or set of criteria is met, including the criterion of establishing statistically significant or otherwise useful correlations between the user data and environment data independent of the duration for which the system is worn. For example, some analyses may be accomplished based on wearing the system for less than an hour, less than three hours, or intermittently for short or long durations.

In some embodiments, virtual, or AR, content (e.g., images, haptic feedback, and/or sounds) may be provided to the user and the user sensors may collect user data in response to this virtual content. In such embodiments, the virtual content may have associated "environmental data," or virtual data, corresponding to the data that would be collected by environmental sensors if the AR image content were, e.g., a real object or real sound.

In various embodiments, user data, or user-specific data, is collected, e.g., from sensors of the display system. User-specific data may include physiological data (e.g., heart rate, blood pressure, brain waves, etc.) and/or behavioral data (e.g., body position, limb movement, facial expression, eye movements, etc.). In some embodiments, user-specific data includes parameters derived from a plurality of the physiological and/or behavioral data. Such parameters may be referred to as derived parameters, an example of which is emotional state. In some embodiments, the user-specific data is gathered from obtrusive or unobtrusive objective measurement instruments (e.g., a user-worn heart rate sensor, etc.), or from subjective measurement instruments (e.g., digital self-reporting and/or other-report tools, such as Ecological Momentary Assessment or the like).

In various embodiments, external data is collected, e.g., by direct measurement using sensors of the display system and/or by obtaining the data from external sources, such as external databases. External data may include environmental data (e.g., ambient light, proximate objects, etc.), including virtual data, and public/general data (e.g., weather information, pollen count, etc.).

In some embodiments, interventions may be administered to a user. Interventions may include treatments, such as various medical and/or psychological treatments. Interventions and/or treatments may be administered or modified based on any one or more of user-specific data and external data, as well as based on a correlation or other analysis of one or more data types.

In some embodiments, correlation analyses may be conducted to determine relationships between two or more different types of data. For instance, the user-specific and environmental data are correlated to determine relationships between the two types of data. Advantageously, the correlation may be made stronger or may be more accurately determined due to the ability to obtain the data in many different contexts (e.g., different locations, times, etc.). Correlation between user-specific and environmental data may include various statistical analyses performed on data sets obtained from various sources (e.g., environmental data and user-specific data) for various purposes, for example, assessing meaningful statistical correlational and/or causal relationships between data types and/or data sources, and building analytical and/or predictive regression for individuals and/or populations. The various analyses performed in the context of correlation may be conducted in real-time, near real-time, and/or based on historical patterns of data from different sources, different users, and/or within individual users and/or populations of users over time.

It will be appreciated that many of the tests disclosed herein utilize user data collected regarding the user's response to various stimuli. The user data may take, for example, the form of images of the user, measurements from sensors directed at the user, etc., as described herein. It will also be appreciated, that as the user goes about their day, they may come in contact with external stimuli appropriate for a particular test. The external stimuli may take the form of environmental stimuli from the ambient environment and/or stimuli provided by the display system to the user (e.g., in the form of images and/or sounds provided to the user for purposes other than performing a particular health analysis). Advantageously, the display system may be configured to passively collect data regarding the user in order to perform various analyses unobtrusively, without specifically actively subjecting the user to particular stimuli. For example, the display system may be configured to gather external data (e.g., date, temperature, ambient noise, lighting conditions, distance from the mirror, etc.) and/or outputs provided by the display system to the user, which are synchronized or otherwise associated with the user data. The environmental data and outputs provided by the display system to the user may be referred to as external data.

In some embodiments, the external and user data may be stored on a continual basis and then subsequently analyzed. For example, image information from outward facing cameras and sound inputs from microphones of the display system may be continually collected, along with user data from various sensors attached to or directed at the user (e.g., inward facing cameras, electrodes, etc.). The display system may be configured to perform an analysis of the collected external and user data as that information is collected, to determine whether the collected data is relevant to one or more of the analyses disclosed herein, e.g. user health analyses, disclosed herein.

In some embodiments, timing and frequency of data analyses are determined by pre-defined decision rules for analyses, including but not limited to the necessary types and amounts of data that have been collected at any particular point in time. If it is determined that the necessary types and amounts of data for a particular analysis are present, the display system may be configured to then perform the associated analysis. In some other embodiments, the analysis and/or determination of whether appropriate data is present may be conducted at a later time (e.g., at preset intervals, such as at night or other times when the display system may not be used by the user, and/or in response to a particular input from the user to perform one or more analyses). Preferably, the collection of the external and user data is continuous while the user is wearing the display system, while the analysis and/or determination of whether appropriate data is present is performed intermittently, or sporadically, e.g., in accordance with a preset schedule and/or an input by the user or other party. The collected data, e.g., external data and user data, represent a plurality of sets of data that may be used for multiple analyses, with one set of data appropriate for one of the analyses and another set of data appropriate for other analyses. Moreover, the availability of the raw external and user data facilitates the later development of analyses that may use combinations of data not readily utilized in traditional analyses. In some embodiments, the contemporaneous acquisition of external and user data allows multiple analyses to be performed to determine the state of the user at a given point in time. Advantageously, these analyses, performed by evaluating data derived from the same point in time, may help to validate conclusions provided by each individual analysis.

Advantageously, these analyses may be performed continuously over time, e.g., particular analyses may be performed multiple times over the span of hours, days, weeks, months, or even years. As a result, a large data set may be obtained and analyzed before making a conclusion regarding a particular analysis. Such a large data set may improve the reliability and level confidence in the conclusions drawn from the analyses, relative to a single analysis of data obtain at only a single point in time.

In addition, long-term trends may also be obtained by historical analysis of collected external and user data. As a result, both contemporary user health conditions and trends regarding these user conditions may be determined, which may provide data for determining future trends more specifically tailored to a particular user. For example, it is possible that certain conditions may not become apparent until particular thresholds of symptoms are reached, and it may traditionally be difficult to analyze the state of the user before a condition is found since prior data sets relevant to the condition would not normally be obtained by a clinician, since the relevance of those data sets was not previously understood. The passive collection and storage of external and user data advantageously provides the display system with an ability to reach back in time to conduct analyses of the user at earlier points in time. As a result, a more accurate understanding of the progression of a condition may be determined. In addition, rather than extrapolating from norms for a general population, the rate of change of a condition for a user may be determined, thereby providing information for more accurately projecting the progression of the condition.

In some embodiments, all data collected in any configuration may be utilized to provide one or more interventions to the user, in real-time or near real-time, or with a pre-specified delay in time. The user or another entity with authorized access and control rights may determine the content and timing of any intervention in some embodiments. Intervention decisions may be invoked in an automated or manual fashion in the system or via a remote device. The data may be analyzed and one or more algorithms may be used to trigger a new intervention or set of interventions, and/or to modify a user's ongoing intervention or series of interventions, such as a medical treatment or psychological therapy. In some embodiments, interventions may be delivered by the display system to the user (e.g., in the form of visual and/or auditory content, and/or haptic feedback) and/or by other technological devices with or without a visual display. The data may be used to assess one or more combinations of a pre-specified set of parameters (e.g., health parameters) that may be used to support or perform an assessment or diagnosis of relevant user states and conditions, such as a medical diagnosis.

In some embodiments, the user and/or environmental data (e.g., including real and/or virtual content), as well as the relationship between the user and/or environmental data, may be stored and/or shared, e.g., with other users of similar devices in the local vicinity and/or with others. Advantageously, such sharing may aid in increasing the accuracy of any correlation made with the user and/or environmental data, since data sets from other users would be available. In some other embodiments, the user and/or environmental data, and/or information derived from this data may be shared with third parties to, e.g., provide notifications regarding stimuli causing a common reaction with people at a particular location. In some embodiments, data may be shared with other technological devices with or without display functionality that are capable of receiving data input, for example, a smartphone or the like.

Reference will now be made to the drawings, in which like reference numerals refer to like parts throughout.

Figure 2:
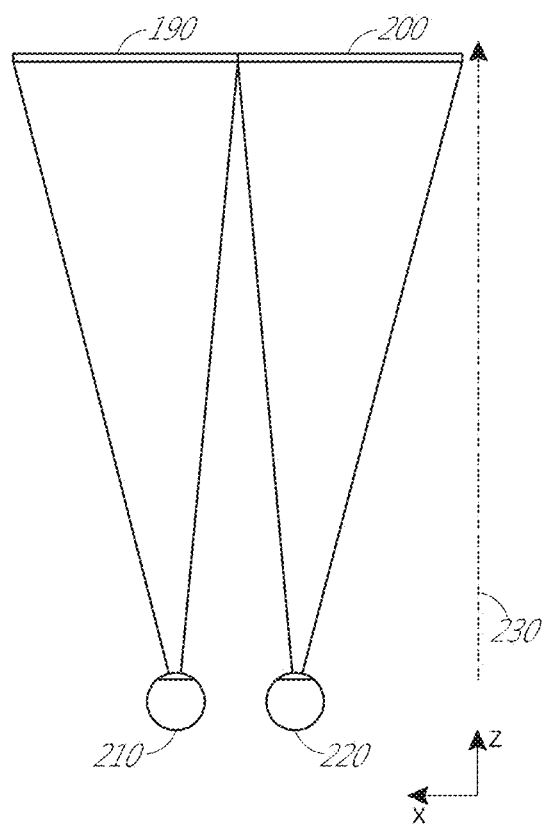
FIG. 2 illustrates a conventional display system for simulating three-dimensional imagery for a user.

FIG. 2 illustrates a conventional display system for simulating three-dimensional imagery for a user. It will be appreciated that a user's eyes are spaced apart and that, when looking at a real object in space, each eye will have a slightly different view of the object and may form an image of the object at different locations on the retina of each eye. This may be referred to as binocular disparity and may be utilized by the human visual system to provide a perception of depth. Conventional display systems simulate binocular disparity by presenting two distinct images 190, 200 with slightly different views of the same virtual object—one for each eye 210, 220—corresponding to the views of the virtual object that would be seen by each eye were the virtual object a real object at a desired depth. These images provide binocular cues that the user's visual system may interpret to derive a perception of depth.

With continued reference to FIG. 2, the images 190, 200 are spaced from the eyes 210, 220 by a distance 230 on a z-axis. The z-axis is parallel to the optical axis of the viewer with their eyes fixated on an object at optical infinity directly ahead of the viewer. The images 190, 200 are flat and at a fixed distance from the eyes 210, 220. Based on the slightly different views of a virtual object in the images presented to the eyes 210, 220, respectively, the eyes may naturally rotate such that an image of the object falls on corresponding points on the retinas of each of the eyes, to maintain single binocular vision. This rotation may cause the lines of sight of each of the eyes 210, 220 to converge onto a point in space at which the virtual object is perceived to be present. As a result, providing three-dimensional imagery conventionally involves providing binocular cues that may manipulate the vergence of the user's eyes 210, 220, and that the human visual system interprets to provide a perception of depth.

Figure 3A:
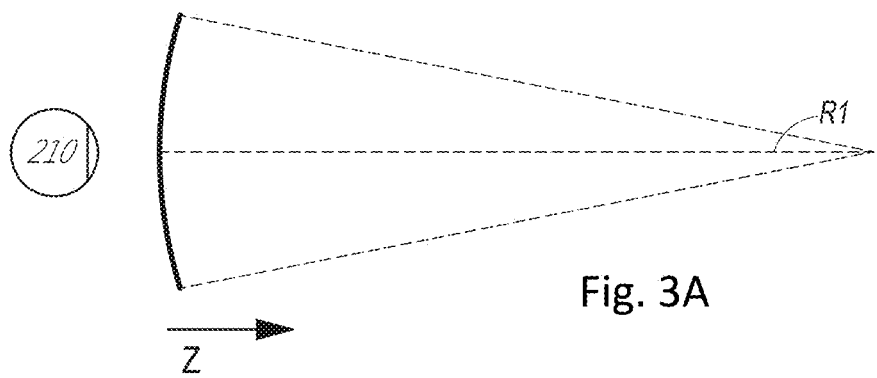
FIGS. 3A-3C illustrate relationships between radius of curvature and focal radius.
Figure 3B:
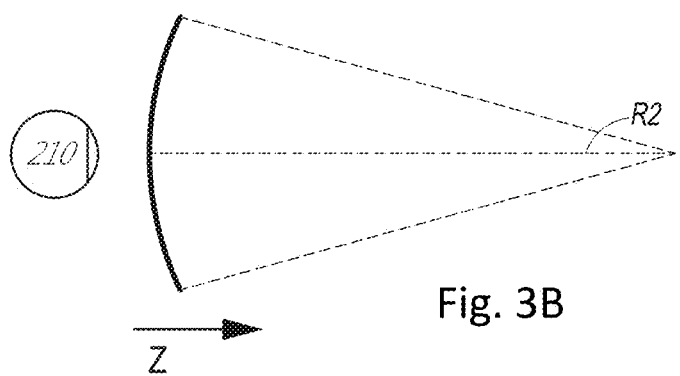
Figure 3C:
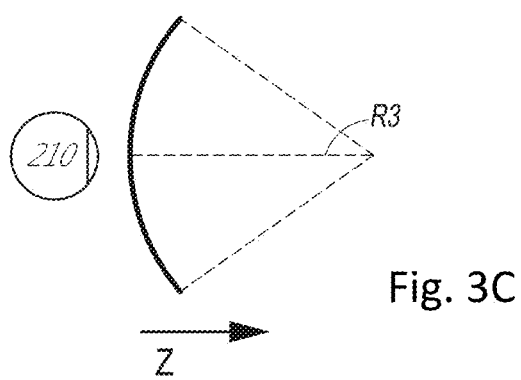

Generating a realistic and comfortable perception of depth is challenging, however. It will be appreciated that light from objects at different distances from the eyes have wavefronts with different amounts of divergence. FIGS. 3A-3C illustrate relationships between distance and the divergence of light rays. The distance between the object and the eye 210 is represented by, in order of decreasing distance, R1, R2, and R3. As shown in FIGS. 3A-3C, the light rays become more divergent as distance to the object decreases. Conversely, as distance increases, the light rays become more collimated. Stated another way, it may be said that the light field produced by a point (the object or a part of the object) has a spherical wavefront curvature, which is a function of how far away the point is from the eye of the user. The curvature increases with decreasing distance between the object and the eye 210. While only a single eye 210 is illustrated for clarity of illustration in FIGS. 3A-3C and other figures herein, the discussions regarding eye 210 may be applied to both eyes 210 and 220 of a viewer.

With continued reference to FIGS. 3A-3C, light from an object that the viewer's eyes are fixated on may have different degrees of wavefront divergence. Due to the different amounts of wavefront divergence, the light may be focused differently by the lens of the eye, which in turn may require the lens to assume different shapes to form a focused image on the retina of the eye. Where a focused image is not formed on the retina, the resulting retinal blur acts as a cue to accommodation that causes a change in the shape of the lens of the eye until a focused image is formed on the retina. For example, the cue to accommodation may trigger the ciliary muscles surrounding the lens of the eye to relax or contract, thereby modulating the force applied to the suspensory ligaments holding the lens, thus causing the shape of the lens of the eye to change until retinal blur of an object of fixation is eliminated or minimized, thereby forming a focused image of the object of fixation on the retina (e.g., fovea) of the eye. The process by which the lens of the eye changes shape may be referred to as accommodation, and the shape of the lens of the eye required to form a focused image of the object of fixation on the retina (e.g., fovea) of the eye may be referred to as an accommodative state.

Figure 4A:
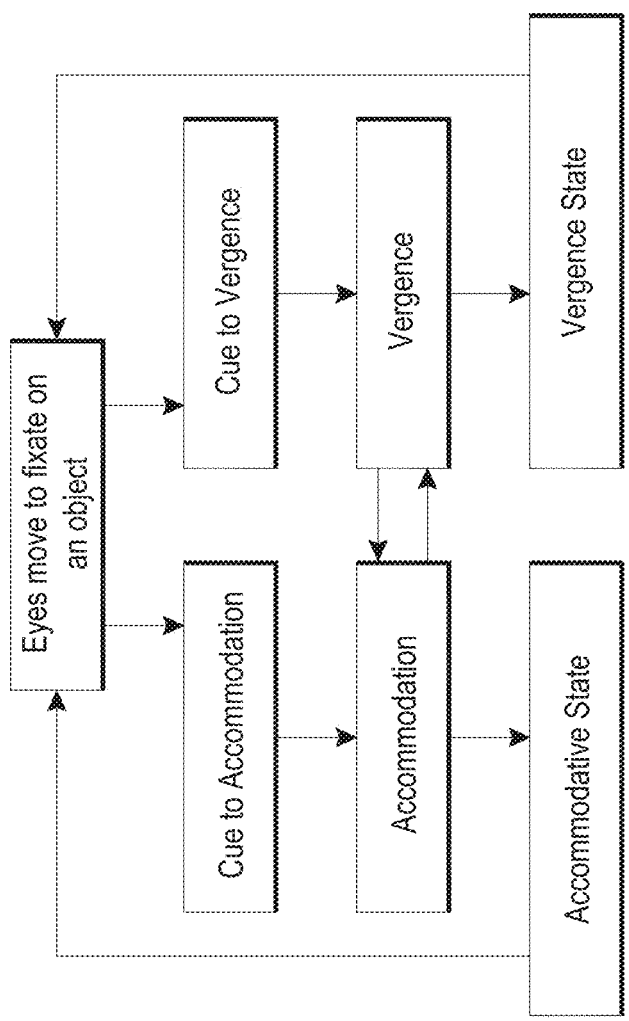
FIG. 4A illustrates a representation of the accommodation-vergence response of the human visual system.

With reference now to FIG. 4A, a representation of the accommodation-vergence response of the human visual system is illustrated. The movement of the eyes to fixate on an object causes the eyes to receive light from the object, with the light forming an image on each of the retinas of the eyes. The presence of retinal blur in the image formed on the retina may provide a cue to accommodation, and the relative locations of the image on the retinas may provide a cue to vergence. The cue to accommodation causes accommodation to occur, resulting in the lenses of the eyes each assuming a particular accommodative state that forms a focused image of the object on the retina (e.g., fovea) of the eye. On the other hand, the cue to vergence causes vergence movements (rotation of the eyes) to occur such that the images formed on each retina of each eye are at corresponding retinal points that maintain single binocular vision. In these positions, the eyes may be said to have assumed a particular vergence state. With continued reference to FIG. 4A, accommodation may be understood to be the process by which the eye achieves a particular accommodative state, and vergence may be understood to be the process by which the eye achieves a particular vergence state. As indicated in FIG. 4A, the accommodative and vergence states of the eyes may change if the user fixates on another object. For example, the accommodated state may change if the user fixates on a new object at a different depth on the z-axis.

Without being limited by theory, it is believed that viewers of an object may perceive the object as being "three-dimensional" due to a combination of vergence and accommodation. As noted above, vergence movements (e.g., rotation of the eyes so that the pupils move toward or away from each other to converge the lines of sight of the eyes to fixate upon an object) of the two eyes relative to each other are closely associated with accommodation of the lenses of the eyes. Under normal conditions, changing the shapes of the lenses of the eyes to change focus from one object to another object at a different distance will automatically cause a matching change in vergence to the same distance, under a relationship known as the "accommodation-vergence reflex." Likewise, a change in vergence will trigger a matching change in lens shape under normal conditions.

Figure 4B:
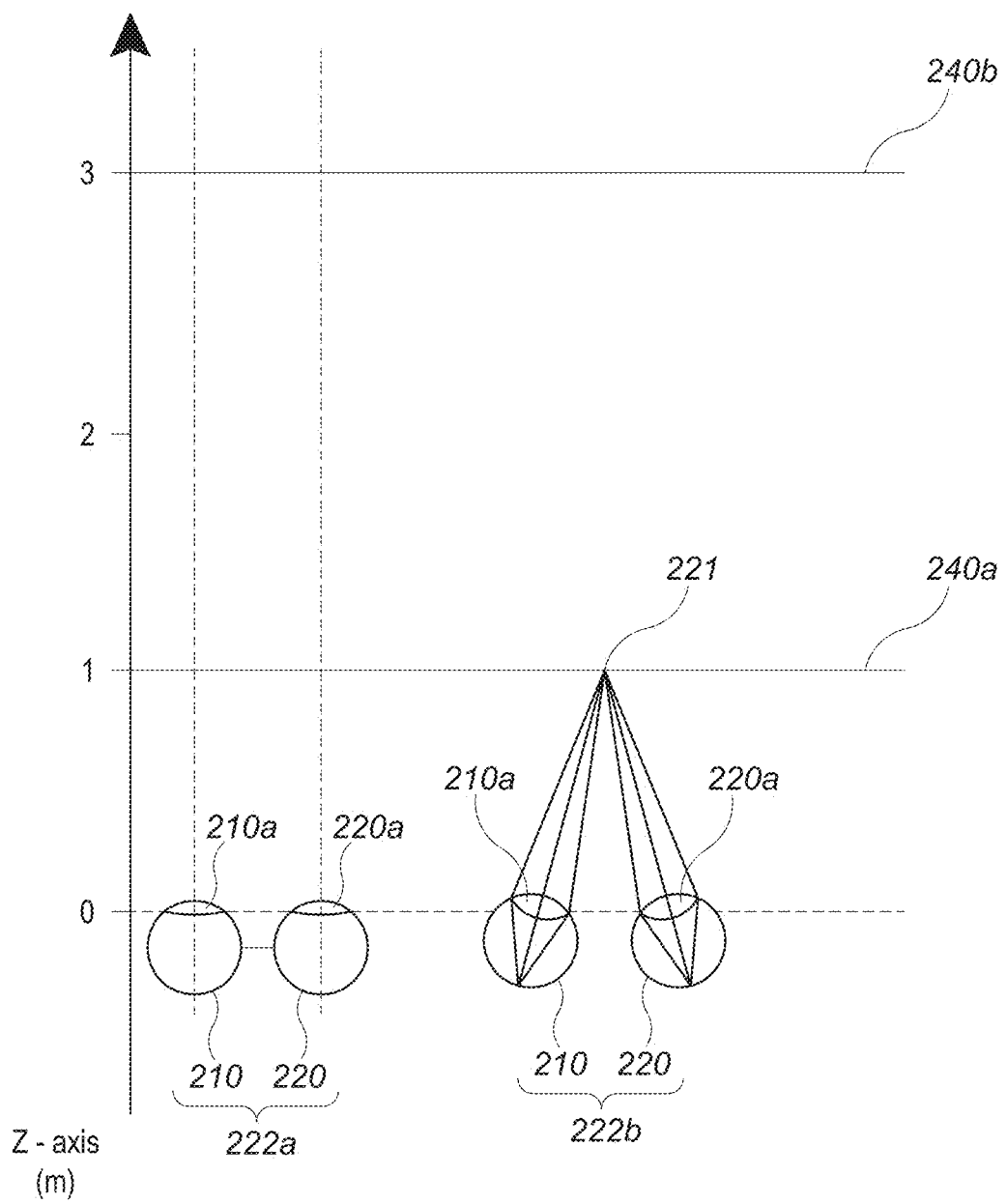
FIG. 4B illustrates examples of different accommodative states and vergence states of a pair of eyes of the user.

With reference now to FIG. 4B, examples of different accommodative and vergence states of the eyes are illustrated. The pair of eyes 222a are fixated on an object at optical infinity, while the pair eyes 222b are fixated on an object 221 at less than optical infinity. Notably, the vergence states of each pair of eyes is different, with the pair of eyes 222a directed straight ahead, while the pair of eyes 222 converge on the object 221. The accommodative states of the eyes forming each pair of eyes 222a and 222b are also different, as represented by the different shapes of the lenses 210a, 220a.

Undesirably, many users of conventional "3-D" display systems find such conventional systems to be uncomfortable or may not perceive a sense of depth at all due to a mismatch between accommodative and vergence states in these displays. As noted above, many stereoscopic or "3-D" display systems display a scene by providing slightly different images to each eye. Such systems are uncomfortable for many viewers, since they, among other things, simply provide different presentations of a scene and cause changes in the vergence states of the eyes, but without a corresponding change in the accommodative states of those eyes. Rather, the images are shown by a display at a fixed distance from the eyes, such that the eyes view all the image information at a single accommodative state. Such an arrangement works against the "accommodation-vergence reflex" by causing changes in the vergence state without a matching change in the accommodative state. This mismatch is believed to cause viewer discomfort. Display systems that provide a better match between accommodation and vergence may form more realistic and comfortable simulations of three-dimensional imagery.

Without being limited by theory, it is believed that the human eye typically may interpret a finite number of depth planes to provide depth perception. Consequently, a highly believable simulation of perceived depth may be achieved by providing, to the eye, different presentations of an image corresponding to each of these limited numbers of depth planes. In some embodiments, the different presentations may provide both cues to vergence and matching cues to accommodation, thereby providing physiologically correct accommodation-vergence matching.

With continued reference to FIG. 4B, two depth planes 240, corresponding to different distances in space from the eyes 210, 220, are illustrated. For a given depth plane 240, vergence cues may be provided by the displaying of images of appropriately different perspectives for each eye 210, 220. In addition, for a given depth plane 240, light forming the images provided to each eye 210, 220 may have a wavefront divergence corresponding to a light field produced by a point at the distance of that depth plane 240.

In the illustrated embodiment, the distance, along the z-axis, of the depth plane 240 containing the point 221 is 1 m. As used herein, distances or depths along the z-axis may be measured with a zero-point located at the exit pupils of the user's eyes. Thus, a depth plane 240 located at a depth of 1 m corresponds to a distance of 1 m away from the exit pupils of the user's eyes, on the optical axis of those eyes with the eyes directed towards optical infinity. As an approximation, the depth or distance along the z-axis may be measured from the display in front of the user's eyes (e.g., from the surface of a waveguide), plus a value for the distance between the device and the exit pupils of the user's eyes. That value may be called the eye relief and corresponds to the distance between the exit pupil of the user's eye and the display worn by the user in front of the eye. In practice, the value for the eye relief may be a normalized value used generally for all viewers. For example, the eye relief may be assumed to be 20 mm and a depth plane that is at a depth of 1 m may be at a distance of 980 mm in front of the display.

Figure 4C:
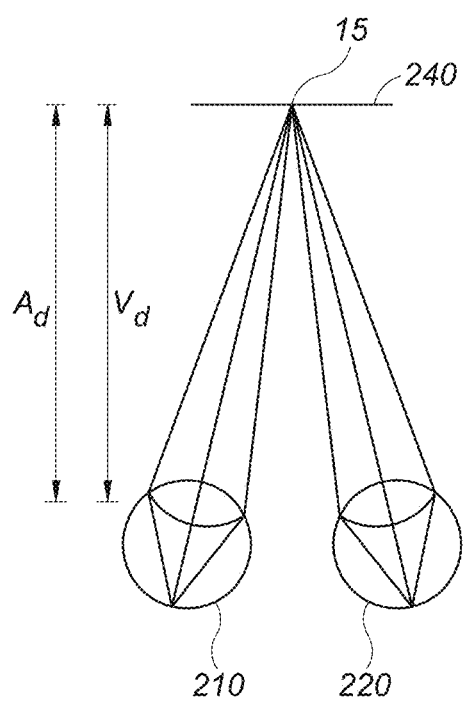
FIG. 4C illustrates an example of a representation of a top-down view of a user viewing content via a display system.
Figure 4D:
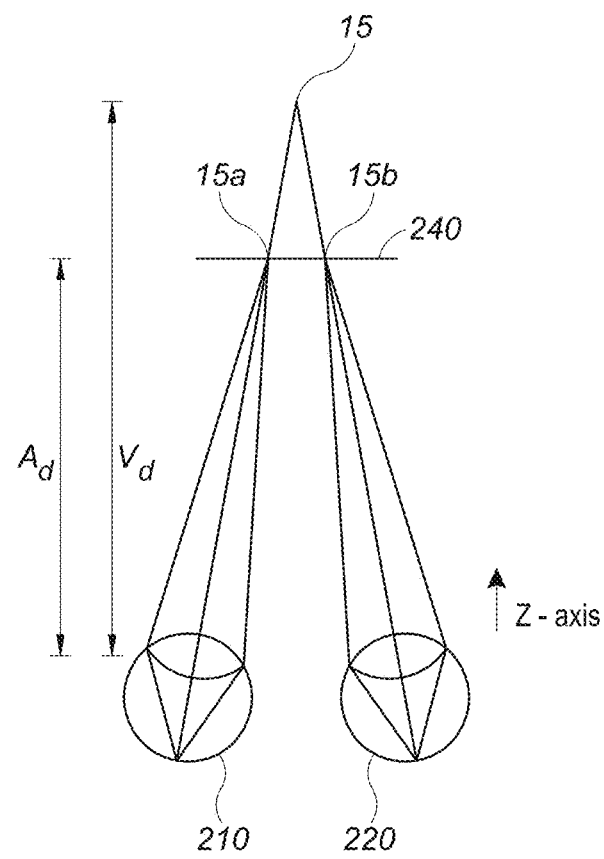
FIG. 4D illustrates another example of a representation of a top-down view of a user viewing content via a display system.

With reference now to FIGS. 4C and 4D, examples of matched accommodation-vergence distances and mismatched accommodation-vergence distances are illustrated, respectively. As illustrated in FIG. 4C, the display system may provide images of a virtual object to each eye 210, 220. The images may cause the eyes 210, 220 to assume a vergence state in which the eyes converge on a point 15 on a depth plane 240. In addition, the images may be formed by a light having a wavefront curvature corresponding to real objects at that depth plane 240. As a result, the eyes 210, 220 assume an accommodative state in which the images are in focus on the retinas of those eyes. Thus, the user may perceive the virtual object as being at the point 15 on the depth plane 240.

It will be appreciated that each of the accommodative and vergence states of the eyes 210, 220 are associated with a particular distance on the z-axis. For example, an object at a particular distance from the eyes 210, 220 causes those eyes to assume particular accommodative states based upon the distances of the object. The distance associated with a particular accommodative state may be referred to as the accommodation distance, $A_d$. Similarly, there are particular vergence distances, $V_d$, associated with the eyes in particular vergence states, or positions relative to one another. Where the accommodation distance and the vergence distance match, the relationship between accommodation and vergence may be said to be physiologically correct. This is considered to be the most comfortable scenario for a viewer.

In stereoscopic displays, however, the accommodation distance and the vergence distance may not always match. For example, as illustrated in FIG. 4D, images displayed to the eyes 210, 220 may be displayed with wavefront divergence corresponding to depth plane 240, and the eyes 210, 220 may assume a particular accommodative state in which the points 15a, 15b on that depth plane are in focus. However, the images displayed to the eyes 210, 220 may provide cues for vergence that cause the eyes 210, 220 to converge on a point 15 that is not located on the depth plane 240. As a result, the accommodation distance corresponds to the distance from the exit pupils of the eyes 210, 220 to the depth plane 240, while the vergence distance corresponds to the larger distance from the exit pupils of the eyes 210, 220 to the point 15, in some embodiments. The accommodation distance is different from the vergence distance. Consequently, there is an accommodation-vergence mismatch. Such a mismatch is considered undesirable and may cause discomfort in the user. It will be appreciated that the mismatch corresponds to distance (e.g., $V_d$-$A_d$) and may be characterized using diopters.

In some embodiments, it will be appreciated that a reference point other than exit pupils of the eyes 210, 220 may be utilized for determining distance for determining accommodation-vergence mismatch, so long as the same reference point is utilized for the accommodation distance and the vergence distance. For example, the distances could be measured from the cornea to the depth plane, from the retina to the depth plane, from the eyepiece (e.g., a waveguide of the display device) to the depth plane, and so on.

Without being limited by theory, it is believed that users may still perceive accommodation-vergence mismatches of up to about 0.25 diopter, up to about 0.33 diopter, and up to about 0.5 diopter as being physiologically correct, without the mismatch itself causing significant discomfort. In some embodiments, display systems disclosed herein (e.g., the display system 250, FIG. 6) present images to the viewer having accommodation-vergence mismatch of about 0.5 diopter or less. In some other embodiments, the accommodation-vergence mismatch of the images provided by the display system is about 0.33 diopter or less. In yet other embodiments, the accommodation-vergence mismatch of the images provided by the display system is about 0.25 diopter or less, including about 0.1 diopter or less.

Figure 5:
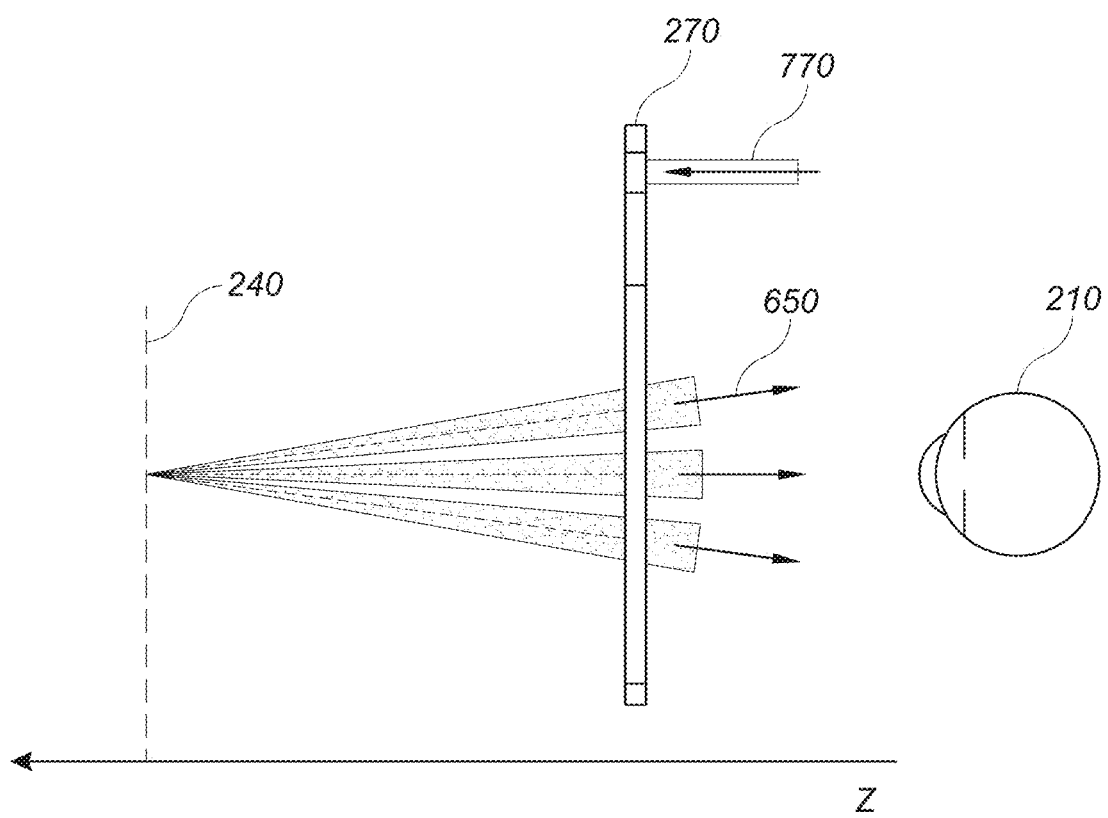
FIG. 5 illustrates aspects of an approach for simulating three-dimensional imagery by modifying wavefront divergence.

FIG. 5 illustrates aspects of an approach for simulating three-dimensional imagery by modifying wavefront divergence. The display system includes a waveguide 270 that is configured to receive light 770 that is encoded with image information, and to output that light to the user's eye 210. The waveguide 270 may output the light 650 with a defined amount of wavefront divergence corresponding to the wavefront divergence of a light field produced by a point on a desired depth plane 240. In some embodiments, the same amount of wavefront divergence is provided for all objects presented on that depth plane. In addition, it will be illustrated that the other eye of the user may be provided with image information from a similar waveguide.

In some embodiments, a single waveguide may be configured to output light with a set amount of wavefront divergence corresponding to a single or limited number of depth planes and/or the waveguide may be configured to output light of a limited range of wavelengths. Consequently, in some embodiments, a plurality or stack of waveguides may be utilized to provide different amounts of wavefront divergence for different depth planes and/or to output light of different ranges of wavelengths.

Figure 6:
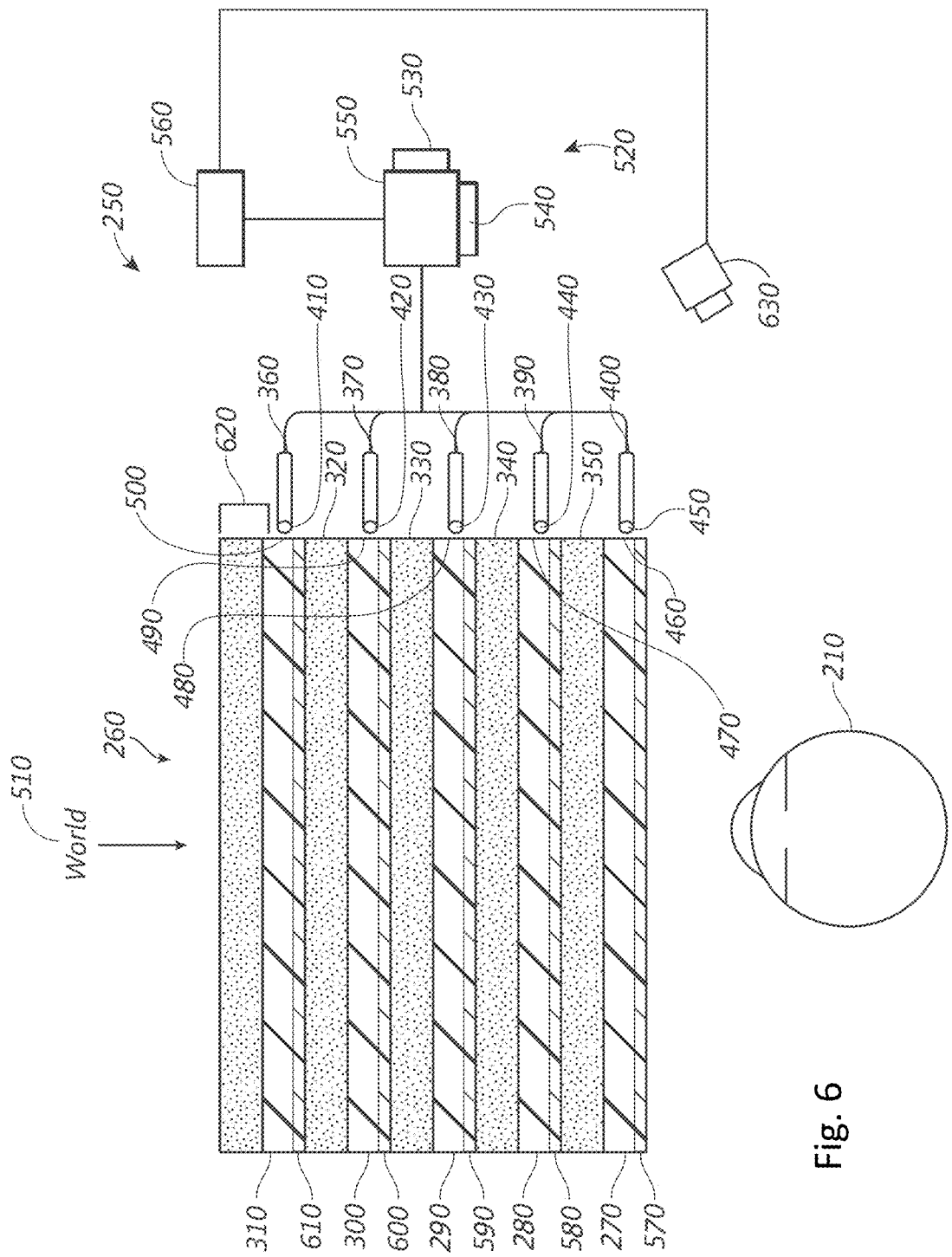
FIG. 6 illustrates an example of a waveguide stack for outputting image information to a user.

FIG. 6 illustrates an example of a waveguide stack for outputting image information to a user. A display system 250 includes a stack of waveguides, or stacked waveguide assembly, 260 that may be utilized to provide three-dimensional perception to the eye/brain using a plurality of waveguides 270, 280, 290, 300, 310. It will be appreciated that the display system 250 may be considered a light field display in some embodiments. In addition, the waveguide assembly 260 may also be referred to as an eyepiece.

In some embodiments, the display system 250 may be configured to provide substantially continuous cues to vergence and multiple discrete cues to accommodation. The cues to vergence may be provided by displaying different images to each of the eyes of the user, and the cues to accommodation may be provided by outputting the light that forms the images with selectable discrete amounts of wavefront divergence. Stated another way, the display system 250 may be configured to output light with variable levels of wavefront divergence. In some embodiments, each discrete level of wavefront divergence corresponds to a particular depth plane and may be provided by a particular one of the waveguides 270, 280, 290, 300, 310.

With continued reference to FIG. 6, the waveguide assembly 260 may also include a plurality of features 320, 330, 340, 350 between the waveguides. In some embodiments, the features 320, 330, 340, 350 may be one or more lenses. The waveguides 270, 280, 290, 300, 310 and/or the plurality of lenses 320, 330, 340, 350 may be configured to send image information to the eye with various levels of wavefront curvature or light ray divergence. Each waveguide level may be associated with a particular depth plane and may be configured to output image information corresponding to that depth plane. Image injection devices 360, 370, 380, 390, 400 may function as a source of light for the waveguides and may be utilized to inject image information into the waveguides 270, 280, 290, 300, 310, each of which may be configured, as described herein, to distribute incoming light across each respective waveguide, for output toward the eye 210. Light exits an output surface 410, 420, 430, 440, 450 of the image injection devices 360, 370, 380, 390, 400 and is injected into a corresponding input surface 460, 470, 480, 490, 500 of the waveguides 270, 280, 290, 300, 310. In some embodiments, each of the input surfaces 460, 470, 480, 490, 500 may be an edge of a corresponding waveguide, or may be part of a major surface of the corresponding waveguide (that is, one of the waveguide surfaces directly facing the world 510 or the viewer's eye 210). In some embodiments, a single beam of light (e.g. a collimated beam) may be injected into each waveguide to output an entire field of cloned collimated beams that are directed toward the eye 210 at particular angles (and amounts of divergence) corresponding to the depth plane associated with a particular waveguide. In some embodiments, a single one of the image injection devices 360, 370, 380, 390, 400 may be associated with and inject light into a plurality (e.g., three) of the waveguides 270, 280, 290, 300, 310.

In some embodiments, the image injection devices 360, 370, 380, 390, 400 are discrete displays that each produce image information for injection into a corresponding waveguide 270, 280, 290, 300, 310, respectively. In some other embodiments, the image injection devices 360, 370, 380, 390, 400 are the output ends of a single multiplexed display which may, e.g., pipe image information via one or more optical conduits (such as fiber optic cables) to each of the image injection devices 360, 370, 380, 390, 400. It will be appreciated that the image information provided by the image injection devices 360, 370, 380, 390, 400 may include light of different wavelengths, or colors (e.g., different component colors, as discussed herein).

In some embodiments, the light injected into the waveguides 270, 280, 290, 300, 310 is provided by a light projector system 520, which comprises a light module 530, which may include a light emitter, such as a light emitting diode (LED). The light from the light module 530 may be directed to and modified by a light modulator 540, e.g., a spatial light modulator, via a beam splitter 550. The light modulator 540 may be configured to change the perceived intensity of the light injected into the waveguides 270, 280, 290, 300, 310 to encode the light with image information. Examples of spatial light modulators include liquid crystal displays (LCD) including a liquid crystal on silicon (LCOS) displays. It will be appreciated that the image injection devices 360, 370, 380, 390, 400 are illustrated schematically and, in some embodiments, these image injection devices may represent different light paths and locations in a common projection system configured to output light into associated ones of the waveguides 270, 280, 290, 300, 310. In some embodiments, the waveguides of the waveguide assembly 260 may function as ideal lens while relaying light injected into the waveguides out to the user's eyes. In this conception, the object may be the spatial light modulator 540 and the image may be the image on the depth plane.

In some embodiments, the display system 250 may be a scanning fiber display comprising one or more scanning fibers configured to project light in various patterns (e.g., raster scan, spiral scan, Lissajous patterns, etc.) into one or more waveguides 270, 280, 290, 300, 310 and ultimately to the eye 210 of the viewer. In some embodiments, the illustrated image injection devices 360, 370, 380, 390, 400 may schematically represent a single scanning fiber or a bundle of scanning fibers configured to inject light into one or a plurality of the waveguides 270, 280, 290, 300, 310. In some other embodiments, the illustrated image injection devices 360, 370, 380, 390, 400 may schematically represent a plurality of scanning fibers or a plurality of bundles of scanning fibers, each of which are configured to inject light into an associated one of the waveguides 270, 280, 290, 300, 310. It will be appreciated that one or more optical fibers may be configured to transmit light from the light module 530 to the one or more waveguides 270, 280, 290, 300, 310. It will be appreciated that one or more intervening optical structures may be provided between the scanning fiber, or fibers, and the one or more waveguides 270, 280, 290, 300, 310 to, e.g., redirect light exiting the scanning fiber into the one or more waveguides 270, 280, 290, 300, 310.

A controller 560 controls the operation of one or more of the stacked waveguide assembly 260, including operation of the image injection devices 360, 370, 380, 390, 400, the light source 530, and the light modulator 540. In some embodiments, the controller 560 is part of the local data processing module 140. The controller 560 includes programming (e.g., instructions in a non-transitory medium) that regulates the timing and provision of image information to the waveguides 270, 280, 290, 300, 310 according to, e.g., any of the various schemes disclosed herein. In some embodiments, the controller may be a single integral device, or a distributed system connected by wired or wireless communication channels. The controller 560 may be part of the processing modules 140 or 150 (FIG. 9D) in some embodiments.

With continued reference to FIG. 6, the waveguides 270, 280, 290, 300, 310 may be configured to propagate light within each respective waveguide by total internal reflection (TIR). The waveguides 270, 280, 290, 300, 310 may each be planar or have another shape (e.g., curved), with major top and bottom surfaces and edges extending between those major top and bottom surfaces. In the illustrated configuration, the waveguides 270, 280, 290, 300, 310 may each include out-coupling optical elements 570, 580, 590, 600, 610 that are configured to extract light out of a waveguide by redirecting the light, propagating within each respective waveguide, out of the waveguide to output image information to the eye 210. Extracted light may also be referred to as out-coupled light and the out-coupling optical elements light may also be referred to light extracting optical elements. An extracted beam of light may be outputted by the waveguide at locations at which the light propagating in the waveguide strikes a light extracting optical element. The out-coupling optical elements 570, 580, 590, 600, 610 may, for example, be gratings, including diffractive optical features, as discussed further herein. While illustrated disposed at the bottom major surfaces of the waveguides 270, 280, 290, 300, 310, for ease of description and drawing clarity, in some embodiments, the out-coupling optical elements 570, 580, 590, 600, 610 may be disposed at the top and/or bottom major surfaces, and/or may be disposed directly in the volume of the waveguides 270, 280, 290, 300, 310, as discussed further herein. In some embodiments, the out-coupling optical elements 570, 580, 590, 600, 610 may be formed in a layer of material that is attached to a transparent substrate to form the waveguides 270, 280, 290, 300, 310. In some other embodiments, the waveguides 270, 280, 290, 300, 310 may be a monolithic piece of material and the out-coupling optical elements 570, 580, 590, 600, 610 may be formed on a surface and/or in the interior of that piece of material.

With continued reference to FIG. 6, as discussed herein, each waveguide 270, 280, 290, 300, 310 is configured to output light to form an image corresponding to a particular depth plane. For example, the waveguide 270 nearest the eye may be configured to deliver collimated light (which was injected into such waveguide 270), to the eye 210. The collimated light may be representative of the optical infinity focal plane. The next waveguide up 280 may be configured to send out collimated light which passes through the first lens 350 (e.g., a negative lens) before it may reach the eye 210; such first lens 350 may be configured to create a slight convex wavefront curvature so that the eye/brain interprets light coming from that next waveguide up 280 as coming from a first focal plane closer inward toward the eye 210 from optical infinity. Similarly, the third up waveguide 290 passes its output light through both the first 350 and second 340 lenses before reaching the eye 210; the combined optical power of the first 350 and second 340 lenses may be configured to create another incremental amount of wavefront curvature so that the eye/brain interprets light coming from the third waveguide 290 as coming from a second focal plane that is even closer inward toward the person from optical infinity than was light from the next waveguide up 280.

The other waveguide layers 300, 310 and lenses 330, 320 are similarly configured, with the highest waveguide 310 in the stack sending its output through all of the lenses between it and the eye for an aggregate focal power representative of the closest focal plane to the person. To compensate for the stack of lenses 320, 330, 340, 350 when viewing/interpreting light coming from the world 510 on the other side of the stacked waveguide assembly 260, a compensating lens layer 620 may be disposed at the top of the stack to compensate for the aggregate power of the lens stack 320, 330, 340, 350 below. Such a configuration provides as many perceived focal planes as there are available waveguide/lens pairings. Both the out-coupling optical elements of the waveguides and the focusing aspects of the lenses may be static (i.e., not dynamic or electro-active). In some alternative embodiments, either or both may be dynamic using electro-active features.

In some embodiments, two or more of the waveguides 270, 280, 290, 300, 310 may have the same associated depth plane. For example, multiple waveguides 270, 280, 290, 300, 310 may be configured to output images set to the same depth plane, or multiple subsets of the waveguides 270, 280, 290, 300, 310 may be configured to output images set to the same plurality of depth planes, with one set for each depth plane. This may provide advantages for forming a tiled image to provide an expanded field of view at those depth planes.

With continued reference to FIG. 6, the out-coupling optical elements 570, 580, 590, 600, 610 may be configured to both redirect light out of their respective waveguides and to output this light with the appropriate amount of divergence or collimation for a particular depth plane associated with the waveguide. As a result, waveguides having different associated depth planes may have different configurations of out-coupling optical elements 570, 580, 590, 600, 610, which output light with a different amount of divergence depending on the associated depth plane. In some embodiments, the light extracting optical elements 570, 580, 590, 600, 610 may be volumetric or surface features, which may be configured to output light at specific angles. For example, the light extracting optical elements 570, 580, 590, 600, 610 may be volume holograms, surface holograms, and/or diffraction gratings. In some embodiments, the features 320, 330, 340, 350 may not be lenses; rather, they may simply be spacers (e.g., cladding layers and/or structures for forming air gaps).

In some embodiments, the out-coupling optical elements 570, 580, 590, 600, 610 are diffractive features that form a diffraction pattern, or "diffractive optical element" (also referred to herein as a "DOE"). Preferably, the DOE's have a sufficiently low diffraction efficiency so that only a portion of the light of the beam is deflected away toward the eye 210 with each intersection of the DOE, while the rest continues to move through a waveguide via TIR. The light carrying the image information is thus divided into a number of related exit beams that exit the waveguide at a multiplicity of locations and the result is a fairly uniform pattern of exit emission toward the eye 210 for this particular collimated beam bouncing around within a waveguide.

In some embodiments, one or more DOEs may be switchable between "on" states in which they actively diffract, and "off" states in which they do not significantly diffract. For instance, a switchable DOE may comprise a layer of polymer dispersed liquid crystal, in which microdroplets comprise a diffraction pattern in a host medium, and the refractive index of the microdroplets may be switched to substantially match the refractive index of the host material (in which case the pattern does not appreciably diffract incident light) or the microdroplet may be switched to an index that does not match that of the host medium (in which case the pattern actively diffracts incident light).

In some embodiments, a camera assembly 630 (e.g., a digital camera, including visible light and infrared light cameras) may be provided to capture images of the eye 210 and/or tissue around the eye 210 to, e.g., detect user inputs and/or to monitor the physiological state of the user. As used herein, a camera may be any image capture device. In some embodiments, the camera assembly 630 may include an image capture device and a light source to project light (e.g., infrared light) to the eye, which may then be reflected by the eye and detected by the image capture device. In some embodiments, the camera assembly 630 may be attached to the frame 80 (FIG. 9D) and may be in electrical communication with the processing modules 140 and/or 150, which may process image information from the camera assembly 630. In some embodiments, one camera assembly 630 may be utilized for each eye, to separately monitor each eye.

Figure 7:
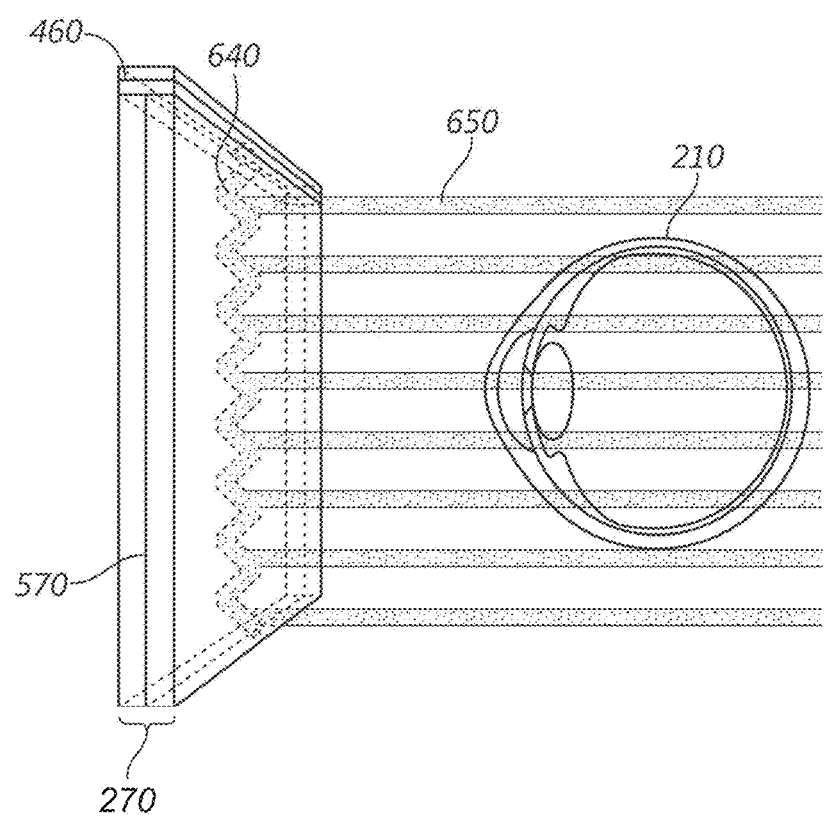
FIG. 7 illustrates an example of exit beams outputted by a waveguide.

With reference now to FIG. 7, an example of exit beams outputted by a waveguide is shown. One waveguide is illustrated, but it will be appreciated that other waveguides in the waveguide assembly 260 (FIG. 6) may function similarly, where the waveguide assembly 260 includes multiple waveguides. Light 640 is injected into the waveguide 270 at the input surface 460 of the waveguide 270 and propagates within the waveguide 270 by TIR. At points where the light 640 impinges on the DOE 570, a portion of the light exits the waveguide as exit beams 650. The exit beams 650 are illustrated as substantially parallel but, as discussed herein, they may also be redirected to propagate to the eye 210 at an angle (e.g., forming divergent exit beams), depending on the depth plane associated with the waveguide 270. It will be appreciated that substantially parallel exit beams may be indicative of a waveguide with out-coupling optical elements that out-couple light to form images that appear to be set on a depth plane at a large distance (e.g., optical infinity) from the eye 210. Other waveguides or other sets of out-coupling optical elements may output an exit beam pattern that is more divergent, which would require the eye 210 to accommodate to a closer distance to bring it into focus on the retina and would be interpreted by the brain as light from a distance closer to the eye 210 than optical infinity.

In some embodiments, a full color image may be formed at each depth plane by overlaying images in each of the component colors, e.g., three or more component colors. FIG. 8 illustrates an example of a stacked waveguide assembly in which each depth plane includes images formed using multiple different component colors. The illustrated embodiment shows depth planes 240a-240f, although more or fewer depths are also contemplated. Each depth plane may have three or more component color images associated with it, including: a first image of a first color, G; a second image of a second color, R; and a third image of a third color, B. Different depth planes are indicated in the figure by different numbers for diopters (dpt) following the letters G, R, and B. Just as examples, the numbers following each of these letters indicate diopters (1/m), or inverse distance of the depth plane from a viewer, and each box in the figures represents an individual component color image. In some embodiments, to account for differences in the eye's focusing of light of different wavelengths, the exact placement of the depth planes for different component colors may vary. For example, different component color images for a given depth plane may be placed on depth planes corresponding to different distances from the user. Such an arrangement may increase visual acuity and user comfort and/or may decrease chromatic aberrations.

In some embodiments, light of each component color may be outputted by a single dedicated waveguide and, consequently, each depth plane may have multiple waveguides associated with it. In such embodiments, each box in the figures including the letters G, R, or B may be understood to represent an individual waveguide, and three waveguides may be provided per depth plane where three component color images are provided per depth plane. While the waveguides associated with each depth plane are shown adjacent to one another in this drawing for ease of description, it will be appreciated that, in a physical device, the waveguides may all be arranged in a stack with one waveguide per level. In some other embodiments, multiple component colors may be outputted by the same waveguide, such that, e.g., only a single waveguide may be provided per depth plane.

With continued reference to FIG. 8, in some embodiments, G is the color green, R is the color red, and B is the color blue. In some other embodiments, other colors associated with other wavelengths of light, including magenta and cyan, may be used in addition to or may replace one or more of red, green, or blue.

It will be appreciated that references to a given color of light throughout this disclosure will be understood to encompass light of one or more wavelengths within a range of wavelengths of light that are perceived by a viewer as being of that given color. For example, red light may include light of one or more wavelengths in the range of about 620-780 nm, green light may include light of one or more wavelengths in the range of about 492-577 nm, and blue light may include light of one or more wavelengths in the range of about 435-493 nm.

In some embodiments, the light source 530 (FIG. 6) may be configured to emit light of one or more wavelengths outside the visual perception range of the viewer, for example, infrared and/or ultraviolet wavelengths. In addition, the in-coupling, out-coupling, and other light redirecting structures of the waveguides of the display 250 may be configured to direct and emit this light out of the display towards the user's eye 210, e.g., for imaging and/or user stimulation applications.

Figure 9A:
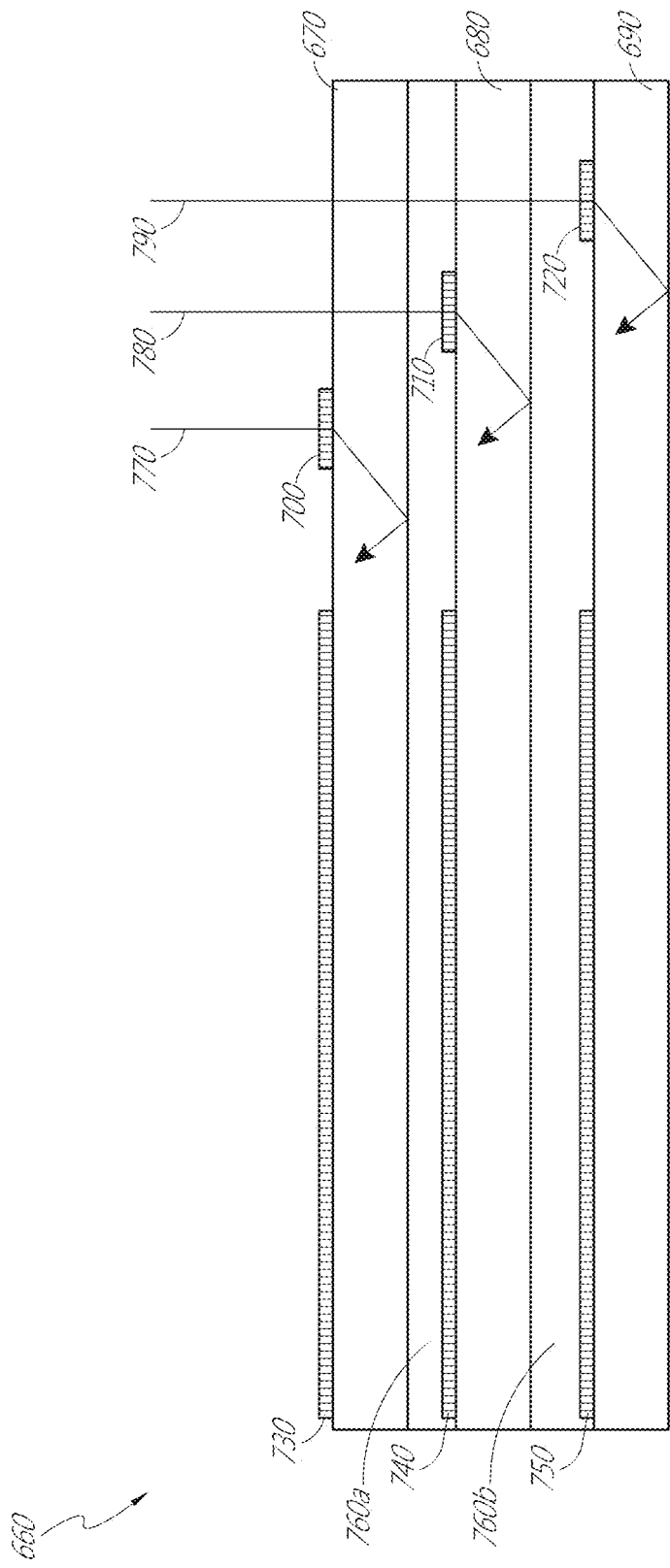
FIG. 9A illustrates a cross-sectional side view of an example of a set of stacked waveguides that each includes an incoupling optical element.

With reference now to FIG. 9A, in some embodiments, light impinging on a waveguide may need to be redirected to in-couple that light into the waveguide. An in-coupling optical element may be used to redirect and in-couple the light into its corresponding waveguide. FIG. 9A illustrates a cross-sectional side view of an example of a plurality or set 660 of stacked waveguides that each includes an in-coupling optical element. The waveguides may each be configured to output light of one or more different wavelengths, or one or more different ranges of wavelengths. It will be appreciated that the stack 660 may correspond to the stack 260 (FIG. 6) and the illustrated waveguides of the stack 660 may correspond to part of the plurality of waveguides 270, 280, 290, 300, 310, except that light from one or more of the image injection devices 360, 370, 380, 390, 400 is injected into the waveguides from a position that requires light to be redirected for in-coupling.

The illustrated set 660 of stacked waveguides includes waveguides 670, 680, and 690. Each waveguide includes an associated in-coupling optical element (which may also be referred to as a light input area on the waveguide), with, e.g., in-coupling optical element 700 disposed on a major surface (e.g., an upper major surface) of waveguide 670, in-coupling optical element 710 disposed on a major surface (e.g., an upper major surface) of waveguide 680, and in-coupling optical element 720 disposed on a major surface (e.g., an upper major surface) of waveguide 690. In some embodiments, one or more of the in-coupling optical elements 700, 710, 720 may be disposed on the bottom major surface of the respective waveguide 670, 680, 690 (particularly where the one or more in-coupling optical elements are reflective, deflecting optical elements). As illustrated, the in-coupling optical elements 700, 710, 720 may be disposed on the upper major surface of their respective waveguide 670, 680, 690 (or the top of the next lower waveguide), particularly where those in-coupling optical elements are transmissive, deflecting optical elements. In some embodiments, the in-coupling optical elements 700, 710, 720 may be disposed in the body of the respective waveguide 670, 680, 690. In some embodiments, as discussed herein, the in-coupling optical elements 700, 710, 720 are wavelength selective, such that they selectively redirect one or more wavelengths of light, while transmitting other wavelengths of light. While illustrated on one side or corner of their respective waveguide 670, 680, 690, it will be appreciated that the in-coupling optical elements 700, 710, 720 may be disposed in other areas of their respective waveguide 670, 680, 690 in some embodiments.

As illustrated, the in-coupling optical elements 700, 710, 720 may be laterally offset from one another. In some embodiments, each in-coupling optical element may be offset such that it receives light without that light passing through another in-coupling optical element. For example, each in-coupling optical element 700, 710, 720 may be configured to receive light from a different image injection device 360, 370, 380, 390, and 400 as shown in FIG. 6, and may be separated (e.g., laterally spaced apart) from other in-coupling optical elements 700, 710, 720 such that it substantially does not receive light from the other ones of the in-coupling optical elements 700, 710, 720.

Each waveguide also includes associated light distributing elements, with, e.g., light distributing elements 730 disposed on a major surface (e.g., a top major surface) of waveguide 670, light distributing elements 740 disposed on a major surface (e.g., a top major surface) of waveguide 680, and light distributing elements 750 disposed on a major surface (e.g., a top major surface) of waveguide 690. In some other embodiments, the light distributing elements 730, 740, 750, may be disposed on a bottom major surface of associated waveguides 670, 680, 690, respectively. In some other embodiments, the light distributing elements 730, 740, 750, may be disposed on both top and bottom major surface of associated waveguides 670, 680, 690, respectively; or the light distributing elements 730, 740, 750, may be disposed on different ones of the top and bottom major surfaces in different associated waveguides 670, 680, 690, respectively.

The waveguides 670, 680, 690 may be spaced apart and separated by, e.g., gas, liquid, and/or solid layers of material. For example, as illustrated, layer 760a may separate waveguides 670 and 680; and layer 760b may separate waveguides 680 and 690. In some embodiments, the layers 760a and 760b are formed of low refractive index materials (that is, materials having a lower refractive index than the material forming the immediately adjacent one of waveguides 670, 680, 690). Preferably, the refractive index of the material forming the layers 760a, 760b is 0.05 or more, or 0.10 or less than the refractive index of the material forming the waveguides 670, 680, 690. Advantageously, the lower refractive index layers 760a, 760b may function as cladding layers that facilitate total internal reflection (TIR) of light through the waveguides 670, 680, 690 (e.g., TIR between the top and bottom major surfaces of each waveguide). In some embodiments, the layers 760a, 760b are formed of air. While not illustrated, it will be appreciated that the top and bottom of the illustrated set 660 of waveguides may include immediately neighboring cladding layers.

Preferably, for ease of manufacturing and other considerations, the material forming the waveguides 670, 680, 690 are similar or the same, and the material forming the layers 760a, 760b are similar or the same. In some embodiments, the material forming the waveguides 670, 680, 690 may be different between one or more waveguides, and/or the material forming the layers 760a, 760b may be different, while still holding to the various refractive index relationships noted above.

With continued reference to FIG. 9A, light rays 770, 780, 790 are incident on the set 660 of waveguides. It will be appreciated that the light rays 770, 780, 790 may be injected into the waveguides 670, 680, 690 by one or more image injection devices 360, 370, 380, 390, 400 (FIG. 6).

In some embodiments, the light rays 770, 780, 790 have different properties, e.g., different wavelengths or different ranges of wavelengths, which may correspond to different colors. The in-coupling optical elements 700, 710, 720 each deflect the incident light such that the light propagates through a respective one of the waveguides 670, 680, 690 by TIR. In some embodiments, the incoupling optical elements 700, 710, 720 each selectively deflect one or more particular wavelengths of light, while transmitting other wavelengths to an underlying waveguide and associated incoupling optical element.

For example, in-coupling optical element 700 may be configured to deflect ray 770, which has a first wavelength or range of wavelengths, while transmitting rays 780 and 790, which have different second and third wavelengths or ranges of wavelengths, respectively. The transmitted ray 780 impinges on and is deflected by the in-coupling optical element 710, which is configured to deflect light of a second wavelength or range of wavelengths. The ray 790 is deflected by the in-coupling optical element 720, which is configured to selectively deflect light of third wavelength or range of wavelengths.

With continued reference to FIG. 9A, the deflected light rays 770, 780, 790 are deflected so that they propagate through a corresponding waveguide 670, 680, 690; that is, the in-coupling optical elements 700, 710, 720 of each waveguide deflects light into that corresponding waveguide 670, 680, 690 to in-couple light into that corresponding waveguide. The light rays 770, 780, 790 are deflected at angles that cause the light to propagate through the respective waveguide 670, 680, 690 by TIR. The light rays 770, 780, 790 propagate through the respective waveguide 670, 680, 690 by TIR until impinging on the waveguide's corresponding light distributing elements 730, 740, 750.

Figure 9B:
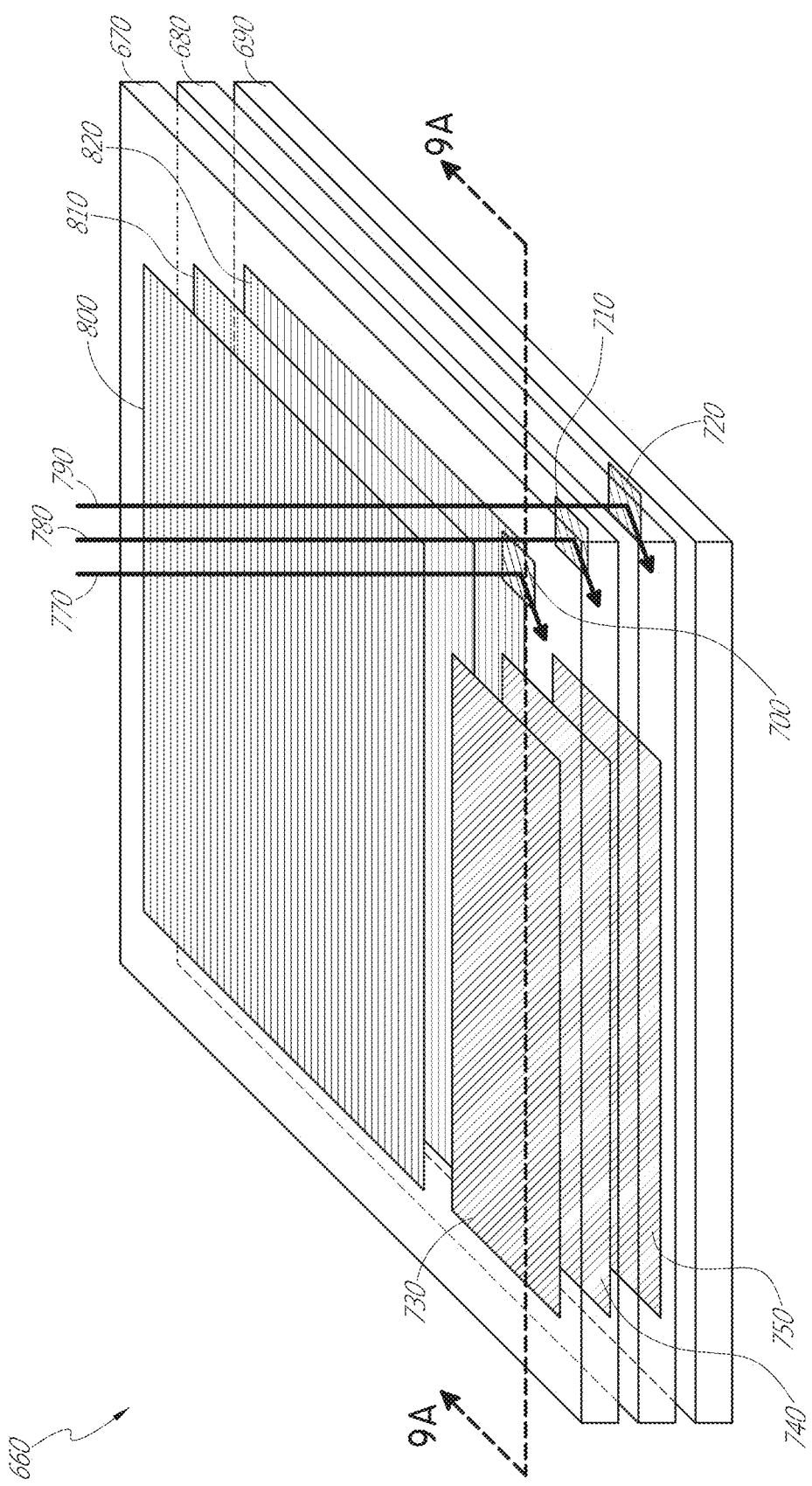
FIG. 9B illustrates a perspective view of an example of the plurality of stacked waveguides of FIG. 9A.

With reference now to FIG. 9B, a perspective view of an example of the plurality of stacked waveguides of FIG. 9A is illustrated. As noted above, the in-coupled light rays 770, 780, 790, are deflected by the in-coupling optical elements 700, 710, 720, respectively, and then propagate by TIR within the waveguides 670, 680, 690, respectively. The light rays 770, 780, 790 then impinge on the light distributing elements 730, 740, 750, respectively. The light distributing elements 730, 740, 750 deflect the light rays 770, 780, 790 so that they propagate towards the out-coupling optical elements 800, 810, 820, respectively.

In some embodiments, the light distributing elements 730, 740, 750 are orthogonal pupil expanders (OPE's). In some embodiments, the OPE's deflect or distribute light to the out-coupling optical elements 800, 810, 820 and, in some embodiments, may also increase the beam or spot size of this light as it propagates to the out-coupling optical elements. In some embodiments, the light distributing elements 730, 740, 750 may be omitted and the in-coupling optical elements 700, 710, 720 may be configured to deflect light directly to the out-coupling optical elements 800, 810, 820. For example, with reference to FIG. 9A, the light distributing elements 730, 740, 750 may be replaced with out-coupling optical elements 800, 810, 820, respectively. In some embodiments, the out-coupling optical elements 800, 810, 820 are exit pupils (EP's) or exit pupil expanders (EPE's) that direct light in a viewer's eye 210 (FIG. 7). It will be appreciated that the OPE's may be configured to increase the dimensions of the eye box in at least one axis and the EPE's may be to increase the eye box in an axis crossing, e.g., orthogonal to, the axis of the OPEs. For example, each OPE may be configured to redirect a portion of the light striking the OPE to an EPE of the same waveguide, while allowing the remaining portion of the light to continue to propagate down the waveguide. Upon impinging on the OPE again, another portion of the remaining light is redirected to the EPE, and the remaining portion of that portion continues to propagate further down the waveguide, and so on. Similarly, upon striking the EPE, a portion of the impinging light is directed out of the waveguide towards the user, and a remaining portion of that light continues to propagate through the waveguide until it strikes the EP again, at which time another portion of the impinging light is directed out of the waveguide, and so on. Consequently, a single beam of incoupled light may be "replicated" each time a portion of that light is redirected by an OPE or EPE, thereby forming a field of cloned beams of light, as shown in FIG. 6. In some embodiments, the OPE and/or EPE may be configured to modify a size of the beams of light.

Accordingly, with reference to FIGS. 9A and 9B, in some embodiments, the set 660 of waveguides includes waveguides 670, 680, 690; in-coupling optical elements 700, 710, 720; light distributing elements (e.g., OPE's) 730, 740, 750; and out-coupling optical elements (e.g., EP's) 800, 810, 820 for each component color. The waveguides 670, 680, 690 may be stacked with an air gap/cladding layer between each one. The in-coupling optical elements 700, 710, 720 redirect or deflect incident light (with different in-coupling optical elements receiving light of different wavelengths) into its waveguide. The light then propagates at an angle which will result in TIR within the respective waveguide 670, 680, 690. In the example shown, light ray 770 (e.g., blue light) is deflected by the first in-coupling optical element 700, and then continues to bounce down the waveguide, interacting with the light distributing element (e.g., OPE's) 730 and then the out-coupling optical element (e.g., EPs) 800, in a manner described earlier. The light rays 780 and 790 (e.g., green and red light, respectively) will pass through the waveguide 670, with light ray 780 impinging on and being deflected by in-coupling optical element 710. The light ray 780 then bounces down the waveguide 680 via TIR, proceeding on to its light distributing element (e.g., OPEs) 740 and then the out-coupling optical element (e.g., EP's) 810. Finally, light ray 790 (e.g., red light) passes through the waveguide 690 to impinge on the light in-coupling optical elements 720 of the waveguide 690. The light in-coupling optical elements 720 deflect the light ray 790 such that the light ray propagates to light distributing element (e.g., OPEs) 750 by TIR, and then to the out-coupling optical element (e.g., EPs) 820 by TIR. The out-coupling optical element 820 then finally out-couples the light ray 790 to the viewer, who also receives the out-coupled light from the other waveguides 670, 680.

Figure 9C:
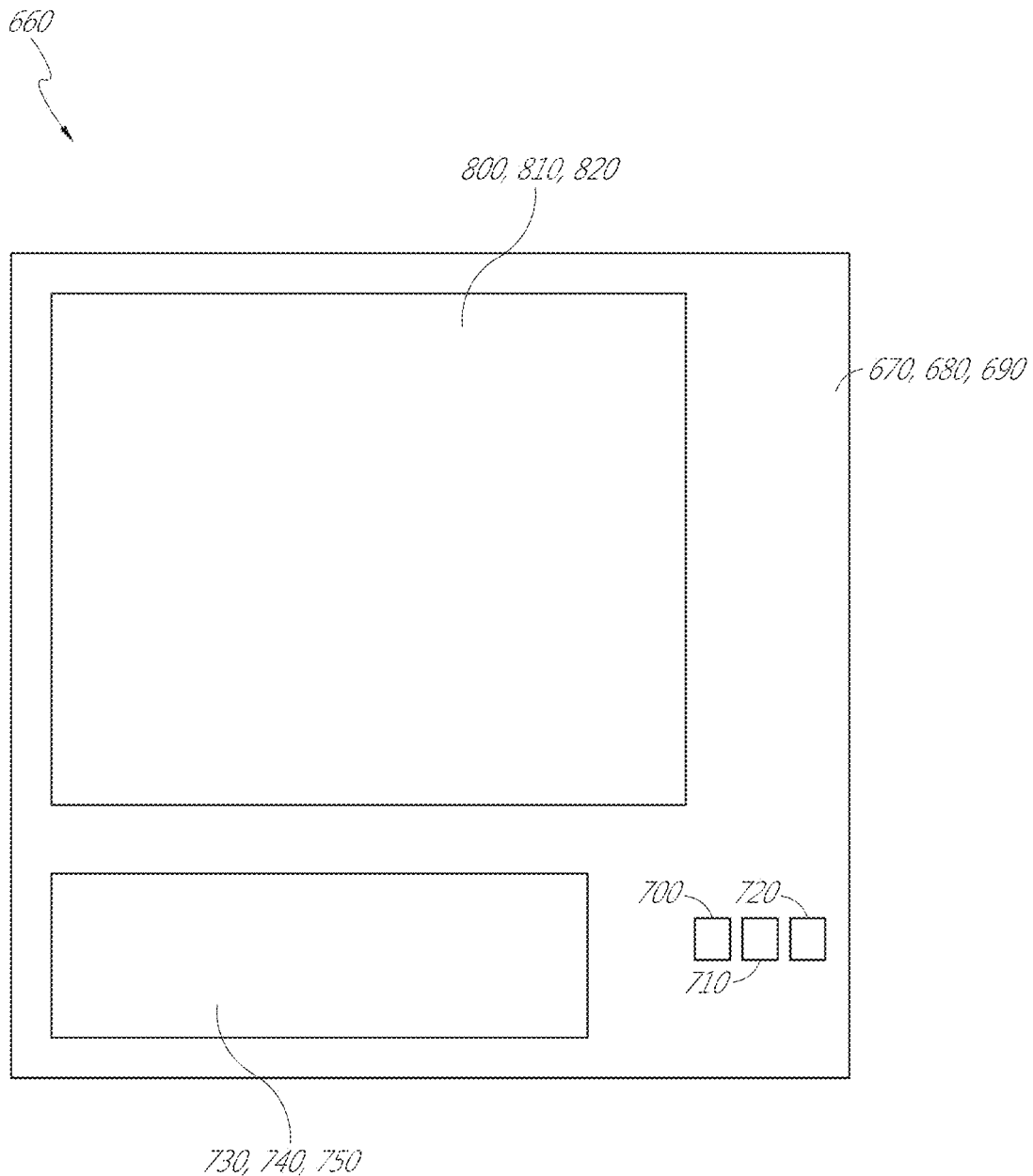
FIG. 9C illustrates a top-down plan view of an example of the plurality of stacked waveguides of FIGS. 9A and 9B.

FIG. 9C illustrates a top-down plan view of an example of the plurality of stacked waveguides of FIGS. 9A and 9B. As illustrated, the waveguides 670, 680, 690, along with each waveguide's associated light distributing element 730, 740, 750 and associated out-coupling optical element 800, 810, 820, may be vertically aligned. However, as discussed herein, the in-coupling optical elements 700, 710, 720 are not vertically aligned; rather, the in-coupling optical elements are preferably non-overlapping (e.g., laterally spaced apart as seen in the top-down view). As discussed further herein, this nonoverlapping spatial arrangement facilitates the injection of light from different resources into different waveguides on a one-to-one basis, thereby allowing a specific light source to be uniquely coupled to a specific waveguide. In some embodiments, arrangements including nonoverlapping spatially-separated in-coupling optical elements may be referred to as a shifted pupil system, and the in-coupling optical elements within these arrangements may correspond to sub pupils.

Figure 9D:
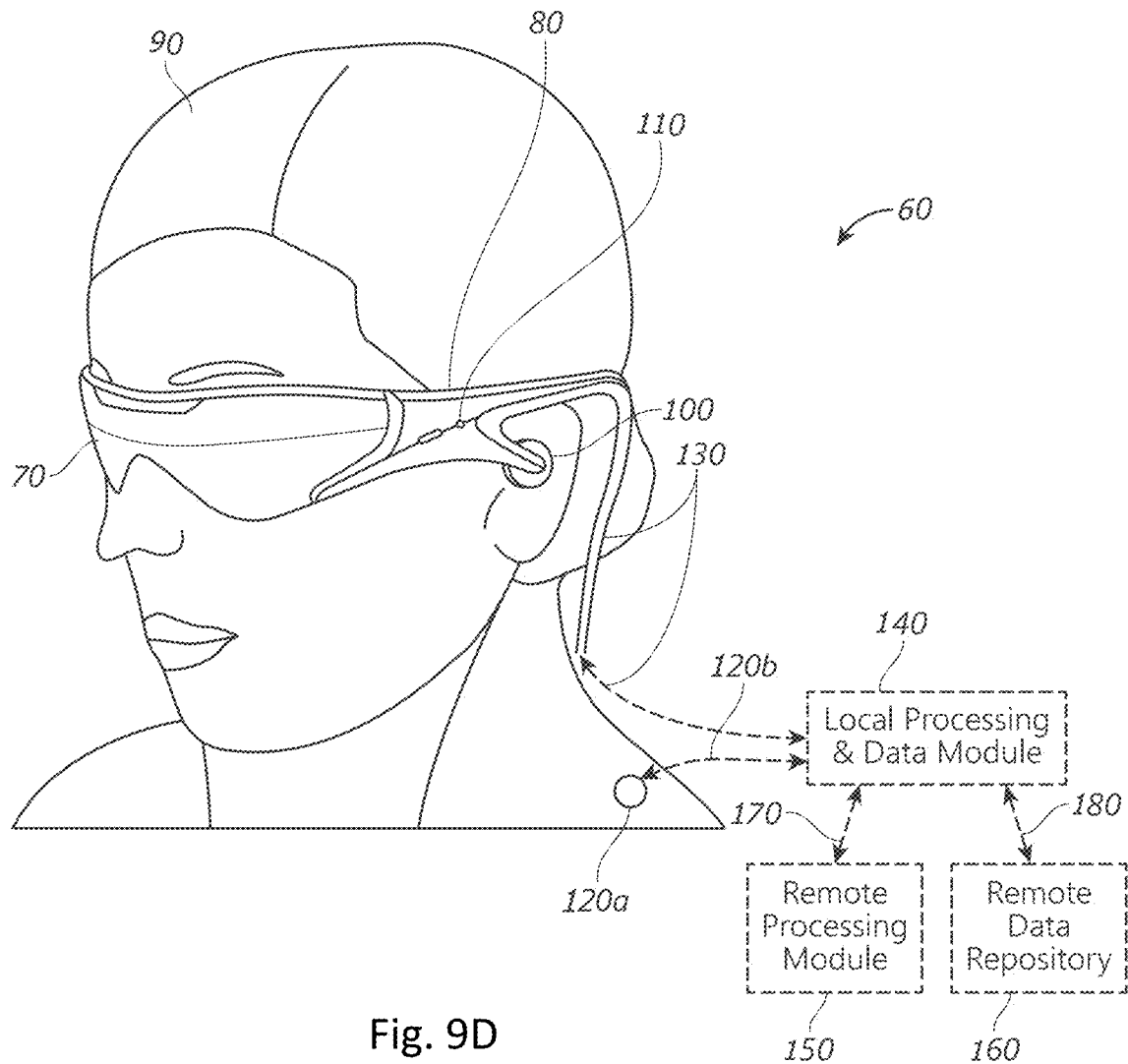
FIG. 9D illustrates an example of wearable display system.

FIG. 9D illustrates an example of wearable display system 60 into which the various waveguides and related systems disclosed herein may be integrated. In some embodiments, the display system 60 is the system 250 of FIG. 6, with FIG. 6 schematically showing some parts of that system 60 in greater detail. For example, the waveguide assembly 260 of FIG. 6 may be part of the display 70.

With continued reference to FIG. 9D, the display system 60 includes a display 70, and various mechanical and electronic modules and systems to support the functioning of that display 70. The display 70 may be coupled to a frame 80, which is wearable by a display system user or viewer 90 and which is configured to position the display 70 in front of the eyes of the user 90. The display 70 may be considered eyewear in some embodiments. In some embodiments, a speaker 100 is coupled to the frame 80 and configured to be positioned adjacent the ear canal of the user 90 (in some embodiments, another speaker, not shown, may optionally be positioned adjacent the other ear canal of the user to provide stereo/shapeable sound control). The display system 60 may also include one or more microphones 110 or other devices to detect sound. In some embodiments, the microphone is configured to allow the user to provide inputs or commands to the system 60 (e.g., the selection of voice menu commands, natural language questions, etc.), and/or may allow audio communication with other persons (e.g., with other users of similar display systems. The microphone may further be configured as a peripheral sensor to collect audio data (e.g., sounds from the user and/or environment). In some embodiments, the display system may also include a peripheral sensor 120*a*, which may be separate from the frame 80 and attached to the body of the user 90 (e.g., on the head, torso, an extremity, etc. of the user 90). The peripheral sensor 120*a* may be configured to acquire data characterizing a physiological state of the user 90 in some embodiments. For example, the sensor 120*a* may be an electrode.

With continued reference to FIG. 9D, the display 70 is operatively coupled by communications link 130, such as by a wired lead or wireless connectivity, to a local data processing module 140 which may be mounted in a variety of configurations, such as fixedly attached to the frame 80, fixedly attached to a helmet or hat worn by the user, embedded in headphones, or otherwise removably attached to the user 90 (e.g., in a backpack-style configuration, in a belt-coupling style configuration). Similarly, the sensor 120*a* may be operatively coupled by communications link 120*b*, e.g., a wired lead or wireless connectivity, to the local processor and data module 140. The local processing and data module 140 may comprise a hardware processor, as well as digital memory, such as non-volatile memory (e.g., flash memory or hard disk drives), both of which may be utilized to assist in the processing, caching, and storage of data. Optionally, the local processor and data module 140 may include one or more central processing units (CPUs), graphics processing units (GPUs), dedicated processing hardware, and so on. The data may include data a) captured from sensors (which may be, e.g., operatively coupled to the frame 80 or otherwise attached to the user 90), such as image capture devices (such as cameras), microphones, inertial measurement units, accelerometers, compasses, GPS units, radio devices, gyros, and/or other sensors disclosed herein; and/or b) acquired and/or processed using remote processing module 150 and/or remote data repository 160 (including data relating to virtual content), possibly for passage to the display 70 after such processing or retrieval. The local processing and data module 140 may be operatively coupled by communication links 170, 180, such as via a wired or wireless communication links, to the remote processing module 150 and remote data repository 160 such that these remote modules 150, 160 are operatively coupled to each other and available as resources to the local processing and data module 140. In some embodiments, the local processing and data module 140 may include one or more of the image capture devices, microphones, inertial measurement units, accelerometers, compasses, GPS units, radio devices, and/or gyros. In some other embodiments, one or more of these sensors may be attached to the frame 80, or may be standalone structures that communicate with the local processing and data module 140 by wired or wireless communication pathways.

With continued reference to FIG. 9D, in some embodiments, the remote processing module 150 may comprise one or more processors configured to analyze and process data and/or image information, for instance including one or more central processing units (CPUs), graphics processing units (GPUs), dedicated processing hardware, and so on. In some embodiments, the remote data repository 160 may comprise a digital data storage facility, which may be available through the internet or other networking configuration in a "cloud" resource configuration. In some embodiments, the remote data repository 160 may include one or more remote servers, which provide information, e.g., information for generating augmented reality content, to the local processing and data module 140 and/or the remote processing module 150. In some embodiments, all data is stored and all computations are performed in the local processing and data module, allowing fully autonomous use from a remote module. Optionally, an outside system (e.g., a system of one or more processors, one or more computers) that includes CPUs, GPUs, and so on, may perform at least a portion of processing (e.g., generating image information, processing data) and provide information to, and receive information from, modules 140, 150, 160, for instance via wireless or wired connections.

Figure 9E:
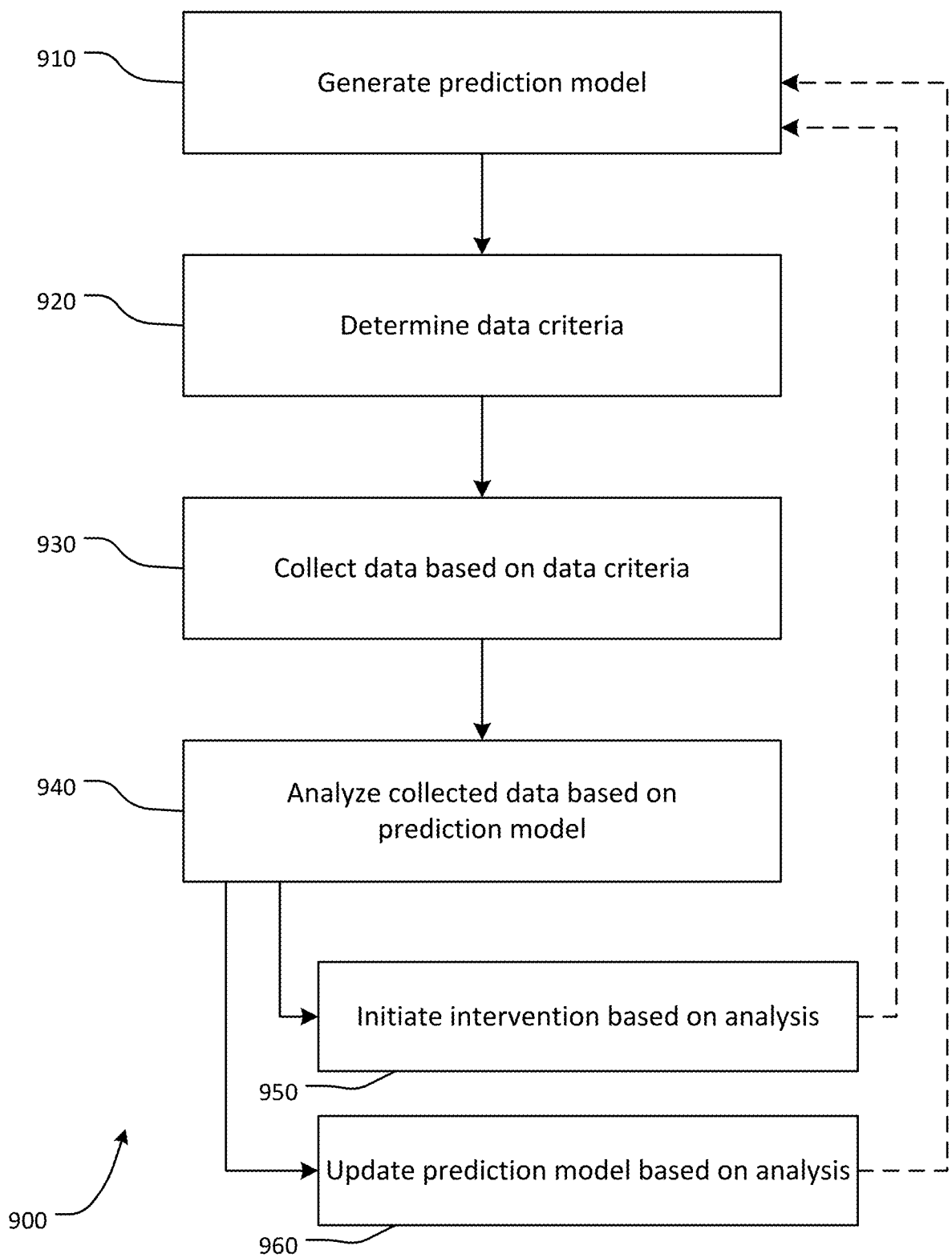
FIG. 9E illustrates an example of a method of data collection and analysis.

Referring now to FIG. 9E, the display systems described herein may be used for collection and analysis of data. FIG. 9E illustrates an example method 900 for the collection and analysis of data in accordance with various embodiments.

The method 900 begins at block 910, in which a prediction model is generated. The prediction model may include one or more criteria for determining an outcome based on collected data. For example, the prediction model may include one or more methods for determining if a user has a symptom, condition, disorder, or the like, based on one or more criteria or variables, which may be detected by a display system and/or determined based on data obtained by the display system. The prediction model may be generated, for example, based on sources such as scientific and/or medical literature, published studies providing correlations between physiological, neurological, and/or behavioral data and outcomes such as symptoms or conditions, or the like. Generally, the prediction model may include specified variables to be analyzed, as well as weighting factors for the analysis of the variables. In one example, a prediction model may be generated for detecting the condition of depression. Existing research related to depression may indicate that depression has a certain number, e.g., 9, identified symptoms, and that a diagnosis of depression may be based on the presence of another particular number, e.g., 5, of the 9 symptoms for a particular duration, e.g., at least 2 weeks. Thus, a prediction model for depression may provide for a determination that a user has depression if the user exhibits 5 or more of the 9 identified symptoms (some or all of which may be detectable directly or indirectly by one or more sensors of a display system) for 2 or more consecutive weeks. After a prediction model is generated, the method 900 continues to block 920. It will be appreciated that generating the prediction model may include providing or programming the prediction model into the display system. For example, the prediction model may be pre-programmed or otherwise provided to the display system before data collection begins.

At block 920, data criteria are determined to control and/or guide the collection of data for evaluation of the prediction model. For example, the data criteria may include a quantity of data (e.g., number of data points, total time of data collection, etc.), sufficient to yield a reliable outcome based on the prediction model. In one example, the quantity of data to be collected for an analysis may be the number of data points sufficient to yield an outcome with a reliability higher than chance level (e.g., 50%), with a maximum of 10% type 1 (false positive) error and a maximum of 10% type 2 (false negative) error. In some other embodiments, larger or smaller margins of error may be allowable based on requirements for determination of an outcome in a particular prediction model. The data criteria may further specify individual quantities for particular variables within the prediction model. Generally, the data criteria may specify that data will be collected for at least one user for at least one time period for at least one data type. In some embodiments, the data criteria may further include additional users (e.g., to obtain a larger sample size), additional data types (e.g., based on different data sources such as multiple sensors of the display system), and/or a longer time period (e.g., data for one or more users over a longer time period). Such extensions of the data criteria may be determined based on the type of data to be measured, e.g., data for particular physiological or behavioral phenomena, and/or based on the type of outcome to be produced (e.g., diagnosis of a condition, etc.). After data criteria are determined, the method 900 continues to block 930.

At block 930, data collection occurs based on the data criteria. For example, the display systems may be configured to collect data in accordance with the data criteria. In various embodiments, at least a specified number of data points may be collected. In some embodiments, data points can be collected at regular or irregular intervals for at least a specified time period to satisfy the data criteria. In some embodiments, the data points are collected continuously when the user wears the display device. Additionally, in some embodiments, a certain number or duration of data may be collected for at least a specified number of users. After sufficient data are collected based on the data criteria, the method 900 continues to block 940.

At block 940, the collected data are analyzed based on the prediction model. Generally, the analysis of the collected data produces an outcome (e.g., a class label, value, threshold, or the like) based on a classification, regression model, or other method of analysis as specified in the prediction model. In some embodiments, analysis of the collected data may include any known statistical analysis methods (e.g., R-squared, chi-squared, or other statistical tests or analysis methods). Based on the prediction model, a label may be applied to the output of the analysis. For example, the label may include one or more categorizations of symptoms or conditions, a determination that a particular symptom or condition is present, or the like. After the collected data have been analyzed, the method 900 may proceed to block 950 and/or block 960 based on the outcome of the data analysis.

At block 950, an intervention is conducted based on the analysis. For example, if a result of the data analysis is a determination of a symptom or condition for which a therapeutic or other intervention should be implemented, such intervention may occur based on the analysis.

At block 960, the prediction model is updated based on the analysis. For example, the results of the analysis may indicate that the data criteria and/or aspects of the prediction model should be revised to enhance the accuracy of the model. In some embodiments, updates to the model may include changes in the variables to be analyzed, relative weighting of the variables, quantity of data to be collected, or the like. In various embodiments, either or both of blocks 950 and 960 may be implemented based on a particular outcome of the analysis of block 940. After either block 950 or block 960, the method 900 may return to block 910, where the method 900 may be repeated any number of times for further user health analysis and refinement of analysis results and updating of the prediction model.

As an example, the method 900 may be implemented for diagnosis and/or modification of treatment of depression. For example, the initial prediction model of block 910 may include 9 identified symptoms of depression, where the presence of 5 or more of the 9 symptoms for 2 or more consecutive weeks indicates a diagnosis of depression. The initial prediction model may further include types of analysis to be used, such as a logistics regression analysis or other statistical analyses. In addition, the prediction model may include one or more population subgroups (e.g., Parkinson's disease or other groups) based on input data type (e.g., eye tracking data or the like). At block 920, the method 900 may determine the quantity and type of data to be collected in order to perform the analysis. For example, the data criteria may include a specified number of data points per minute, hour, day week, etc., and may further include that the data points should be collected over a time period of, e.g., 2 weeks or more, based on the pre-programmed prediction model. The data criteria may additionally include particular types of data points to be collected, for example, based on specified sensors of the display system.

Data may then be collected in accordance with the data criteria at block 930. For example, the display system may begin collecting data until the quantity and/or time period of data collection satisfy the data criteria. After the data are collected the data may be analyzed at block 940 based on the prediction model. For example, the display system may perform one or more statistical analyses as described herein to determine whether the collected data indicate, to a specified confidence interval, that the user has 5 or more of the specified depression symptoms for a period of 2 or more weeks. The output of the statistical analyses may then be labeled to indicate whether the user is determined to have depression or not to have depression. For therapeutic implementations, the method 900 may continue to block 950, in which an intervention is initiated based on the labeled analysis output. For example, the intervention may include calling a doctor, implementing a real-time intervention via the display system to mitigate one or more symptoms of depression, notifying the user, creating a log, or the like. After initiating an intervention, the method 900 may return to block 910 to continue ongoing monitoring for symptoms of depression.

In another example, the method 900 may be implemented to improve knowledge of indicators in a prediction model and/or the enhancement of prediction methods (e.g., improving algorithms of the display device, aggregating data and updating the prediction model for enhance reliability, accuracy, and/or validity, etc.). One or more initial prediction models may be generated and data criteria may be generated consistent with the description of blocks 910 and 920 above. Data may be collected and analyzed to determine an analysis output consistent with blocks 930 and 940 above. After the data are analyzed, the method 900 may continue to block 960, in which the prediction model is analyzed and/or revised based on the output of the analysis at block 940. For example, the initial prediction model may be evaluated (e.g., based on statistical power analysis or the like) to determine if the selected variables are the correct variables to be included in the prediction model, if any variables should be added to and/or removed from the model, whether the weights accorded to each variable are correct, etc. After revisions to the initial prediction model are identified, the method may return to block 910, where the model is revised, and the method may continue to block 920 for further analysis consistent with the revised model. It will be appreciated that any or combinations of or all of blocks 910-960 may be performed locally in a local processing module (which may include at least a memory and a hardware processor wearable by the user) and/or may be performed in a remote processing module (50, FIG. 9D) that includes one or more hardware processors. In addition, computer programming comprising instructions for performing any or combinations of or all of blocks 910-960 may be stored locally in a data module and/or a remote data repository (50, FIG. 9D).

In some embodiments, the system 60 may manipulate accommodation and vergence, such as for user monitoring, data collection, diagnosis, or therapy. In one example, the system 60 may display visual content to the user 90 with proper accommodation and vergence, and may collect data including a neurological response such as electrical activity (e.g., measured by EEG), and/or a physiological response such as a blood pressure, breath rate, pupil dilation/contraction, or other signs. In addition or alternatively, the system 60 may manipulate visual content delivered to a user 90 so as to establish more or less accommodation-vergence mismatch, and may collect similar data. In some aspects, user-specific data such as neurological and/or physiological data collected from the user 90 may accordingly be used to determine whether the system 60 and display 70 are providing proper accommodation and vergence, or if adjustments should be made to improve viewer comfort, such as for long-term wearing comfort.

Figure 10:
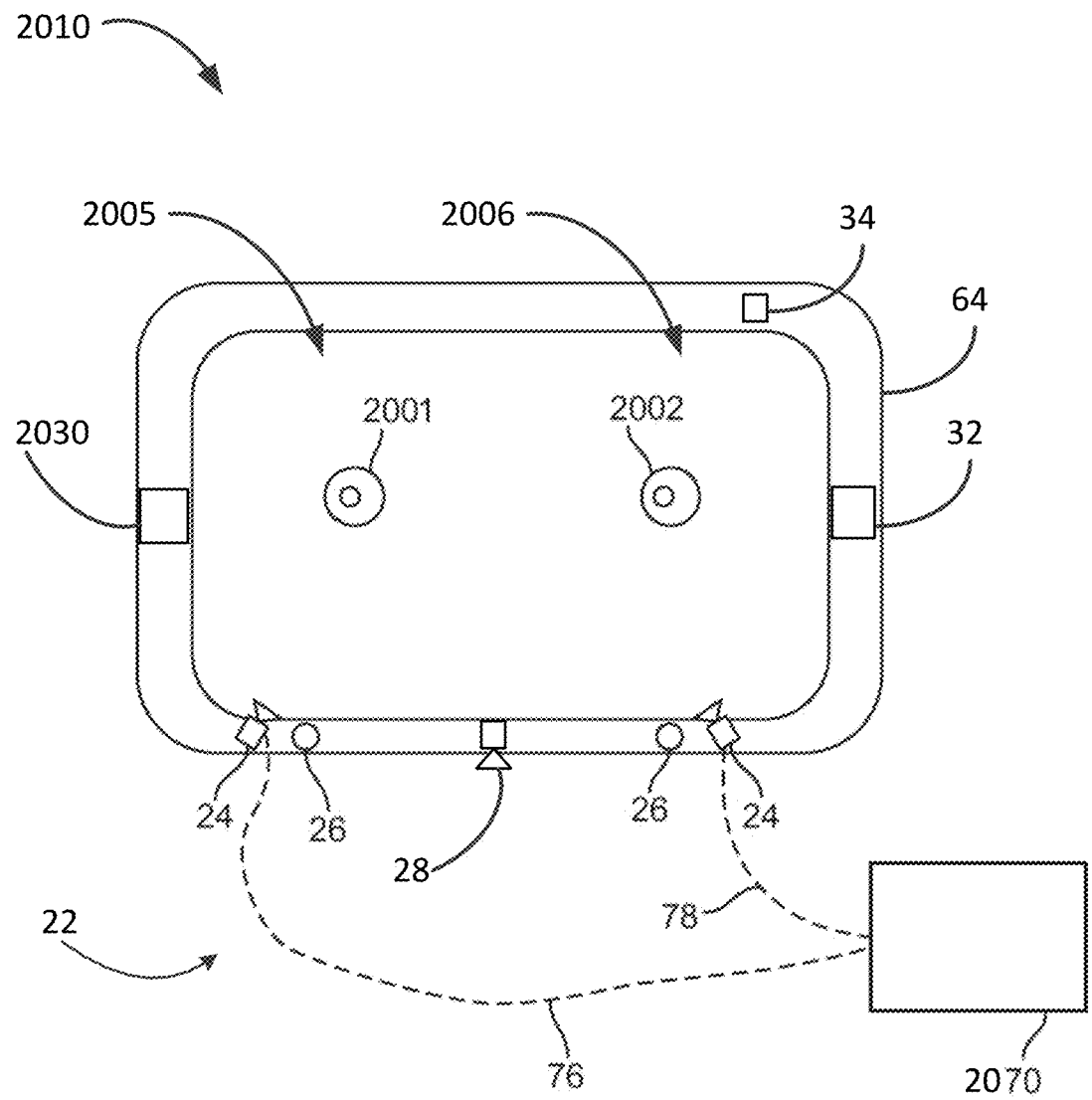
FIG. 10 shows a schematic view of an example of various components of an augmented reality system comprising environmental and user sensors.

Reference will now be made to FIG. 10, which shows a schematic view of an example of various components of an augmented reality display system comprising user sensors 24, 28, 2030, 32 and environmental sensors 34. In some embodiments, the augmented reality display system may be a mixed reality display system. As shown, the user sensors 24, 28, 2030, 32 may be configured to detect data regarding the state of the user, and the environmental sensors 34 may be configured to collect data regarding parameters external to the user. In some embodiments, the display system may be configured to store data related to and/or characterizing virtual content delivered to the user (e.g., the time, location, color make-up, sound volume etc., of the virtual content).

The user sensors will be discussed first. As illustrated, an augmented reality display system 2010 may include various user sensors. The augmented reality display system 2010 may correspond to the system 60 of FIG. 9D and may include a viewer imaging system 22. The system 22 may include cameras 24 (e.g., infrared, UV, other non-visible light, and/or visible light cameras) paired with light sources 26 (e.g., infrared light sources) directed at and configured to monitor the user (e.g., the eyes 2001, 2002 and/or surrounding tissues of the user). These cameras 24 and light sources 26 may be operatively coupled to the local processing module 70. Such cameras 24 may be configured to monitor one or more of the orientation, shape, and symmetry of pupils (including pupil sizes), irises, or other structures of the respective eyes, and/or tissues surrounding the eye, such as eyelids or eyebrows.

In some embodiments, imaging of the pupil, iris, and/or tissues surrounding the eye or eyeball may be used to monitor various autonomic system functions, which may be used to determine neural responses. For example, rhythmic dilation and constriction of the pupil may be correlated with the contraction and relaxation of the heart. Accordingly, the rhythmic dilation and constriction of the pupil may be used to monitor and/or detect abnormalities in the heart rate of the user. The period of the rhythmic dilation and constriction of the pupil (e.g., time interval between two consecutive dilations of the pupil) and/or amplitude (e.g., spacing between a dilation and a constriction) may be correlated to various autonomic functions such as heart rate. Some embodiments of the system may be configured to monitor and/or detect abnormalities in blood pressure and/or vasculature of the user. For example, the system may be configured to sense and/or measure minute corneal displacements that occur along a direction parallel to the optical axis of the user's eye as a result of pulsations caused by blood pressure behind the eye. The system may be configured to compare the measured minute corneal displacement values with one or more values of minute corneal displacements that indicate normal blood pressure or vascular function. Abnormalities in the blood pressure of the user and/or vascular function of the user may be detected if the measured minute corneal displacement values deviate from the one or more values of minute corneal displacements that indicate normal blood pressure or vascular function.

In some embodiments, imaging of the iris and/or retina of an eye may be used for secure identification of a user. As discussed herein, it will be appreciated that user-specific data, such as that related to the eyes, may be used to infer the behavioral or emotional state of the user. For example, widened eyes may be used to infer shock or a scrunched brow could be used to infer confusion. Moreover, the behavioral or emotional state of the user may further be triangulated with collected environmental and virtual content data to determine relationships between the behavioral or emotional state, user-specific data, and environmental or virtual content data. For example, the system may be configured to recognize certain patterns of facial muscle and tissue movement as, e.g., a scrunched brow, whether they are noticeable facial behaviors, expressions, or microexpressions, which, by itself or possibly in conjunction with other detected physiological and/or environmental data, may be recognized by the system to infer confusion by the user in an environment where the system detects that new subject matter is being taught in a classroom. This inference may advantageously be applied as an instructional aide to improve the lesson by showing that a student does not understand the teacher or the concept being taught. Similarly, the system may be configured to recognize widened eyes as indicating shock in the user, particularly where environmental sensors detect a loud noise, such as a gunshot.

With continued reference to FIG. 10, cameras 24 may further be configured to image the retinas of the respective eyes, such as for diagnostic purposes and/or for orientation tracking based on the location of retinal features, such as the fovea or features of the fundus. Iris and retina imaging or scanning may be performed for secure identification of users for, e.g., correctly associating user data with a particular user and/or to present private information to the appropriate user. In some embodiments, in addition to or as an alternative to the cameras 24, one or more cameras 28 may be configured to detect and/or monitor various other aspects of the status of a user. For example, one or more cameras 28 may be inward-facing and configured to monitor the shape, position, and/or movement of features other than the eyes of the user, e.g., one or more facial features (e.g., facial expression, voluntary movement, involuntary tics), or other features such as skin pallor as a sign of fatigue or sickness. In another example, one or more cameras 28 may be downward-facing and configured to monitor the position and/or movement of the arms, hands, legs, feet, and/or torso of a user. Downward-facing cameras and/or inertial measurement units may be able to detect body posture or body language, may be able to detect whether a user is sitting, standing, lying down, or in another position, and/or may be able to monitor a user's gait while the user walking or running so as to detect speed, gait abnormalities, or other information. In a further example, the display system may be configured to analyze images of the user's skin captured by the downward-facing cameras and perform an image analysis of the images to determine various conditions apparent from visual observations of the skin. For example, the images may be amplified (e.g., magnified and/or the intensities of particular colors may be increased) to allow visualization of blood flow. Such a visualization may be provided to the user as augmented reality content, or may be provided to a third party or other entity. As another example, the downward-facing camera may monitor dryness or wetness of the skin by, e.g., making determinations regarding the optical reflectivity of the skin, with higher reflectivity correlated with increased wetness. In some aspects, downward, inward, and/or outward-facing cameras described herein may be adjustable by a user and/or electronically by the system 22. For example, the outward facing camera may be configured to point forwards, to track the line of sight of the user, and may also be configured to rotate to, e.g., capture images orthogonal to the line of sight of the user.

In some embodiments, as disclosed herein, the display system 2010 may include a spatial light modulator that variably projects, through a fiber scanner (e.g., the image injection devices 200, 202, 204, 206, 208), light beams across the retina of the user to form an image. In some embodiments, the fiber scanner may be used in conjunction with, or in place of, the cameras 28 or 28 to, e.g., track or image the user's eyes. For example, as an alternative to or in addition to the scanning fiber being configured to output light, the health system may have a separate light-receiving device to receive light reflected from the user's eyes, and to collect data associated with that reflected light. In some embodiments, the light-receiving device may be a fiber scanner configured to collect light. Some configurations may include a first fiber scanner configured to project light for forming images and a second fiber scanner configured to collect light. In yet other embodiments, the same fiber scanner may be used to both provide light for forming images and to collect light for imaging purposes. For example, the fiber scanner may output light and collect light in a temporally multiplexed fashion, with the output and collection of light occurring at different times. The fibers of the fiber scanner may be connected to a spatial light modulator (for outputting light) and a light sensor (for collecting light for imaging), with an intervening beam splitter in the optical paths between the fibers and the spatial light modulator and light sensor, respectively.

With continued reference to FIG. 10, the cameras 24, 28 and light sources 26 may be mounted on the frame 64, which may also hold the waveguide stacks 2005, 2006. In some embodiments, sensors and/or other electronic devices (e.g., the cameras 24, 28 and light sources 26) of the display system 2010 may be configured to communicate with the local processing and data module 2070 through communication links 76, 78.

In some embodiments, in addition to providing data regarding the user, one or both of the cameras 24 and 28 may be utilized to track one or both eyes as a means to control virtual content provided to the user. For example, the eye-tracking system 22 may be utilized to select items on virtual menus, and/or provide other input to the display system 2010.

In some embodiments, the display system 2010 may include other sensors and/or stimulators 2030 configured to monitor physiological and/or behavioral aspects of the user. For example, such sensors and/or stimulators 2030 may include one or more of the sensors noted below, and/or stimulators such as transducers or actuators for heating, cooling, inducing vibration, etc. Examples of such sensors 2030 include sensors configured for ophthalmic testing such as confocal microscopy sensors, electronystagmography (ENG) sensors, electrooculography (EOG), electroretinography (ERG) sensors, laser Doppler flowmetry (LDF) sensors, photoacoustic imaging and pressure reading sensors, two-photon excitation microscopy sensors, and/or ultrasound sensors. Other examples of sensors 2030 include sensors configured for other electrodiagnostic technologies, such as electrocardiography (ECG) sensors, electroencephalography (EEG) sensors, electromyography (EMG) sensors, electrophysiological testing (EP) sensors, event-related potential (ERP) sensors, functional near-infrared spectroscopy (fNIR) sensors, low-resolution brain electromagnetic tomography (LORETA) sensors, and/or optical coherence tomography (OCT) sensors. Yet other examples of sensors 2030 include additional physiological sensors such as blood glucose meters, blood pressure meters, electrodermal activity sensors, photoplethysmography equipment, sensing equipment for computer-aided auscultation, and/or a body temperature sensor. In some embodiments, the display system 2010 may include motion sensors 32, such as one or more accelerometers, gyros, gesture sensors, gait sensors, balance sensors, and/or IMU sensors. Sensors 2030 may also include $CO_2$ monitoring sensors, respiratory rate sensors, end-title $CO_2$ sensors, and/or breathalyzers. The sensors 2030 may include one or more inwardly directed (user directed) microphones configured to detect sounds, and various properties of those sounds, including the intensity and type of sounds detected, the presence of multiple signals, signal location, voice, tone of voice, voice patterns, chewing, coughing, breathing, pulse, heart sounds, etc. In some aspects, sensors 2030 may include one or more sensors configured to perform echolocation, for example, directed at the mouth to analyze chewing of different foods or directed at the heart to analyze cardiac sounds.

The sensors 2030 are schematically illustrated as being connected to the frame 64. It will be appreciated that this connection may take the form of a physical attachment to the frame 64 and may be anywhere on the frame 64, including the ends of the temples of the frame 64 which extend over the user's ears. For example, the sensors 2030 may be mounted at the ends of the temples of the frame 64, at a point of contact between the frame 64 and the user. In some other embodiments, the sensors 2030 may extend away from the frame 64 to contact the user 60. In yet other embodiments, the sensors 2030 may not be physically attached to the frame 64; rather, the sensors 2030 may take the form of peripheral sensors 120a (FIG. 9D), which may be spaced apart from the frame 64. An example of peripheral sensor is an ultrasound probe, which may also be used to provide haptic feedback.

In some embodiments, the display system 2010 may further include one or more environmental sensors 34 configured to detect objects, stimuli, people, animals, locations, or other aspects of the world around the user. For example, environmental sensors 34 may include one or more cameras, altimeters, barometers, chemical sensors, humidity sensors, temperature sensors, external microphones, thermal imaging sensor, timing devices (e.g., clocks or calendars), or any combination or subcombination thereof. In some embodiments, multiple (e.g., two) microphones may be provided spaced-apart, to facilitate sound signal location determinations. For example, the emission and subsequent detection of reflected sound may be utilized for location determinations, such as echolocation. For example, a size and/or location of an object may be determined based on the detection of a sound emitted from the location of the user (e.g., by the user clapping and/or by the emission of a sound a speaker on the display system 2010), combined with time of flight (the time elapsed between emission of the sound and receipt of the subsequent reflection or echo) and directional information determined from external microphones that receive a reflection of that emitted sound. It will be appreciated that the distance between the object and the user increases with increases in elapsed time, while the size of the object increases with the magnitude or loudness of the echo.

In some embodiments, the display system 2010 may further be configured to receive other environmental inputs, such as GPS location data, weather data, date and time, or other available environmental data which may be received from the internet, satellite communication, or other suitable wired or wireless data communication method. The processing module 2070 may be configured to access further information characterizing a location of the user, such as pollen count, demographics, air pollution, environmental toxins, information from smart thermostats, lifestyle statistics, or proximity to other users, buildings, or a healthcare provider. In some embodiments, information characterizing the location may be accessed using cloud-based or other remote databases. The processing module 2070 may be configured to obtain such data and/or to further analyze data from any one or combination of the environmental sensors. For example, the processing module 2070 may be configured to use information from an outward-facing camera to identify and analyze food, drug, nutrients, and toxins that the user intakes. Similarly, a microphone may capture sounds indicative of chewing by the user and the processor may be configured to determine that the user is chewing food. It will be appreciated that eating of food may be associated with various changes in physiological state or part of a therapy regimen and, as such, the timing of food intake may be a useful variable to take into account when diagnosing and/or treating various health conditions. As will be described in greater detail herein, data from the various environmental sensors and/or other inputs such as information characterizing visual and/or auditory content delivered to the user, as well as the further analysis based on this data, may be combined with data from the physiological sensors described above to carry out health analyses and/or to modify therapies. The data may also be used to determine behavioral and/or emotional states of a user based on the relationships of the environmental and user-specific data.

The display system 2010 may be configured to collect and store data obtained through any of the sensors and/or inputs described above for extended periods of time. Data received at the device may be processed and/or stored at the local processing module 2070 and/or remotely (e.g., at the remote processing module 72, or remote data repository 74). In some embodiments, additional data, such as date and time, GPS location, or other global data may be received directly at the local processing module 2070. Data regarding content being delivered to the user by the system, such as images, other visual content, or auditory content, may be received at the local processing module 2070 as well. In some embodiments, individual data points may be analyzed.

As disclosed herein, a display system 2010 incorporating user and/or environmental sensors may advantageously allow the collection of a variety of data over durations and/or with the ability to cross-reference the data in ways that may provide health benefits to the user, including improving the detection of health conditions (e.g., physical, behavioral, or neurological) and the accuracy of any health evaluations, and/or to modify or adjust therapies. Additionally, data collection over an extended period of time may allow the use of sensors, imaging, and/or other data collection technologies with lower resolution or acuity so as to reduce cost, size, and/or weight of a device, with the collected data being analyzed to filter errors, artifacts, noise, or other results of lower resolution or acuity. In some embodiments, data may be collected and analyzed over long periods of time, such as hours, days, weeks, months, or years, with the display system 2010 being worn by the user for durations of, per day, 3 hours or more, 4 hours or more, 5 hours or more, 6 hours or more, or all day, without removing the device for more than 25%, more than 20%, more than 15%, more than 10%, or more than 5% of the duration. The data collection may be substantially continuous, e.g., occurring at regular intervals, over the entire period of time. Over the duration of the data collection, users of the display system may wear the system substantially continuously for durations of over 3 hours or more, 4 hours or more, 5 hours or more, 6 hours or more, or a full day or more, at a time. Over these durations, the user preferably is able to comfortably wear the system without taking the device off for more than 25%, more than 20%, more than 15%, more than 10%, or more than 5% of the relevant duration.

In some embodiments, a series of data points is collected from one or more sensors of the display system 2010 over the course of one of the above-noted durations. For example, one or more of the user sensors 24, 28, 2030, 32 and/or environmental sensors 34 may be configured to substantially continuously collect data while the user is wearing the display system containing the sensors. The system may additionally be substantially continuously collecting data regarding visual and/or auditory content being delivered to the user by the display system. Preferably, the data collection is performed for durations of 3 hours or more, 4 hours or more, 5 hours or more, 6 hours or more, or a full day or more, at a time, without the user taking the device off for more than 25%, more than 20%, more than 15%, more than 10%, or more than 5% of the relevant duration.

In some embodiments, data from two or more sensors and/or data input sources may be correlated to improve the monitoring, diagnostic, therapeutic, and/or health analysis capabilities of the display system 2010. In some more embodiments, data from user sensors 24, 28, 2030, 32 may be correlated with data from environmental sensors 34, allowing the display system 2010 to monitor the effects of interactions between the user and the real and/or augmented environment. This correlation may be analyzed for a behavioral analysis, diagnostic or monitoring purposes, and/or a health analysis. For example, sensor data such as heart rate, blood pressure, or other user-specific data may be correlated with data from environmental sensors. Such environmental data may include time and/or date, so as to track cycles or trends in such physiological parameters over the course of a day, multiple days, or longer time periods. As another example, outward-facing and/or inward-facing cameras may be capable of identifying objects such as food items and detecting when such items are consumed. The display system 2010 may concurrently monitor food items eaten by the wearer as well as a physiological data source for user-specific data such as a blood pressure sensor or a blood sugar monitor. The system may analyze the blood pressure or blood sugar data for a period of time after an item of food is consumed in order to observe a correlation between diet and fluctuations in one or more of the physiological parameters. The correlation and analysis may trigger a response from the system, for example, to alert the user, alert another user, run a diagnostic test, or take other responsive action.

In some embodiments, combined data points as described above may be observed repeatedly over the course of minutes, hours, days, months, or longer time periods, allowing for a large number of data points to be analyzed, thus increasing the ability of the display system 2010 to identify which user-specific data are actually correlated and/or causally linked with observed environmental factors, and which observed user-specific data are merely coincidental and/or unrelated to observed environmental factors. Data collection over time may also allow for historical analysis, such as to identify changes by comparison to previous data or to identify behavioral trends.

Some embodiments of the display system 2010 may further allow for the sharing of data between multiple users and devices. Similar to monitoring a single user over an extended time period as described above, sharing of data between multiple users may provide a significantly larger data set and allow for more accurate determinations of diagnoses and/or causal relationships. Several example situations of enhanced data analysis through data sharing will now be described.

In some embodiments, user-specific data may be shared among users located in the same physical vicinity, such as with a single room, a building, a vehicle, or a defined outdoor space, area code, city, state, etc. Each of the users may be wearing a display system 2010, which may detect the common location of the users based on a location sensor (e.g., GPS) and/or simply by detecting the presence of an available communication channel with other users. The display system 2010 may then collect physiological user data (including behavioral data) and/or access data earlier-collected for that location. The data may then be shared and the display system 2010 may be configured to make comparisons of the collected user data. For example, the shared data may indicate that multiple users in a local area have a disease, started showing symptoms of a disease at the same time, and/or were present at a particular location for a similar duration before showing symptoms. Similar patterns in the user data over the population of user may then allow for the determination that a causal factor is present in the local environment, such as a contagion, pollen, or other condition causing, e.g., pink eye. Moreover, sharing of data may allow for all users in a local area to be made aware of an environmental factor only detectable by a subset of users and/or systems in the local area. This sharing of environmental data advantageously provides a more complete description of the environment than may be possible if only environmental data collected by the user were available. This more complete description may thereby facilitate more accurate analyses. For example, a dog may walk into a room behind a user and may be undetectable by the user's system if the dog is out of sight of any cameras of the user's system. However, another user in the room may be facing the dog, allowing the second user's system to detect the dog and alert the first user's system of the presence of the dog. Such information may form a more complete environmental database from which to draw correlations. For example, knowledge of the dog's presence may facilitate the correlation of an environmental variable (the dog's presence) and the onset of allergies by dog-allergy sufferers. In another example, an abnormality in a single user may be determined based on shared data from other users. For example, a thermal camera may be used to determine if a nearby user has a fever. If the system determines that a sick user interacted with another user who had a fever, the system may determine the source of the illness. In yet another example, shared data may be used to analyze historic interactions between users. For example, information regarding when and how often certain users have interacted or been in similar vicinities may be used, for example, to remind a user how they know another user, to determine if a user has a stalker, or any other analysis of historical interaction data.

In some embodiments, the collected user data may be shared with others for purposes of notification, particularly in situations in which the user data is out of the norm for that user. For example, authorities such as police and/or emergency medical responders may be alerted (e.g., to come to a location and/or view camera feeds of that location) if multiple device users in the same public space begin recording abnormal EEG or blood pressure readings, record a loud sound at a microphone, view a high-intensity flash at an outward-facing camera, or all get quickly dilated pupils at the same or similar time. Such reactions amongst a population may indicate an emergency situation that requires an emergency response. In yet another example, it may be detected that multiple device-wearing drivers in a local driving area begin exhibiting abnormal readings, such as high blood pressure or increased EEG activity. It may then be determined that a traffic jam is present, and other users approaching the area may be alerted. It will be appreciated that sharing data among multiple users and detecting similar user-specific data among the users may confirm that similar environmental stimuli are present (e.g., an emergency situation or a traffic jam). It will also be appreciated that access to similar types of data among different users, at slightly different locations within a given area, may help to pinpoint the specific location of a stimulus. For example, the location of a loud noise, such as gunfire, may be determined by comparing the relative level of noise detected by microphones 34 on the display devices worn by the users. In another example, the location of such an event may be determined based on lines of bearing (LOB) calculation. For example, if a number of dispersed users each turn their heads to look at the source of a sound or visual stimulus, their geoposition, azimuth, and elevation may be calculated, from which lines of bearing may be used to triangulate a location. In addition, user sensors of the system may be used to determine if the user nearest the environmental stimulus is still experiencing shock or other resulting effects, running away from the incident, and/or experiencing other feelings related to the incident.

Data may also be shared among users who have visited a defined location, such as a restaurant or the venue of a public event, even if those users were not all present at the same time. For example, if a number of users become ill and exhibit similar physiological symptoms after visiting a restaurant at different times, their similar user-specific data indicating symptoms of the illness may be combined to determine that the restaurant may have been the cause of the illness. Such determinations may be much more difficult or impossible to achieve without the correlation of data between multiple users, as a single detection of low blood oxygen or other physiological symptom might be attributed to a factor other than an environmental factor. In another example, data sharing between a plurality of users may facilitate a medical response to a user having health issues. A local individual user may be having a health problem and may therefore be unable to communicate the nature of the user's sudden health issue and/or other conditions material to medical treatment. Another user nearby may be notified of the situation and directed to proceed to the location of the first user. Shared data may be provided to the second user through the second user's display system, which the second user may then provide to first responders present at the scene (e.g., allergies to medication, need for an epinephrine injection, blood glucose, blood pressure, etc.). In the absence of first responders, a secondary user's display system may direct the secondary user regarding actions to render assistance. For example, the secondary user may be instructed to call 911 and/or may be instructed by the display system on how to perform CPR.

In some embodiments, the systems 600, 2010 (FIGS. 12, 10) may be configured to determine a health status of a person other than the primary user and/or wearer of the systems 600, 2010. In various embodiments, the person other than the primary user may or may not be a user of a similar system 600, 2010. If the other person is also a user of a similar system 600, 2010, data collected from systems 600, 2010 worn by the other user may be correlated with data collected by the primary user's system 600, 2010 to improve tracking and/or analysis of the other user's health status since, e.g., these other systems may advantageously provide different views of the user. The display systems may further be configured to determine a health status of another person based on observation and/or knowledge of human anatomy, physiology, time-location correlation, or personal shared information. Diagnostic and therapeutic functions may be administered a user's display system using an/or based on augmented reality and/or virtual reality content, guided imagery and/or audio, eye tracking, time, facial recognition sensors and algorithms, body language detection, and/or one or more microphones.

Some embodiments may include a display system 2010 configured to be worn by a secondary user, such as a clinician, to enhance an evaluation of a patient. In one example, the clinician may observe a patient walking to evaluate the patient's gait. A display system 2010 worn by the clinician may augment the clinician's view of the patient with additional content based on data obtained from monitoring the patient. For example, the content may be 3D content in multiple depth planes depicting aspects of the patient's gait such as leg separation, toe-in/toe-out gait, swaying, or other gait variables. In some aspects, the display system may be configured to show gait variables that may include head motion, such as up-and-down or sinusoidal movements and/or bobbing of the head, as measured, for example, by head pose sensors, accelerometers, inertial measurement units, or the like. In some embodiments, these variables may be presented graphically as additional augmented reality virtual content along with views of the patient's gait. Advantageously, the ability of the display system to display information on multiple depth planes allows for more information to be provided to the clinician than would be available from a simple side view of the user (including the user's gait). In some embodiments, the display system 2010 worn by the clinician provides the only views of the patient. Similarly, in another example, more information about the user's head pose may be provided by the display system 2010 worn by the clinician to the ability to display that information across multiple depth planes. In some embodiments, the detection of the patient's head pose may be used to indicate to the clinician if an instruction was understood by a patient. In yet another example, a display system 2010 may indicate to the clinician an evaluation of a stroke patient's recovery of movement. This evaluation may include conducting vector calculations to determine the amount of movement that the patient is able to perform. For example, a display system 2010 worn by the clinician may obtain data from one or more cameras or other sensors of the clinician's display system 2010, from one or more sensors of another display system 2010 worn by the patient, or a combination of data from multiple sources to determine the range of movement of the patient. In addition, any content displayed to a clinician's display system 2010 may additionally or alternatively be displayed to a display system 2010 worn by the patient.

In some embodiments, the display system 2010 may be configured to provide feedback and/or intervention modification to a user. As used herein, biofeedback may include modification of any type of content and/or stimulus delivered to a user of a display system 2010 based on data from user sensors (e.g., cameras 24 and 28, internal sensors 2030, motion sensors 32) and/or environmental sensors 34. Biofeedback may be triggered by particular raw data received at any camera or sensor, or by the results of further analysis of such data (e.g., an abnormal trend in a physiological parameter, an object detected based on images from an outward-facing camera, a medical diagnosis based on user-specific data, erratic, accelerated, repetitious or otherwise unusual actions, or a behavior determined by user sensors that may be correlated to an environmental factor). Biofeedback may be provided in real time or near-real time, or may be provided later based on previously recorded and analyzed data. Some biofeedback may be delivered so as to make the user aware of the biofeedback (e.g., instructions provided visually or by sound communication, images that show the user's physiological data, e.g., heart rate or blood pressure) or may be delivered without the awareness of the user (e.g., adjusting a brightness of an image or altering a treatment plan). Several examples of biofeedback will now be described.

In one example of biofeedback, a user may wear a display system 2010 for purposes of physical therapy. The display system 2010 may guide the user through a physical therapy routine weekly, daily, or multiple times per day, or at another suitable frequency. In some embodiments, instructions for the physical therapy routine may be provided through displayed instructions in an augmented reality system, or through audible instructions. For example, the display system 2010 may be an augmented reality system configured to indicate physical therapy objects and instruct the user to complete actions such as picking up or moving objects, or other physical therapy-related tasks. The success or inability of the user to complete the instructed tasks, as well as any associated physiological signs, may be detected by user sensors and/or cameras as described herein, and analyzed to track the user's physical therapy progress. In response to detected improvements in strength or other health criteria, the display system 2010 may provide biofeedback by increasing or decreasing the intensity, length, difficulty, or otherwise altering the physical therapy routine to meet the changing needs of the user. For example, if the user's physiological measurements (e.g., heart rate and/or blood pressure) are below desired levels, the display system 2010 may be configured to increase the intensity of the physical therapy routine. Conversely, if the user's heart exceeds predetermined thresholds, the display 2010 may be configured to decrease the intensity of the physical therapy routine. In some embodiments, the display system 2010 may detect the inability of a user to complete a physical therapy task (e.g., by using a downward-facing camera 28 to determine that the user is not able to assume a particular pose or move with a particular gate) and substitute a different (e.g., easier) task until the user's health improves. Data regarding the user's progress may be stored and tracked in conjunction with a treatment or therapy plan.

In another example of biofeedback, the display system 2010 may be configured to detect a recurring sign or symptom of a chronic illness and to provide a responsive treatment or instruction to manage the sign or symptom. For example, a user may have been diagnosed with Parkinson's disease, which may cause an intermittent involuntary tremor. The user's display system 2010 may be configured to detect when the user is experiencing a tremor, such as by analysis of images obtained from the downward-facing camera 28. When a tremor is detected, the display system 2010 may be configured to triangulate that input with other sensory data such as EEG or erratic eye pursuits, and may further be configured to provide a flash of light, electrical stimulation via transcranial direct current stimulation (tDCS), magnetic stimulation via transcranial magnetic stimulation (TMS), or other stimulus to attempt to at least temporarily halt or reduce the detected tremor.

Similarly, a user may be prone to seizures due to epilepsy or any of various other conditions. In some embodiments, the display system 2010 may perform diagnostic functions such as flashing a bright light or checkerboard pattern to the user, manipulating content and/or motion through depth planes, or manipulating 3D sound, to stimulate a seizure and determine triggering stimuli. The display system 2010 may then recognize the occurrence of triggering stimuli in the future, and may provide therapeutic content to prevent, mitigate, or avoid seizures (e.g., white noise, white light, or other content that may prevent seizures). It will be appreciated that this content may be provided on one or more depth planes while providing proper accommodation and vergence matching to allow long-term user viewing comfort.

In some embodiments, the content may facilitate meditation and/or guided imagery and/or sound therapy and may be utilized to calm the user generally, and not necessarily to prevent seizures. For example, the display system 2010 may determine that loud noises or bright light trigger an undesirable reaction in a patient with post-traumatic stress disorder (PTSD). This reaction may include eye dilation, sweating, screaming, or other PTSD signs or symptoms. The display system 2010 may provide desensitizing therapy in response to the determined triggering stimuli, and may monitor the patient's symptoms and response to triggering stimuli over an extended time period, to determine the patient's progress over the course of the therapy.

Figure 11:
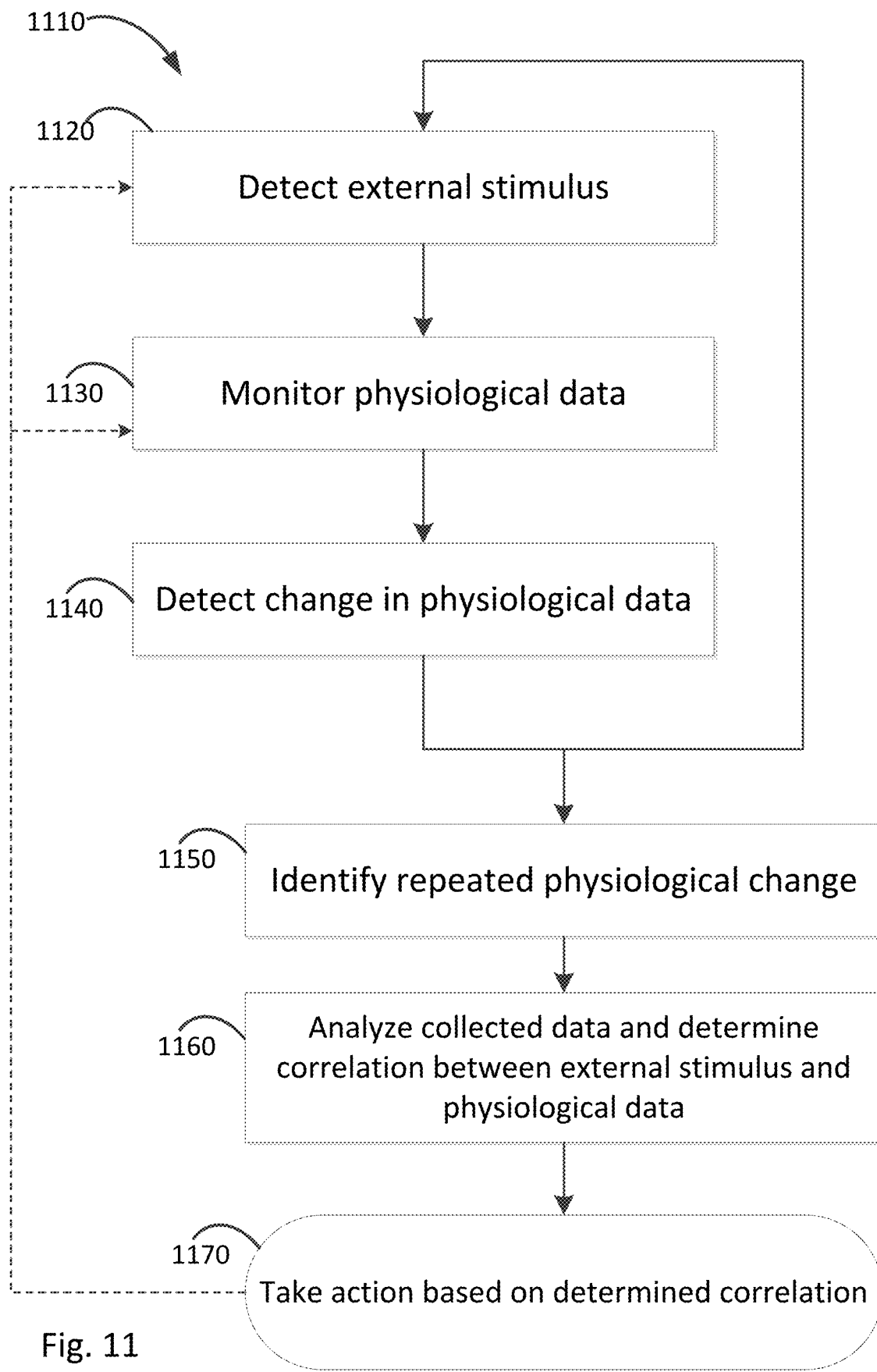
FIG. 11 is a flowchart illustrating an example method of correlating data from multiple sources to analyze a user.

Referring now to FIG. 11, an example method of correlating user data with external environmental data for health analysis will now be described. The method 1110 illustrated in FIG. 11 may be performed using any of the wearable display systems described elsewhere herein. For example, the display system 2010 depicted in FIG. 10 may be configured to perform the method 1110.

The method 1110 may begin at block 1120, where an external stimulus (which is external to the user), such as an event, time, or object (either virtual or real) is detected. In some embodiments, the environment (e.g., location, temperature, speed, etc.) may be monitored before block 1120 so as to be ready to anticipate an external stimulus for faster and/or more accurate processing of the external stimulus for contextual learning. An external stimulus may be detected by any of the environmental sensors or data inputs described above with reference to FIG. 10. For example, image analysis of an image obtained from an outward-facing camera may detect that the user is eating a meal high in sodium and/or saturated fat, such as a cheeseburger. As described herein, the analysis of data received at environmental sensors may occur at a local processing module, or remotely. When an external stimulus has been detected and identified, the method 1110 may continue to block 1130.

At block 130, user-specific data is monitored following the detected external stimulus. In some embodiments, the user may be monitored before block 130 so as to be ready to anticipate user-specific data and/or changes for faster and/or more accurate processing of the user-specific data for contextual learning. In some embodiments, the method may begin at block 1130. That is, collected user-specific data may trigger the initiation of the method 1110 without the need for an external stimulus. User-specific data may be obtained from any of the various inward-facing cameras or other user sensors described above with reference to FIG. 10. In the example process in which a user is determined to have consumed an unhealthy meal, the system may monitor physiological parameters of the user such as heart rate, blood pressure, skin pallor, or other parameters. In some embodiments, the system may track such parameters for minutes, hours, or even days following a detected external stimulus. For example, the system might track a user's blood pressure continuously for several hours following a meal so as to increase the probability of detecting a change in a physiological parameter related to the meal. The method 1110 may then continue to block 1140.

At block 1140, the system may detect a change in one or more physiological parameters being monitored. For example, in the unhealthy meal scenario described above, the system may detect an increase in blood pressure in the minutes or hours following the user's consumption of the unhealthy meal. The system may also detect additional physiological changes, such as an increase in heart rate. If a change in a physiological parameter is detected, the system may record the change in association with the observed external stimulus. For example, the system may record an increase in blood pressure associated with consuming a cheeseburger.

It will be appreciated that a single data point, or even a few data points, regarding the associations described herein may not be sufficient to establish a correlation between a type of external stimulus and a detected physiological change. However, the system may continue correlating similar external stimuli with observed user-specific data collected over an extended time period, such as days, weeks, months, or even years. In some embodiments, the system may be configured to store each data point and recall previous data points to identify patterns, trends, or the like. In addition, the process may be predictive. For example, the system may identify possible trends as hypotheses based on data suggesting a trend, e.g., even before enough data is collected to achieve statistical significance. The system may then use future data points to confirm or refute the hypotheses. Severe abnormalities in the data may cause direct alerts, for example, in the case of a heart attack or stroke. Thus, the display system 2010 may be configured to progress through method 1110 whenever a similar external stimulus is detected. For example, the method 1110 may repeat blocks 1120, 1130, and 1140 as described above each time the system 2010 detects that the user is consuming a meal. Over an extended time period, the user may eat a sufficient number of healthy and/or unhealthy meals (e.g., meals high in sodium and/or saturated fat) to provide a useful data set for statistical analysis. Once sufficient data points have been recorded, the method 1110 may continue to block 1150.

At block 1150, the method 1110 may identify a repeated change in one or more physiological parameters associated with similar or identical external stimuli. For example, a user may eat multiple unhealthy meals over the course of weeks or months. After completing the analysis described above, it may be observed that the user exhibits elevated blood pressure following the consumption of most or all such unhealthy meals. In some embodiments, the method may record each recurrence of unhealthy meal consumption along with an indication of whether the user's blood pressure rises following the meal. Data may be triangulated with other sensory data, such as blood glucose, ECG, heart rate, or other data. Such data may be recorded in a database locally or remotely (e.g., in the local data processing module 2070, the remote processing module 72 and/or remote data repository 74) for later analysis. When a sufficiently large data set has been recorded to permit reliable statistical analysis, the method 1110 may then continue to block 1160.

At block 1160, the correlated data set is analyzed to determine a correlation between the observed external stimulus and the observed physiological change. It will be appreciated that any of various known inferential statistical analysis methods may be applied to determine if the external stimulus and physiological change are correlated and/or causally related. In some embodiments, a behavioral or emotional response may also be determined from the physiological change and user sensors, and it may then be determined if the behavioral or emotional response was correlated to and/or causally related or unrelated to the external stimuli and environmental factors. In various statistical analyses, outlying data points may be discounted. For example, if the user's blood pressure was observed to increase following every unhealthy meal, or following a majority of unhealthy meals, it may be determined that the unhealthy meals are correlated with the increased blood pressure. In some cases, statistical analysis may indicate that the external stimulus is not the cause of the observed physiological change. In various embodiments, both outcomes may provide useful information for purposes of medical diagnosis, monitoring, and/or treatment of the user. For example, at block 1170, the results of the correlation analysis may be forwarded to a health professional for review and/or further analysis to make a diagnosis regarding a health condition, and/or the development of a therapeutic protocol to address an undesirable health condition. In other examples, the user may be notified, an automated test may be performed, another user may be alerted, and/or other action may be taken based on the determined correlation. In some other embodiments, the display system 2010 may be configured to make a diagnosis or provide a list of position health conditions that are indicated by the particular data found by the display system 2010.

In some embodiments, the method may continue by providing biofeedback to the user. For example, the system may return to block 1120 or block 1130 to provide any of various virtual external stimuli, for example, in accordance with the biofeedback methods described with reference to FIG. 10.

In some embodiments, the order of the blocks 1120, 1130, 1140 may be altered. For example, block 1130 may be conducted before or simultaneously with block 1120. Also, in some embodiments, one or more of blocks 1140 and 1150 may be omitted. For example, the display system 2010 may be configured to determine a correlation between user-specific data and environmental data using a single measurement for each of the user-specific data and environmental data. In some embodiments, block 1120 may be omitted and the method 1110 may begin at block 1120; that is, collected user-specific data may trigger the initiation of the method 1110 without the need for a detected external stimulus.

In some embodiments, the external stimulus may simply be a measurement of environmental data. In some other embodiments, the external stimulus may be image content projected by the display system 2010 to the user. For example, the external stimulus may be imagery projected to cause particular responses in users (e.g., a virtual spider may be projected to arouse fear in a user having arachnophobia). The user sensors may then detect whether an expected involuntary physiological response (e.g., pupil dilation or sweating indicating fear) or a voluntary response, which may also be considered to be behavioral response (e.g., screaming or shrieking indicating fear) occurs and/or determine the extent of the deviation from the expected response.

With continued reference to FIG. 11, as described herein, the display system 2010 allows individual manipulation of a user's accommodation and vergence, which may be used to cause physiological/neurological changes in the user. As discussed herein, at block 1120, the display system 2010 may be configured to display images to the user that have proper, physiologically correct accommodation/vergence matching. In some other embodiments, the display system 2010 may be configured to provide mismatched accommodation and vergence matching at block 1120. For example, the display system 2010 may be configured to switch the depth plane for particular image content, thereby displaying the image content on a different depth plane than the depth plane that would provide proper accommodation/vergence matching. Thus, the system may manipulate visual content provided to the user so as to establish more or less accommodation/vergence mismatch. In some embodiments, the accommodation-vergence mismatch may be about 0.25 diopter or more, about 0.33 diopter or more, or about 0.5 diopter or more. Whether a proper or improper accommodation/vergence matching is provided by the display system, at block 1130, the display system 2010 may be configured to collect various types of user data, including neurological responses such as electrical activity (e.g., as measured by EEG), and/or a physiological response such as a blood pressure, breath rate, pupil dilation/contraction, etc. As a result, changes in various neurological and/or physiological parameters of the user may be observed at block 1140 due to the presentation of augmented reality content having improper accommodation and vergence matching.

The display system 2010 may achieve proper (matched) or improper(mismatched) accommodation/vergence matching using any of various methods. Accommodation/vergence matching may be dependent, for example, on the wavefront divergence of light for forming images displayed to each eye, and the location of a virtual object in the images displayed to each of a wearer's eyes. In some embodiments, the display system 2010 may select a combination of wavefront divergence and image location based on one or more databases, lookup tables, or the like. For example, a local or remote database may include information indicating, for each of various depth planes, particular defined amounts of wavefront divergence and one or more image display locations corresponding to a proper accommodation/vergence match and/or one or more image display locations corresponding to any number of less proper accommodation/vergence matches. In some embodiments, the display system 2010 may be configured to apply one or more predetermined mathematical relationships to determine one or more appropriate locations for virtual content in images provided by the display, for example, to provide more or less proper accommodation/vergence matching. In various embodiments, the display system 2010 may be configured to use a database and/or a mathematical relationship to determine the location of virtual content in images and/or the wavefront divergence of outputted light based on a predetermined desired depth plane for the virtual content.

Similarly, the display system 2010 may allow for individual manipulation of a user's vestibular system. For example, at block 1120, the display system 2010 may be configured to display images to the user that have proper vestibular cues, such as a horizon consistent with the real-world horizon. The display system 2010 may be further configured to provide improper vestibular cues at block 1120, such as a tilted or vertically shifted horizon, or other inconsistent visual content. Whether proper or improper vestibular cues are provided by the display system 2010 at block 1130, the display system 2010 may be configured to collect various types of user data, including neurological responses such as electrical activity and/or a physiological response such as a blood pressure, breath rate, pupil dilation/contraction, etc. As a result, changes in various neurological and/or physiological parameters of the user may be observed at block 1140 due to the presentation of augmented reality content having improper vestibular cues. In various embodiments, manipulation of vestibular cues may be used for diagnostic and/or therapeutic applications related to dizziness, vertigo, or other conditions affecting the vestibulo-ocular system. In some embodiments, manipulation of proprioceptive cues and/or audiovisual cues (e.g., temporally or spatially manipulated audiovisual cues) may similarly be used.

In some embodiments, the display system 2010 may be configured to provide audiostrobe functionality in which augmented reality content is displayed across multiple depth planes while providing proper accommodation and vergence to the user. In some embodiments, the augmented reality content is selected to facilitate the user experiencing a Ganzfeld effect. As discussed herein, the ability to provide proper accommodation and vergence matching allows the long-term wearing of the display system 2010.

Figure 12:
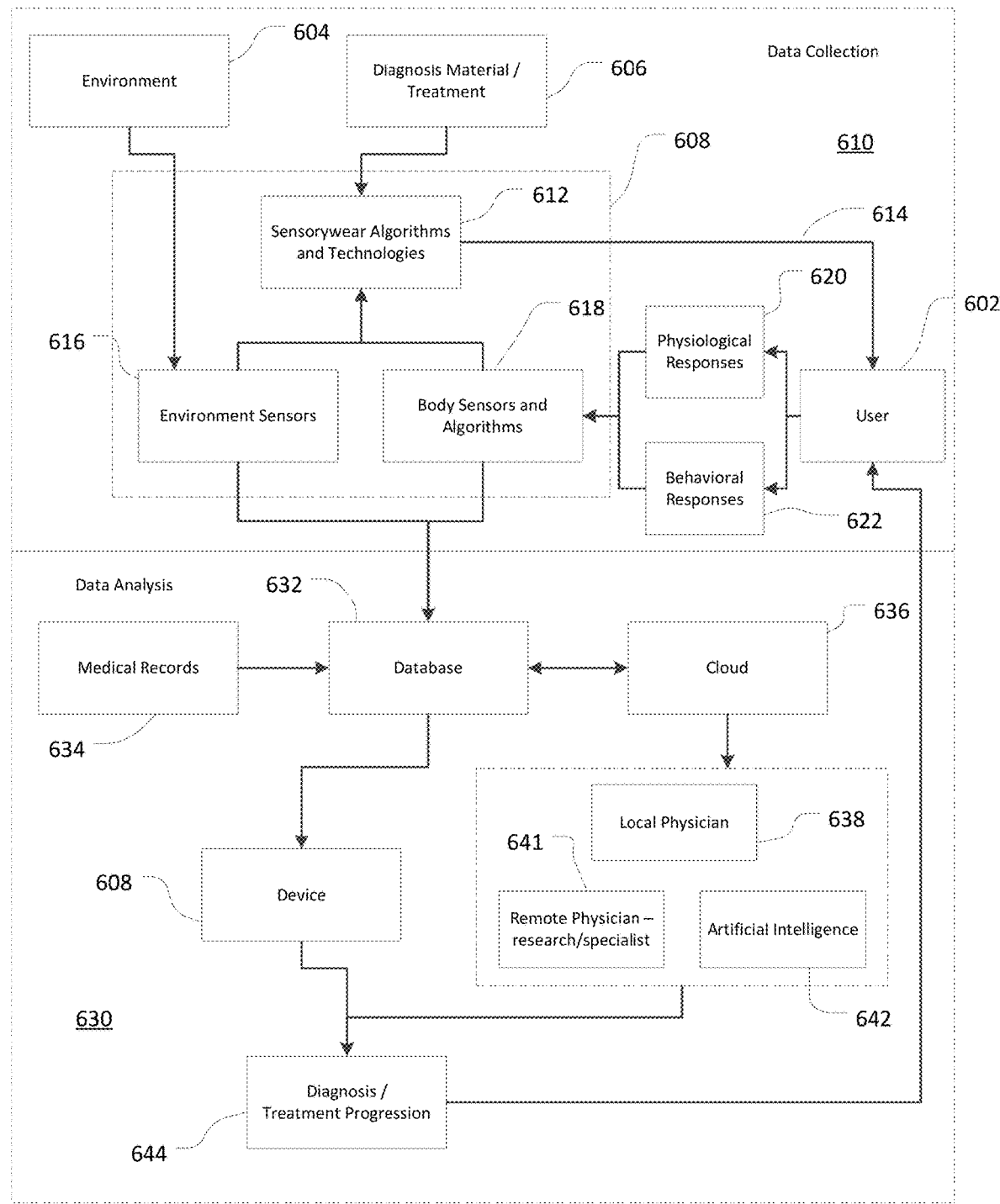
FIG. 12 schematically illustrates a health system configured for diagnosis, monitoring, and/or treatment using display systems disclosed herein.

Reference will now be made to FIG. 12, which schematically illustrates a health system 600 configured for diagnosis and/or treatment using display systems disclosed herein. Preferably, the health system is capable of diagnosis and/or treatment, as well as longitudinal and real-time monitoring. Generally, the telehealth system 600 includes a data collection portion 610 and a data analysis portion 630. The system 600 may be used for building an inclusive user and environmental factor database for historical analysis, for behavioral trends, for health purposes, for diagnostic, therapeutic, and/or treatment purposes, and/or for other purposes.

The system 600 may include an augmented reality (AR) device 608 configured to be worn by the user 602. Preferably, the AR device 608 is the display device 2010 (FIG. 10), and various computer programs, including algorithms, may be stored in one or more of the local processing and data module 140, remote processing module 150, and remote data repository 160 (FIG. 9D). Algorithms and technologies 612 of the AR device 608 may be configured to deliver content 614 to the user 602. Content 614 may be delivered visually, aurally, or otherwise, as described elsewhere herein, for example, as an external stimulus as described with reference to FIG. 11. Algorithms and technologies 612 of the AR device 608 may further receive data from environment sensors 616 and/or body sensors and algorithms 618 of the AR device 608. Environment sensors 616 may detect environmental data from the environment 604 around the user 602, for example, to indicate an external stimulus as described with reference to FIG. 11. The environment sensors 616 and/or body sensors and algorithms 618 may correspond to the environmental sensors 34 and user sensors 24, 28, 2030, 32 (FIG. 10), respectively. Body sensors and algorithms 618 may receive input of physiological responses 620 and/or behavioral responses 622 exhibited by the user 602, such as to monitor user-specific data as described with reference to FIG. 11. It will be appreciated that the physiological responses 620 and behavioral responses 622 may be voluntary or involuntary. Algorithms and technologies 612 may further receive input of diagnostic material and/or treatment 606. For example, diagnostic material and treatment 606 may include information such as predetermined diagnostic tests, predetermined or prescribed medical treatment plans or procedures, or any other instructions or data provided to the algorithms and technologies 612 of the AR device 608 for diagnostic and/or treatment purposes.

In some embodiments, data from the environment sensors 616 and body sensors and algorithms 618 may be analyzed for purposes of diagnosis or treatment, as described with reference to block 160 in FIG. 11. Analysis may occur locally at the AR device 608, or data from the sensors 616 and 618 may be transmitted to a remote device, such as a server or other processing circuitry (e.g., the remote processing module 140, or remote data repository 160 of FIG. 9D), for analysis. Transmission may be accomplished by, e.g., wired or wireless communications systems. The environment sensors 616 and body sensors and algorithms 618 may transmit data to a database 632 where the data may be analyzed and/or stored. The database 632 may access additional data regarding the user 602 from a database of medical records 634. Medical records 634 may be stored, for example, in a computing network of the user's healthcare provider or elsewhere. The medical records 634 and database 632 may be part of the remote data repository 160 (FIG. 9D) in some embodiments.

In various embodiments, data received and/or stored at the database 632 may be analyzed locally at the device 608, or may be analyzed remotely, for example, following transmission to external processing circuitry through the cloud 636 or other data sharing or transmission medium. Transmitted data may be analyzed for diagnosis, treatment, or evaluation, such as by a local physician 638, remote physician 641 (e.g., a research physician or specialist), and/or by may be analyzed automatically, such as through image or material analysis by artificial intelligence 642 or other computerized diagnosis or treatment evaluation module. It will be appreciated that the cloud 636 may also be part of the remote data repository 160 (FIG. 9D).

Following analysis of the data from the database 632, a diagnosis and/or treatment progression decision 644 may be generated and delivered to the user 602. For example, a diagnosis or treatment progression decision 644 may include a determination that the user 602 has an identified disease or other medical condition, a determination that the user 602 does not have a particular disease or other medical condition, a determination that a medical treatment process should be initiated, a determination that a medical treatment process should be modified based on the response of the user 602 to a previous treatment 606, a determination that a medical treatment process should be terminated, or any other conclusion based on the analysis of data in the database 632. In some embodiments, these various determinations may relate to correlating collected data and/or taking actions based on a correlation, as discussed herein regarding blocks 160 and 170 respectively (FIG. 11). In some embodiments, the diagnosis and/or treatment progression decision 644 may be delivered to any one or combination of the user 602 (e.g., via a notification displayed by the display system 2010), and a physician or other healthcare provider of the user 602, so as to enable an appropriate response to the diagnosis and/or treatment progression determination 644 such as implementation of a new or modified treatment.

With reference to FIGS. 6, 9D, 11 and 12, further examples of diagnostic, monitoring, and therapeutic applications of the systems and methods disclosed herein will now be described. As disclosed herein, the display system may include various sensors which may advantageously be applied to detect the user's response to various stimuli. For example, behavior tracking may be implemented in a wearable display system, such as the systems described with relation to FIGS. 6, 9D, 10, and 12. With reference to FIG. 9D, detecting and/or tracking behaviors in an augmented or virtual reality display system 20 may include detecting responses to guided imagery and/or audio presented to the user 90 at a display 70 and/or speakers 100, or responses to real world stimuli as detected by outward facing environmental sensors 34 (FIG. 10). With reference to FIG. 10, the system 2010 may monitor the user through inward facing cameras 24 for eye tracking, such as to detect eye position, movement, gaze, or pupil size. Inward facing cameras 24 may further be configured to monitor other facial indicators such as eyelid position, facial muscle crunching, squinting, or other facial position or movement. Downward-facing cameras 28 may further be used to monitor body movements of the user 60 and possibly facial expressions below the camera. The system 2010 may further monitor audible responses from the user, such as speech, using one or more microphones 67. These and other sensors may be implemented to conduct the various diagnostic, monitoring, and therapeutic applications below. Data obtained from any of the sensors described herein may further be compared or otherwise analyzed over time through historical analyses in which the data is compared with a stored data which was collected at different, earlier times. As described herein, inward, downward, and/or outward-facing cameras may be adjustable by a user 60 and/or by the system 2010.

Neurological Analyses

Neurological analyses may include analysis of the peripheral nervous system and cranial nerves. Generally, neurological analyses may be used to analyze behavioral and/or neurological responses of a user. The somatic nervous system controls voluntary body movements, and analyses related to the somatic nervous system may facilitate the determination of behavioral responses. The autonomic nervous system controls involuntary responses, and analyses related to the autonomic nervous system may facilitate the determination of behavioral responses Cranial Nerves (CN) are part of the peripheral nervous system (PNS) and emerge directly from the brain. There are twelve different CNs each serving a different function but all relaying information between the body, mainly regions of the neck and head, and the brain. Defects or injuries to one or more cranial nerves may be detected as abnormal responses to various stimuli, as described below.

In some embodiments, collected user data may be utilized to evaluate the function of the cranial nerves and to detect conditions associated with one or more of the cranial nerves of a user. In one example, the health system 600 (FIG. 12) or the display system 2010 (FIG. 10) may be configured to evaluate the function of the trigeminal nerve, or the fifth cranial nerve (CN V). Transmission of impulses along the fifth cranial nerve may typically be involved in facial functionality such as mastication (chewing) and sensation in facial skin, as well as other motor and sensory functions related to the face. Detection of mastication or other facial motor functions may be accomplished by microphones, one or more downward facing cameras that, e.g., image the user's mouth and/or jaws, and/or other sensors, e.g., inertial measurement units, accelerometers, or the like.

Diagnostic testing of the trigeminal nerve may include evaluation of a blink response, eyelid stimulation, eyelid assessment, and physical stimulation of the eye. For example, a corneal reflex test may be performed by having the cornea of each eye gently touched to induce a physiological response 620 (FIG. 12) such as a blink. Any asymmetry between the corneal reflexes of the two eyes of a user 602 may then be observed using inward facing cameras 24 of the display system 2010 (FIG. 10), and may indicate a lesion in the brainstem between the trigeminal nerve and the facial nerve (the seventh cranial nerve, or CN VII). Monitoring of trigeminal nerve functions may include detecting a blink rate over time, such as to determine eye dryness.

Based on diagnostic testing and/or monitoring of physiological responses 620 associated with the trigeminal nerve over a short or extended time period, the system 600 may determine that the user has one or more neurological conditions associated with the detected response. The determination may be carried out locally or remotely, and in some aspects may include referring to, querying, or otherwise interacting with a database or other repository of medical information. For example, as noted above, the system 600 (FIG. 12) or the system 2010 (FIG. 10) may be configured to interpret asymmetries between the corneal reflexes of the eyes of the user as being indicative of a lesion in the brainstem between CN V and CN VII. As another example, the system 600 (FIG. 12) or the system 2010 (FIG. 10) may be configured to determine that extinction in the presence of intact primary sensation may indicate a lesion in the right parietal lobe. In some embodiments, extinction may be determined to be present based upon the systems 600, 2010 (FIGS. 12,10) observing user responses to a stimulus in isolation, coupled with a lack of response to the same stimulus in combination with another stimulus. In another example, staring spells indicated by a low blink rate over a period of time may indicate nervous system disorders such as epilepsy, and/or memory disorders such as Lewy body dementia or progressive supranuclear palsy. Observations that the user stares at stimuli such as spinning objects or lights may indicate developmental disorders such as autism spectrum disorders. Repetitive eye blinking may indicate nervous system disorders such as epilepsy, and/or motor disorders such as dystonia or Tourette syndrome. Repeated eyelid twitching may indicate behavioral disorders such as stress-related conditions. Blepharospasm, or involuntary eyelid closure, may indicate motor disorders such as dystonia. Detected difficulties in chewing may indicate motor disorders such as amyotrophic lateral sclerosis and/or memory disorders such as frontotemporal dementia. For any of the above analyses, it will be appreciated that data regarding the eyes and eyelids may be obtained using the inward facing cameras 24 of the display system 2010 (FIG. 10), and data regarding the ambient environment may be obtained using outward facing environmental sensors 34 (FIG. 10).

In another example, the systems 600, 2010 (FIGS. 12, 10) may be configured to evaluate the function of the glossopharyngeal nerve, or the ninth cranial nerve (CN IX). Transmission of impulses along the glossopharyngeal nerve are typically involved in sensory and motor functions such as oral sensation, taste, and saliva production. Diagnostic testing of the glossopharyngeal nerve may involve evaluations including swallowing function, displaying augmented reality and/or virtual reality content, providing guided audio and/or imagery, head pose detection, imaging of the eye, and/or physical stimulation of the eye. For example, the system may detect the simultaneous occurrence of swallowing and dilated pupils as an indication of pain associated with swallowing. Assistive therapeutic functionality related to pain associated with swallowing may include helping the user augment food portion and/or bite sizes so as to ease swallowing (e.g., the display system may be configured to make food and/or by sizes appear larger than in reality, so that the user takes smaller portions and/or by sizes). Speech may further be monitored, such as to detect when speech is inaudible. If a user is not able to speak audibly, the systems 600, 2010 (FIGS. 12, 10) may provide assistive therapeutic functionality such as by allowing the user to select words with interactive content, such as an eye gaze-activated keyboard, and audibly outputting the selected words. In some embodiments, the system may function as an augmentative and assistive communication (AAC) device, to supplement or replace speech or writing for those with speech or writing impairments. For example, the system may be configured to supplement or replace speech for users having ALS and/or paralysis. Advantageously, the system includes multiple interaction elements that allow the user to provide inputs in multiple ways, thereby allowing the system to function to supplement or replace speech even as the user's symptoms change or a disease progresses. For example, for users with ALS, as the ALS progresses and muscle movements deteriorate, different interactions with the display system may be utilized to provide inputs that allow the system to transform thoughts into actions and words. As the user's mobility decreases, the user may transition from using gestures to provide inputs to the system (e.g., selecting virtual menu items, typing on a virtual keyboard, etc.), to using their voice, to using totems, to using head pose, to using eye movements to provide inputs to the system. It will be appreciated that the inputs may be utilized for various purposes, including, e.g., choosing letters on a keyboard, directing movement of a wheelchair, etc.

The systems 600, 2010 (FIGS. 12, 10) may further provide speech therapy to a user, with augmented mouth movements overlaid the user's reflection in a mirror. In some aspects, taste may be evaluated by providing a stimulus such as sweetness on the posterior third of the tongue. Tactile sensation in the pharynx may be evaluated based on physical stimulation and/or inquiry about aspiration-related problems.

Based on diagnostic testing and/or monitoring of physiological responses 620 associated with the glossopharyngeal nerve over a short or extended time period, the systems 600, 2010 (FIGS. 12, 10) may determine one or more neurological conditions associated with the detected response. For example, the systems 600, 2010 (FIGS. 12, 10) may be configured to determine that detected dysphagia, or difficulty in swallowing, correlated with a normal gag reflex, may indicate a lesion in the motor portion of the glossopharyngeal nerve. In another example, detected dysphagia correlated with dysarthria, or difficulty in speaking, may be determined to indicate an injury to the nuclei of the glossopharyngeal and/or vagus nerves. Detected signs of dysphagia may be determined to be caused by nervous system disorders such as acute disseminated encephalomyelitis, epilepsy, and/or or Guillain-Barré syndrome; motor disorders such as cerebral palsy, Huntington's disease, motor neuron disease, amyotrophic lateral sclerosis, progressive bulbar palsy, pseudobulbar palsy, type I spinal muscular atrophy, and/or or Kennedy's disease; memory disorders such as frontotemporal dementia and/or or progressive supranuclear palsy; and/or injuries such as stroke. Detected signs of dysarthria may be determined to indicate nervous system disorders such as multiple sclerosis and/or or Schilder's disease; and/or motor disorders such as ataxia, cerebral palsy, Huntington's disease, motor neuron disease, amyotrophic lateral sclerosis, primary lateral sclerosis, progressive bulbar palsy, pseudobulbar palsy, and/or or Kennedy's disease.

In yet another example, the systems 600, 2010 (FIGS. 12, 10) may be configured to evaluate the function of the vagus nerve, or the tenth cranial nerve (CN X). Transmission of impulses along the vagus nerve is typically involved in functions such as parasympathetic control of the heart and digestive tract. In addition, the vagus nerve largely controls the heart, lungs, and digestive tract, and may also control physical and emotional effects. Diagnostic testing of the vagus nerve may involve displaying augmented reality and/ or virtual reality content, providing guided audio and/or imagery, detecting eye position and/or movement tracking, and/or utilizing clinician-worn display devices. For example, the system may monitor speech, such as to detect when speech is inaudible. If a user is not able to speak audibly, the systems 600, 2010 (FIGS. 12, 10) may provide assistive therapeutic functionality such as by allowing the user to select words with interactive content, such as an eye gaze-activated keyboard, and audibly outputting the selected words. As noted above, the system may be configured to function as an augmentative and assistive communication (AAC) device, to supplement or replace speech or writing for those with speech or writing impairments. In another diagnostic example, the system may use palate evaluation to detect the symmetry of a patient's palate elevation and/or gag reflex. Articulation may be monitored as well, such as by asking the user to repeat words or other sounds to detect dysarthria or other abnormal speech condition.

Based on diagnostic testing and/or monitoring of physiological responses 620 associated with the vagus nerve over a short or extended time period, the systems 600, 2010 (FIGS. 12, 10) may determine one or more neurological conditions associated with the detected response. For example, the systems 600, 2010 (FIGS. 12, 10) may be configured to determine that a hoarse voice, dysphagia, choking associated with drinking, and/or an absent gag reflex may indicate a lesion of the laryngeal portion of the vagus nerve. In another example, palatal and/or laryngeal paralysis, abnormal esophageal motility, gastric acid secretion, gallbladder emptying, abnormal heart rate, and/or other autonomic dysfunction may indicate the presence of other vagus nerve lesions. Detected signs of weak palatal movement and/or reduced gag reflexes may be determined to indicate motor disorders such as progressive bulbar palsy. Detected signs of increased gag reflexes may indicate be determined to motor disorders such as pseudobulbar palsy. Signs of locked-in syndrome may indicate injury to the nucleus of the vagus nerve and nerve tract. Detected signs of an impaired voice may be determined to indicate motor disorders such as spasmodic dysphonia, laryngeal dystonia, motor neuron disease, and/or pseudobulbar palsy. Vocal tics may be determined to indicate motor disorders such as Tourette syndrome. Detected shortness of breath may be determined to indicate motor disorders such as motor neuron disease, amyotrophic lateral sclerosis, type I or II spinal muscular atrophy, and/or congenital spinal muscular atrophy with arthrogryposis; and/or behavioral disorders such as anorexia or other eating disorders. Detected signs of slurred speech may indicate motor disorders such as oromandibular dystonia, amyotrophic lateral sclerosis, and/or primary lateral sclerosis; memory disorders such as progressive supranuclear palsy; behavioral disorders such as intoxication (e.g., addiction or alcoholism); and/or injuries such as stroke, brain aneurysm, and/or traumatic brain injury. Detected signs of muffled speech may be determined to indicate motor disorders such as Parkinson's disease. Detected signs of automatic nervous system malfunction (e.g., blood pressure drop when standing, dizziness, falls, urinary incontinence, pulse, sweating, bowel control issues) may be determined to indicate memory disorders such as Lewy body dementia.

Mental Status and Disorders

User data collected by the systems 600, 2010 (FIGS. 12, 10) may be used to perform mental status testing. In some aspects, mental status testing may allow the systems 600, 2010 (FIGS. 12, 10) to differentiate between the cognitive function and the behavioral function of a user. In some embodiments, the systems 600, 2010 (FIGS. 12, 10) may be configured to detect delusions and/or hallucinations. Diagnostic testing to detect delusions and/or hallucinations may include various functions described herein, such as displaying augmented reality and/or virtual reality content, providing guided audio and/or imagery, and detection of user responses, such as spoken or otherwise audible responses detected at a microphone, and/or responses detected based on eye tracking. For example, the systems 600, 2010 (FIGS. 12, 10) AR device 608 may be configured to detect the presence of delusional thought processes, auditory hallucinations, or visual hallucinations based on presenting psychiatric diagnostic questions to a user, detecting the user's response to the questions, and comparing those responses with data about the ambient environment detected by environmental sensors 34 (FIG. 10). In some embodiments, the device 608 may be configured to implement passive monitoring, as disclosed herein, by detecting the user's response to stimuli without presenting diagnostic stimuli such as questions or the like. The device 608 may monitor the environment to wait for the user to encounter a stimulus of interest, and detect the response of the user each time such stimulus is detected. For example, rather than presenting a question or instruction to the user through augmented reality or audio content, the device 608 may detect a condition in the world (e.g., an object, noise, sign, social interaction, etc.) that would be expected to produce a response similar to the question or instruction. The device 608 may be configured to detect the presence of patterns in the correlation of data from the observed environment with data obtained from the user's body. Such correlation of data to identify trends may be achieved by various methods, such as the method 110 described with reference to blocks 120-160 of FIG. 11.

Based on detected behavior responses 622 (FIG. 12), the systems 600, 2010 (FIGS. 12, 10) may determine one or more neurological conditions associated with the detected response. For example, a determination that the user suffers from hallucinations may be interpreted to indicate that the user has a motor disorder such as Parkinson's disease, a memory disorder such as Creutzfeldt-Jakob disease, Lewy body dementia, and/or posterior cortical atrophy; and/or a developmental disorder such as schizophrenia. A determination that the user suffers from delusions may be interpreted to indicate that the user has a motor disorder such as Parkinson's disease; a memory disorder such as Lewy body dementia; and/or a developmental disorder such as schizophrenia.

Advantageously, if the systems 600, 2010 (FIGS. 12, 10) determine that the user suffers from schizophrenia or is provided with this information, systems 600, 2010 (FIGS. 12, 10) may be configured to provide the user therapeutic applications for treating or mitigating the effects of schizophrenia. Such treatments may include avatar therapy, in which the display system may present an avatar as augmented reality content to the user, to reduce the threat or danger perceived from hallucinated voices, people, etc. It will be appreciated that some schizophrenic users may have hallucinations of a particular voice and/or person. In some embodiments, the systems 600, 2010 may be configured to allow the user to select an avatar in the form of augmented reality content that has the appearance and/or voice of the hallucination perceived by the user. The systems 600, 2010 may also be configured to display the avatar to the user and allow the user to interact with the avatar. The actions and/or words of the avatar may be controlled by a clinician, or a program, and may be devised to reduce the fear or apprehension associated with the hallucination and to encourage the user to oppose the hallucinated voice or person. Without being limited by theory, it is believed that repeated exposure to the avatar may allow the user to increase their confidence in opposing the hallucinated voice or person. In some embodiments, systems 600, 2010 may be configured to record the interaction by, e.g., utilizing a microphone to record the user's speech and also recording the visual and auditory content provided by the system in the form of the avatar. These recordings may be subsequently be played for the user, the clinician, etc.

In another example, the systems 600, 2010 (FIGS. 12, 10) may be configured to evaluate mood and/or behavior-related conditions, such as depression, anxiety, and/or mania. Diagnostic testing to detect major depression may involve displaying augmented reality and/or virtual reality content, providing guided imagery and/or audio, performing eye tracking, imaging in reflections of the user, and utilizing a microphone to detect audible responses. For example, the systems 600, 2010 (FIGS. 12, 10) may be configured to determine a user's mood based on the user's tone of voice, facial expressions, and/or body posture. Depression may be detected based on extended monitoring of the user and detecting if the user exhibits a lack of eye gaze, poor personal hygiene, and/or a low activity level. In some embodiments, if the systems 600, 2010 (FIGS. 12, 10) determines that the user suffers from major depression or is provided with this information, systems 600, 2010 (FIGS. 12, 10) may be configured to provide the user therapeutic applications for treating major depression. Such treatments may include an AR device 608 displaying guided content stimulating the interest of a user or presenting to the user images or audio associated with a memory known to be pleasant for the user. The systems 600, 2010 (FIGS. 12, 10) may also identify and/or highlight others who are exhibiting positive/happy emotions so that the user may associate with others to improve the user's mood. The systems 600, 2010 may identify or provide virtual content depicting other objects that is known or is likely to bring the user happiness. In some aspects, major depression may be indicated by detection for indicia of depressed mood, changes in eating or sleeping patterns, loss of energy, lack of initiative, low self-esteem, poor concentration, lack of enjoyment of previously pleasurable activities, and/or self-destructive thoughts or behavior. It will be appreciated in some of these indicia may be directly detected by the systems 600, 2010 (FIGS. 12, 10) and some may be reported to the systems 600, 2010 (FIGS. 12, 10) by the user and/or by a $3^{rd}$ party such as a clinician that interacts with the user. All of these may be part of the detected behavior responses of block 622.

Based on detected behavior responses 622, the systems 600, 2010 (FIGS. 12, 10) may determine one or more neurological conditions associated with the detected response. For example, detected signs of depression may be determined to indicate motor disorders such as Parkinson's disease, memory disorders such as Creutzfeldt-Jakob disease, Lewy body dementia, frontotemporal dementia, and/or vascular dementia; behavioral disorders such as post-traumatic stress disorder; developmental disorders such as bipolar affective disorder or Down's syndrome; and/or injuries such as brain tumor and/or traumatic brain injury. Detected signs of apathy may be determined to indicate memory disorders such as Creutzfeldt-Jakob disease and/or frontotemporal dementia; learning disorders such as non-verbal learning disabilities; behavioral disorders such as depression; developmental disorders such as bipolar affective disorder, Down's syndrome, and/or schizophrenia; and/or injuries such as hydrocephalus. Detected signs of fatigue may be determined to indicate nervous system disorders such as multiple sclerosis, neuromyelitis optica, and/or transverse myelitis; motor disorders such as motor neuron disease, amyotrophic lateral sclerosis, and/or Kennedy's disease; behavioral disorders such as depression or stress; and/or injuries such as brain tumor and/or traumatic brain injury.

Diagnostic testing to detect anxiety disorders may include displaying augmented reality and/or virtual reality content, providing guided imagery and/or audio, conducting eye tracking, and/or imaging the user via a reflection. For example, a user's preoccupation with worrisome thoughts may be detected by the systems 600, 2010 (FIGS. 12, 10) based on a lack of eye gaze, body shaking, elevated heart rate, dilated pupils, and/or avoidance behaviors. It will be appreciated that these behaviors, as well as any correlating triggers (e.g., situations, people, or objects that are likely to cause anxiety) may be tracked over time and patterns of these behaviors may be determined to indicate worrisome thoughts on the part of the user. In some embodiments, therapeutic applications related to anxiety disorders may include an AR device 608 providing augmented reality content known to be relaxing to a user so as to decrease anxiety or panic and reduce suspicions or aversions experienced by the user. In some aspects, therapeutic content may include white noise, blurring, or coloring out a portion of the visual input, or otherwise augmenting content to lessen the sensory input and stimulation of the user.

Based on the user's detected behavior responses 622, the systems 600, 2010 (FIGS. 12, 10) may determine one or more neurological conditions associated with the detected response, e.g., an anxiety response. For example, general anxiety may be determined to indicate motor disorders such as Parkinson's disease; memory disorders such as Creutzfeldt-Jakob disease; developmental disorders such as Down's syndrome; injuries such as traumatic brain injury; and/or behavioral disorders such as eating disorders, anorexia, bulimia nervosa, obsessive-compulsive disorder, and/or post-traumatic stress disorder. Detected signs of paranoia may be determined to indicate memory disorders such as Creutzfeldt-Jakob disease; and/or behavioral disorders such as obsessive-compulsive disorder. Detected signs of obsessive and/or compulsive behavior may be determined to indicate memory disorders such as Creutzfeldt-Jakob disease and/or or frontotemporal dementia; and/or behavioral disorders such as eating disorders, anorexia, bulimia nervosa, and/or or obsessive-compulsive disorder. Detected repetitive behavior patterns may indicate memory disorders such as frontotemporal dementia; behavioral disorders such as obsessive-compulsive disorder; and/or developmental disorders such as autism spectrum disorders.

In some embodiments, diagnostic testing to detect disorders associated with mania may include displaying augmented reality and/or virtual reality content, providing guided imagery and/or audio, performing eye tracking, and/or utilizing reflections of the user. For example, mania may be detected based on indications that a user is abnormally active and/or cognitively disorganized. In some embodiments, therapeutic applications related to mania disorders may include utilizing the display system to provide augmented reality content known to be relaxing to a user so as to calm the user during periods of manic behavior.

Based on detected behavior responses such as manic responses, the systems 600, 2010 (FIGS. 12, 10) may determine one or more neurological conditions associated with the detected manic response. For example, detected signs of extreme reactions may be interpreted by the systems 600, 2010 to indicate personality disorders such as borderline personality disorder. Detected signs of emotional lability (e.g., inappropriate involuntary laughing and/or crying) may be interpreted to indicate motor disorders such as progressive bulbar palsy or pseudobulbar palsy; memory disorders such as progressive supranuclear palsy; and/or injuries such as traumatic brain injury. Detected signs of psychosis may indicate memory disorders such as Creutzfeldt-Jakob disease and/or developmental disorders such as schizophrenia. Detected signs of mood swings may indicate memory disorders such as Creutzfeldt-Jakob disease; injuries such as migraines; and/or developmental disorders such as attention deficit hyperactivity disorder or bipolar affective disorder. Detected impulsive behavior may indicate memory disorders such as progressive supranuclear palsy; behavioral disorders such as borderline personality disorder; injuries such as traumatic brain injury; and/or developmental disorders such as attention deficit hyperactivity disorder, bipolar affective disorder, and/or fetal alcohol spectrum disorders. Detected hyperactivity may indicate developmental disorders such as attention deficit hyperactivity disorder.

In some embodiments, the systems 600, 2010 (FIGS. 12, 10) may be configured to perform diagnostic testing based on social interactions of the user. Diagnostic and therapeutic functions associated with social interactions of the user may utilize augmented reality and/or virtual reality content, guided imagery and/or audio, eye tracking, time, facial recognition sensors and algorithms, body language detection, and/or one or more microphones. In some aspects, data collected from systems 600, 2010 worn by other users (e.g., users nearby and/or interacting with the primary user) may be correlated to improve tracking and/or analysis of a user's social interactions (e.g., user-specific data in a secondary user indicating fear, surprise, anger, or confusion in response to a statement or action of the primary user). The display systems may further be configured to determine mental conditions in users of other systems based on observation and/or knowledge of human anatomy, physiology, time-location correlation, or personal shared information.

In one example, a detected lack of eye contact with others may be interpreted by the system to indicate memory disorders such as progressive supranuclear palsy; behavioral disorders such as conduct disorder or social anxiety; and/or developmental disorders such as autism spectrum disorders or bipolar affective disorder. Therapeutic content for conditions associated with a lack of eye contact may include displaying (via the system 2010 of FIG. 10) vision therapy activities to stimulate visual arousal and improve eye contact (e.g., games based on increasing eye contact duration). In another example, excessive direct eye gaze may be detected, and interpreted to indicate behavioral disorders such as anger disorders, anxiety, and/or phobias. Fleeting peripheral glances may also be detected by the system, and may be interpreted to indicate developmental disorders such as autism spectrum disorders.

In a further example, the systems 600, 2010 (FIGS. 12, 10) may detect signs of difficulty interpreting nonverbal cues, such as body language, facial expressions, understanding personal space, or other nonverbal indications. Such difficulty may indicate learning disorders such as non-verbal learning disabilities; and/or developmental disorders such as autism spectrum disorders. Therapeutic content for conditions associated with a lack of interactional social skills may include utilizing the display system to identify responses and emotional states in social situations, identify important points in a conversation to eliminate distraction, and/or or display content that shows socially acceptable actions (e.g., using augmented reality content displayed over multiple depth planes to indicate acceptable personal space). In addition to difficulty with social interactions, the systems 600, 2010 (FIGS. 12, 10) may also be configured to detect a lack of social interaction or communication, which may indicate behavioral disorders such as anxiety, depression, post-traumatic stress disorder, or social anxiety, and/or developmental disorders such as autism spectrum disorders or fetal alcohol spectrum disorders. The systems 600, 2010 (FIGS. 12, 10) may be configured to detect avoidance symptoms, which may indicate behavioral disorders such as anxiety, post-traumatic stress disorder, or social anxiety. In some embodiments, the systems 600, 2010 (FIGS. 12, 10) may further be configured to detect signs of hyperarousal, which may be interpreted to be indicative of behavioral disorders such as post-traumatic stress disorder. Therapeutic content for conditions associated with hyperarousal may include identifying triggering situations or people and providing exposure therapy to gradually lessen the fears of the user.

In some embodiments, the systems 600, 2010 (FIGS. 12, 10) may be configured to detect and possibly treat obsessive-compulsive disorders. The systems 600, 2010 (FIGS. 12, 10) may be configured to detect that the user performs repetitive actions such as cleaning and/or or touching objects; has an aversion to or obsession with certain behaviors; and/or exhibits avoidance of, or obsession with common substances and/or objects. Such behaviors may be determined by the systems 600, 2010 (FIGS. 12, 10) to indicate compulsive disorders.

Detected obsessive tendencies in immediate memory (e.g., repetitive actions) may be determined to indicate pathological obsessiveness. For example, if a user is found to repeat a particular behavior (e.g., touching a particular surface or object, turning the same light switch on or off, picking at one's skin, pulling hair out, checking one's appearance in a mirror, etc.) within a short time such as 1 minute, 2 minutes, 5 minutes, or a similar time period and/or without an apparent reason for doing so (e.g., without observing a particular stimuli that is normally associated with causing such a behavior), obsessive compulsive disorder may be indicated. Obsessive compulsive disorder may also be indicated if the systems 600, 2010 (FIGS. 12, 10) observe that a user spends a great deal of time preoccupied with objects within view of a display system 2010 (FIG. 10) worn by the user (e.g., arranging, ordering, collecting, and/or hoarding items). In other aspects, obsessive tendencies such as checking behaviors and/or obsessions focusing on the body or appearance of the user may be determined to indicate body dysmorphic disorder. Obsessive tendencies such as getting a positive feeling from pulling out body hair or picking at skin to relieve stress may be determined to indicate body focused repetitive behaviors such as trichotillomania (hair-pulling disorder and skin-picking) or dermotillomania (excoriation disorder).

It will be appreciated that some of these obsessive-compulsive behaviors may be observed over a prolonged period of time (e.g., days, weeks, months, or years) and may not be readily apparent to third parties or even to the user. In some embodiments, the systems 600, 2010 (FIGS. 12, 10) may be configured to catalog user behaviors and to determine patterns of behavior, including patterns involving repetition of similar behaviors and the context in which those behaviors are performed. Advantageously, the long-term wearing comfort provided by the proper vergence-accommodation matching of the display system 2010 facilitates these pattern determinations due to the ability of the user to wear the display device regularly and for long durations at a time.

In some embodiments, a user's compulsive arranging, ordering, and/or collecting tendencies may be tested by presenting information such as several virtual objects in an already grouped or ordered fashion (e.g., cans of food in a cabinet and a virtual shopping basket of additional cans). The information may be presented to the user, for example, by a display 62 as depicted in FIG. 2. The user's response, such as continually rearranging, moving, or manipulating the virtual objects, may be detected based on gesture recognition or other user interaction mechanisms. The user's compulsive behavior may be evaluated based on the frequency of interacting with the stimuli; moving of the cans from cabinet to shopping basket and back; the accuracy of object placement; and/or the ordering of colors, sizes, or labeling, or the like.

In some embodiments, a user's aversion to perceived or actual contaminants may be tested by asking the user to react to different chemicals, allergens, microbes, or the like, perceived to be or actually located within the user's environment. Such a test may be carried out at least partially by components of the displays depicted in FIGS. 2, 6, 10, and 12, and may utilize circuitry and programming in processing module 140 and/or remote processing module 150 (FIG. 9D). In the test, the user may be presented with virtual picture stimuli or enhanced real world objects, such as outlines around cleaning chemical bottles, ultraviolet light projected on surfaces to highlight proteins, and/or processed analyses of potential contaminants like bacteria, viruses and allergens using magnification, pattern recognition algorithms, multispectral analysis, or professional/expert consultation to perform the analyses that will be presented to the user. The systems 600, 2010 (FIGS. 12, 10) may then detect the reaction of the user to the stimuli through detected behavioral responses (e.g., flinching, backing away, grimacing, or vomiting) and/or physiological responses (e.g., sweating, increased heart rate). The user's compulsive behavior may be evaluated based on the user's response to otherwise normal objects and conditions.

In some embodiments, the systems 600, 2010 (FIGS. 12, 10) may be configured to provide therapeutic content to decrease obsessive and/or compulsive behaviors. For example, the display system 2010 (FIG. 10) may present an enhanced presentation or analysis of a surface to show whether it is actually clean or dirty. In another example, real world objects may be modified by the display system to make them appear cleaner to the user to reduce anxiety. Behavior aids may also include quantification and/or identification of identified repetitive activities. In some aspects, the activities or objects may be highlighted or recorded for playback, and a "score" may be calculated and presented to the user. A user may be incentivized to keep the score low by avoiding the identified repetitive behaviors.

Sensory Function

Collected user data, such as data collected by the display system 2010 (FIG. 10), may be used to perform testing of a user's sensory functioning. In some aspects, sensory function testing may allow the systems 600, 2010 (FIGS. 12, 10) to assess the functional level of fine touch, pain, temperature, or the like, of a user. In some embodiments, the systems 600, 2010 (FIGS. 12, 10) may be configured to test the primary sensation of a user and/or to passively monitor signs indicative of the primary sensation of the user. Diagnostic testing of primary sensation may include displaying augmented reality and/or virtual reality content, providing guided imagery, and/or utilizing clinician-worn display devices. In some embodiments, various sensory stimuli, such as heat, electric current, vibrations, audio stimuli, visual stimuli, or the like, may be presented, and the detected response of the user may be measured and compared with an expected response. In some implementations, a clinician-worn device may allow the clinician to view the user's response with a normal response augmented for comparison. Sensory tests may be performed on both sides of the body and from proximal to distal on each extremity to allow asymmetries in sensory response to be detected. Passive monitoring may be implemented by detecting a user's response to stimuli detected in the world around the user, rather than by actively providing the stimuli. In one example of passive monitoring, the systems 600, 2010 (FIGS. 12, 10) may be configured to passively monitor a user's ability to sense heat. The system may include an outward facing camera that may function as a thermal camera to monitor the temperature of objects within the user's field of view. The system 600, 2010 (FIGS. 12, 10) may use the input from the thermal camera and one or more body cameras to determine when the user is touching a hot object, such as a stove, and observe the user's reaction (e.g., dilating pupils due to pain, screaming, a quick retraction of the body part touching the object, or the like) or lack of a reaction to touching the hot object. It will be appreciated that the lack of a reaction may indicate improper sensory functioning.

Diagnostic tests associated with primary sensation may include light touch and/or pin prick testing. Signs of numbness and/or tingling may be detected, and may be interpreted as indicating nervous system disorders such as acute disseminated encephalomyelitis, Guillain-Barré syndrome, multiple sclerosis, or transverse myelitis, and/or injuries such as migraine. Signs of heightened sensitivity to touch (e.g., a reaction such as jumping or screaming) may be interpreted to indicate nervous system disorders such as transverse myelitis or multiple sclerosis, and/or injuries such as hydrocephalus. Diagnostic tests may further include temperature testing, such as by applying a cool piece of metal to the skin. Vibration sensing may be tested by placing a vibrating structure, such as a tuning fork or a vibrating structure that is part of the system 600, 2010, on an extremity of a patient and instructing the patient to report when the vibration stops. In some aspects, the vibrating structure of the system 600, 2010 may be mounted to a part of the frame 80 of the display device 60 (FIG. 9D). Further diagnostic testing of primary sensation may include joint position sensation testing and two-point discrimination testing.

In some embodiments, the systems 600, 2010 (FIGS. 12, 10) may further be configured to evaluate a patient's cortical sensation, including extinction, to help localize lesions to specific nerves, nerve roots, and/or regions of the spinal cord, brain stem, thalamus, or cortex. Diagnostic techniques may include graphesthesia testing (the ability of a patient to identify letters or numbers being traced onto the skin of the patient), stereognosis testing (the ability of a patient to identify an object based on tactile sensation), and/or tactile extinction (the ability of a patient to identify double simultaneous tactile stimulation). Data from primary sensation testing may then be correlated with the results of cortical sensation testing. Detected somatosensory deficits may be interpreted to indicate lesions in peripheral nerves, nerve roots, posterior columns or anterolateral sensory systems of the spinal cord or brain stem, thalamus, or sensory cortex. Intact primary sensation accompanied by deficits in cortical sensation may indicate a lesion in the contralateral sensory cortex, while deficits in primary sensation may be interpreted to indicate severe cortical lesions. Extinction accompanied by intact primary sensation may indicate lesions of the right parietal lobe, right frontal lesions, subcortical lesions, or left hemisphere lesions.

Based on detected behavior responses 622, the systems 600, 2010 (FIGS. 12, 10) may determine one or more neurological conditions associated with the detected response. For example, signs of sensory loss may indicate nervous system disorders such as neuromyelitis optica, motor disorders such as Kennedy's disease, and/or injuries such as brain tumors. Detected signs of hypersensitivity to sensory stimuli may be interpreted to indicate cognitive disorders such as sensory processing disorder, behavioral disorders such as post-traumatic stress disorder, developmental disorders such as autism spectrum disorders, and/or injuries such as migraine. Detected signs of hyposensitivity to sensory stimuli may be interpreted to indicate cognitive disorders such as sensory processing disorder and/or developmental disorders such as autism spectrum disorders.

It will be appreciated that for all of the analyses disclosed herein, the display system may be configured to make a preliminary conclusion regarding the results of the analysis. This preliminary conclusion may include a determination that one or more possible conditions are present, and may provide probabilities that the user has the one or more possible conditions. The preliminary conclusion and/or any related probabilities may be provided to the user as augmented reality content, as audible announcements, and/or as virtual images and/or videos. It will be appreciated that any of these conclusions or content may be stored as an update to a patient's history file. The display system may also be configured to provide suggestions for follow-up by the user and/or to automatically initiated a follow-up by forwarding information to a clinician. In some other embodiments, the display system be configured to not make any determination and to simply transmit information in the form of images, audio files, video files, or the like, to a clinician and/or another computer system for further analysis and the determination of conclusions. In yet other embodiments, the display system may be configured to both make a preliminary conclusion and transmit images of the user to a clinician and/or other computer system for further analysis.

Computer Vision to Detect Reflections and Objects in Ambient Environment

As discussed above, the display system may be configured to detect objects in or properties of the environment surrounding the user. The detection may be accomplished using a variety of techniques, including various environmental sensors (e.g., cameras, audio sensors, temperature sensors, etc.), as discussed herein.

In some embodiments, objects present in the environment may be detected using computer vision techniques. For example, as disclosed herein, the display system's forward-facing camera may be configured to image the ambient environment and the display system may be configured to perform image analysis on the images to determine the presence of objects in the ambient environment. The display system may analyze the images acquired by the outward-facing imaging system to perform scene reconstruction, event detection, video tracking, object recognition, object pose estimation, learning, indexing, motion estimation, or image restoration, etc. As other examples, the display system may be configured to perform face and/or eye recognition to determine the presence and location of faces and/or human eyes in the user's field of view. One or more computer vision algorithms may be used to perform these tasks. Non-limiting examples of computer vision algorithms include: Scale-invariant feature transform (SIFT), speeded up robust features (SURF), oriented FAST and rotated BRIEF (ORB), binary robust invariant scalable keypoints (BRISK), fast retina keypoint (FREAK), Viola-Jones algorithm, Eigenfaces approach, Lucas-Kanade algorithm, Horn-Schunk algorithm, Mean-shift algorithm, visual simultaneous location and mapping (vSLAM) techniques, a sequential Bayesian estimator (e.g., Kalman filter, extended Kalman filter, etc.), bundle adjustment, Adaptive thresholding (and other thresholding techniques), Iterative Closest Point (ICP), Semi Global Matching (SGM), Semi Global Block Matching (SGBM), Feature Point Histograms, various machine learning algorithms (such as e.g., support vector machine, k-nearest neighbors algorithm, Naive Bayes, neural network (including convolutional or deep neural networks), or other supervised/unsupervised models, etc.), and so forth.

One or more of these computer vision techniques may also be used together with data acquired from other environmental sensors (such as, e.g., microphone) to detect and determine various properties of the objects detected by the sensors.

As discussed herein, the objects in the ambient environment may be detected based on one or more criteria. When the display system detects the presence or absence of the criteria in the ambient environment using a computer vision algorithm or using data received from one or more sensor assemblies (which may or may not be part of the display system), the display system may then signal the presence of the object.

Additionally or alternatively, the display system may learn to identify the presence of the reflection and/or object in the environment based on the user's behaviors (or behaviors of a group of users). For example, the display system may learn to identify the presence of the object in the environment by associating certain actions or behaviors of the user or a group of users to certain objects that are present in the ambient environment and use this association to predict whether the object is present.

Machine Learning

A variety of machine learning algorithms may be used to learn to identify the presence of objects in the ambient environment. Once trained, the machine learning algorithms may be stored by the display system. Some examples of machine learning algorithms may include supervised or non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, a-priori algorithms), artificial neural network algorithms (such as, for example, Perceptron), deep learning algorithms (such as, for example, Deep Boltzmann Machine, or deep neural network), dimensionality reduction algorithms (such as, for example, Principal Component Analysis), ensemble algorithms (such as, for example, Stacked Generalization), and/or other machine learning algorithms. In some embodiments, individual models may be customized for individual data sets. For example, the wearable device may generate or store a base model. The base model may be used as a starting point to generate additional models specific to a data type (e.g., a particular user), a data set (e.g., a set of additional images obtained), conditional situations, or other variations. In some embodiments, the display system may be configured to utilize a plurality of techniques to generate models for analysis of the aggregated data. Other techniques may include using predefined thresholds or data values.

The criteria for detecting an object may include one or more threshold conditions. If the analysis of the data acquired by the environmental sensor indicates that a threshold condition is passed, the display system may provide a signal indicating the detection the presence of the object in the ambient environment. The threshold condition may involve a quantitative and/or qualitative measure. For example, the threshold condition may include a score or a percentage associated with the likelihood of the reflection and/or object being present in the environment. The display system may compare the score calculated from the environmental sensor's data with the threshold score. If the score is higher than the threshold level, the display system may detect the presence of the reflection and/or object. In some other embodiments, the display system may signal the presence of the object in the environment if the score is lower than the threshold. In some embodiments, the threshold condition may be determined based on the user's emotional state and/or the user's interactions with the ambient environment.

In some embodiments, the threshold conditions, the machine learning algorithms, or the computer vision algorithms may be specialized for a specific context. For example, in a diagnostic context, the computer vision algorithm may be specialized to detect certain responses to the stimulus. As another example, the display system may execute facial recognition algorithms and/or event tracing algorithms to sense the user's reaction to a stimulus, as discussed herein.

It will be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. For example, computing systems may include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some embodiments, particular operations and methods may be performed by circuitry that is specific to a given function.

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the local processing and data module (70), the remote processing module (72), and remote data repository (74). The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities may be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto may be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems may generally be integrated together in a single computer product or packaged into multiple computer products.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, it will be appreciated that the systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Accordingly, the claims are not intended to be limited to the embodiments shown herein, but are to be accorded the widest scope consistent with this disclosure, the principles and the novel features disclosed herein.

What is claimed is:

1. A display system comprising:
   a display that is mountable on a head of a user, the display comprising one or more waveguides configured to transmit light from a surrounding environment to the user and to project light to the user to display image content;
   an environmental sensor configured to detect first environmental data that describes an environment proximal to the display system;
   a user sensor configured to collect first user-specific data of the user; and
   processing circuitry configured to;
      analyze the first user-specific data to identify a physiological, behavioral, or environmental abnormality of the user;
      share both the first user-specific data and the first environmental data with one or more other display systems;
      receive, from at least one other display system, second environmental data that describes an environment proximal to the at least one other display system; and
      analyze the first environmental data and the second environmental data to determine at least one factor that is present in both the first environmental data and the second environmental data, and to determine that the at least one factor is correlated to the abnormality of the user.

2. The display system of claim 1, wherein the processing circuitry is configured to transmit and receive environmental data and user-specific data between display systems worn by different users.

3. The display system of claim 2, wherein at least one of the different users is a clinician, and wherein the display system worn by the clinician is configured to display augmented reality content to the clinician for diagnosis, monitoring, or treatment of the user.

4. The display system of claim 1, wherein the processing circuitry is configured to transmit at least one of the first environmental data or the first user-specific data to the one or more other display systems responsive to the abnormality being identified.

5. The display system of claim 1, wherein the processing circuitry is further configured to:
   receive, from the at least one other display system, second user-specific data of at least one other user of the at least one other display system; and
   analyze the second user-specific data to determine that the at least one other user of the at least one other display system exhibits the same abnormality as the user.

6. The display system of claim 5, wherein the processing circuitry is further configured to:
   determine location data of the display system; and
   detect an occurrence of similar physiological, behavioral, or environmental abnormalities in a plurality of display device wearers in physical proximity based on the location data and at least one of the received second environmental data or the received second user-specific data.

7. The display system of claim 6, wherein the processing circuitry is further configured to determine a location of an environmental abnormality based at least in part on location data from the display devices worn by the plurality of display device wearers.

8. The display system of claim 6, wherein the processing circuitry is further configured to provide a remote notification based on the detected occurrence of similar physiological, behavioral, or environmental abnormalities.

9. The display system of claim 1, wherein the first user-specific data comprises behavioral information characterizing behavior of the user.

10. The display system of claim 1, wherein the one or more waveguides are configured to project the light to the user with variable amounts of wavefront divergence.

11. A method comprising:
    collecting first environmental data from an environmental sensor of a display system including an augmented reality display that is mountable on a head of a user, the display comprising one or more waveguides configured to transmit light from a surrounding environment to the user and to project light to the user to display image content, wherein the first environmental data describes the environment proximal to the display;

collecting first user-specific data of the user from a user sensor of the display system;

analyzing, by processing circuitry of the display system, the first user-specific data to identify a physiological, behavioral, or environmental abnormality of the user;

sharing, by the processing circuitry, both the first user-specific data and the first environmental data with one or more other display systems;

receiving, from at least one other display system, second environmental data that describes an environment proximal to the at least one other display system; and analyzing, by the processing circuitry, the first environmental data and the second environmental data to determine at least one factor that is present in both the first environmental data and the second environmental data, and to determine that the at least one factor is correlated to the abnormality of the user.

12. The method of claim 11, wherein the user-specific data and the environmental data are shared with the one or more other display systems worn by different users.

13. The method of claim 12, wherein at least one of the different users is a clinician, and wherein the display system worn by the clinician is configured to display augmented reality content to the clinician for diagnosis, monitoring, or treatment of the user.

14. The method of claim 11, wherein the sharing comprises transmitting at least one of the first environmental data or the first user-specific data to the one or more other display systems responsive to the abnormality being identified.

15. The method of claim 11, further comprising:
receiving, from the at least one other display system, second user-specific data of at least one other user of the at least one other display system; and
analyzing, by the processing circuitry, the second user-specific data to determine that the at least one other user of the at least one other display system exhibits the same abnormality as the user.

16. The method of claim 15, further comprising:
determining location data of the display system; and
detecting an occurrence of similar physiological, behavioral, or environmental abnormalities in a plurality of display device wearers in physical proximity based on the location data and at least one of the received second environmental data or the received second user-specific data.

17. The method of claim 16, further comprising determining a location of an environmental abnormality based at least in part on location data from the display devices worn by the plurality of display device wearers.

18. The method of claim 16, further comprising providing a remote notification based on the detected occurrence of similar physiological, behavioral, or environmental abnormalities.

19. The method of claim 11, wherein the first user-specific data comprises behavioral information characterizing behavior of the user.

20. The method of claim 11, wherein the one or more waveguides are configured to project the light to the user with variable amounts of wavefront divergence.

* * * * *